United States Patent
Boulter et al.

(10) Patent No.: US 8,008,438 B2
(45) Date of Patent: *Aug. 30, 2011

(54) HIGH AFFINITY NY-ESO T CELL RECEPTORS

(75) Inventors: Jonathan Michael Boulter, Abingdon (GB); Lucy Boulter, legal representative, Oxfordshire (GB); Bent Karsten Jakobsen, Oxfordshire (GB); Yi Li, Oxfordshire (GB); Peter Eamon Molloy, Oxfordshire (GB); Steven Mark Dunn, Oxfordshire (GB)

(73) Assignee: Immunocore Limited, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/854,691

(22) Filed: Aug. 11, 2010

(65) Prior Publication Data

US 2011/0014169 A1    Jan. 20, 2011

Related U.S. Application Data

(62) Division of application No. 11/596,458, filed as application No. PCT/GB2005/001924 on May 18, 2005.

(30) Foreign Application Priority Data

May 19, 2004 (GB) .................................. 0411123.3
Sep. 3, 2004 (GB) .................................. 0419643.2

(51) Int. Cl.
*C07K 1/00* (2006.01)
*C07K 14/00* (2006.01)
*C07K 17/00* (2006.01)

(52) U.S. Cl. ...................................... 530/350

(58) Field of Classification Search ........................ None
See application file for complete search history.

(56) References Cited

FOREIGN PATENT DOCUMENTS

WO   WO 03/020763 A    3/2003

OTHER PUBLICATIONS

Pardoll, 2002, Nat. Biotech. vol. 20: 1207-1208.*
Morgan et al., 2006, Science, vol. 314: 126-129.*
Jäger et al., "Simultaneous humoral and cellular immune response against cancer-testis antigen NY-ESO-1: definition of human histocompatibility leukocyte antigen (HLA)-A2-binding peptide epitopes," *J. Exp. Med.* 187, 265-70, 1998.
Li et al., "Directed evolution of human T-cell receptors with picomolar affinities by phage display," *Nature Biotechnol.* 23, 349-54, 2005.

* cited by examiner

*Primary Examiner* — Amy Juedes
(74) *Attorney, Agent, or Firm* — Banner & Witcoff, Ltd.

(57) ABSTRACT

The present invention provides T cell receptors (TCRs) having the property of binding to SLLMWITQC (SEQ ID NO:126)-HLA-A*0201, the SLLMWITQC (SEQ ID NO:126) peptide being derived from the NY-ESO-1 protein which is expressed by a range of tumor cells. The TCRs have a $K_D$ for the said that peptide-HLA complex of less than or equal to 1 μM and/or have an off-rate ($k_{off}$) of $1\times10^{-3}$ $S^{-1}$ or slower.

2 Claims, 41 Drawing Sheets

(SEQ ID No: 1)

(SEQ ID No: 2)

Figure 2a atgcaggaggtgacacagattcctgcagctctgagtgtcccagaaggagaaaacttggttctcaactgcagtttcactgatag
cgctatttacaacctccagtggtttaggcaggaccctgggaaaggtctcacatctctgttgcttattcagtcaagtcagagaga
gcaaacaagtggaagacttaatgcctcgctggataaatcatcaggacgtagtactttatacattgcagcttctcagcctggtga
ctcagccacctacctctgtgctgtgaggcccacatcaggaggaagctacatacctacatttggaagaggaaccagccttatt
gttcatccgtatatccagaaccctgaccctgccgtgtaccagctgagagactctaaatccagtgacaagtctgtctgcctattc
accgattttgattctcaaacaaatgtgtcacaaagtaaggattctgatgtgtatatcacagacaaaactgtgctagacatgaggt
ctatggacttcaagagcaacagtgctgtggcctggagcaacaaatctgactttgcatgtgcaaacgccttcaacaacagcatt
attccagaagacaccttcttccccagcccagaaagttcctaa (SEQ ID No: 3)

Figure 2b atgggtgtcactcagaccccaaaattccaggtcctgaagacaggacagagcatgacactgcagtgtgcccaggatatgaac
catgaatacatgtcctggtatcgacaagacccaggcatgggctgaggctgattcattactcagttggtgctggtatcactga
ccaaggagaagtccccaatggctacaatgtctccagatcaaccacagaggatttcccgctcaggctgctgtcggctgctccc
tcccagacatctgtgtacttctgtgccagcagttacgtcgggaacaccggggagctgttttttggagaaggctctaggctgac
cgtactggaggacctgaaaaacgtgttcccacccgaggtcgctgtgtttgagccatcagaagcagagatctcccacaccca
aaaggccacactggtgtgcctggccacaggcttctaccccgaccacgtggagctgagctggtgggtgaatgggaaggag
gtgcacagtggggtcagcacagacccgcagcccctcaaggagcagcccgccctcaatgactccagatacgctctgagca
gccgcctgagggtctcggccaccttctggcaggaccccgcaaccacttccgctgtcaagtccagttctacgggctctcgg
agaatgacgagtggacccaggataggggccaaacccgtcacccagatcgtcagcgccgaggcctggggtagagcagact
aa
(SEQ ID No: 4)

(SEQ ID No: 5)

(SEQ ID No: 6)

Figure 4a atgcaggaggtgacacagattcctgcagctctgagtgtcccagaaggagaaaacttggttctcaactgcagtttcactgatag
cgctatttacaacctccagtggtttaggcaggaccctgggaaaggtctcacatctctgttgcttattcagtcaagtcagagaga
gcaaacaagtggaagacttaatgcctcgctggataaatcatcaggacgtagtactttatacattgcagcttctcagcctggtga
ctcagccacctacctctgtgctgtgaggcccacatcaggaggaagctacatacctacatttggaagaggaaccagccttatt
gttcatccgtatatccagaaccctgaccctgccgtgtaccagctgagagactctaaatccagtgacaagtctgtctgcctattc
accgattttgattctcaaacaaatgtgtcacaaagtaaggattctgatgtgtatatcacagacaaatgtgtgctagacatgaggt
ctatggacttcaagagcaacagtgctgtggcctggagcaacaaatctgactttgcatgtgcaaacgccttcaacaacagcatt
attccagaagacaccttcttcccagcccagaaagttcctaa
(SEQ ID No: 7)

Figure 4b atgggtgtcactcagaccccaaaattccaggtcctgaagacaggacagagcatgacactgcagtgtgcccaggatatgaac
catgaatacatgtcctggtatcgacaagacccaggcatggggctgaggctgattcattactcagttggtgctggtatcactga
ccaaggagaagtccccaatggctacaatgtctccagatcaaccacagaggatttcccgctcaggctgctgtcggctgctccc
tcccagacatctgtgtacttctgtgccagcagttacgtcgggaacaccggggagctgttttttggagaaggctctaggctgac
cgtactggaggacctgaaaaacgtgttcccacccgaggtcgctgtgtttgagccatcagaagcagagatctcccacaccca
aaaggccacactggtgtgcctggccacaggcttctaccccgaccacgtggagctgagctggtgggtgaatgggaaggag
gtgcacagtggggtctgcacagacccgcagcccctcaaggagcagcccgccctcaatgactccagatacgctctgagca
gccgcctgagggtctcggccaccttctggcaggaccccgcaaccacttccgctgtcaagtccagttctacgggctctcgg
agaatgacgagtggacccaggatagggccaaacccgtcacccagatcgtcagcgccgaggcctggggtagagcagact
aa
(SEQ ID No: 8)

Figure 5a

```
M Q E V T Q I P A A L S V P E G E N L V L N C S F T D S A I Y N L Q W
F R Q D P G K G L T S L L L I Q S S Q R E Q T S G R L N A S L D K S S
G R S T L Y I A A S Q P G D S A T Y L C A V R P T S G G S Y I P T F G
R G T S L I V H P Y I Q N P D P A V Y Q L R D S K S S D K S V C L F T
D F D S Q T N V S Q S K D S D V Y I T D K C V L D M R S M D F K S N S
A V A W S N K S D F A C A N A F N N S I I P E D T F F P S P E S S
```
(SEQ ID No: 9)

Figure 5b

```
M G V T Q T P K F Q V L K T G Q S M T L Q C A Q D M N H E Y M S W Y R
Q D P G M G L R L I H Y S V G A G I T D Q G E V P N G Y N V S R S T T
E D F P L R L L S A A P S Q T S V Y F C A S S Y V G N T G E L F F G E
G S R L T V L E D L K N V F P P E V A V F E P S E A E I S H T Q K A T
L V C L A T G F Y P D H V E L S W W V N G K E V H S G V C T D P Q P L
K E Q P A L N D S R Y A L S S R L R V S A T F W Q D P R N H F R C Q V
Q F Y G L S E N D E W T Q D R A K P V T Q I V S A E A W G R A D
```
(SEQ ID No: 10)

Figure 6

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>LLD</u>G<u>T</u>YIPTFGRGTSLIVHPY
(SEQ ID No: 11)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVR<u>H</u>TS<u>N</u>G<u>YFP</u>PTFGRGTSLIVHPY
(SEQ ID No: 12)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>MT</u>GG<u>T</u>YIPTFGRGTSLIVHPY
(SEQ ID No: 13)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>LY</u>GG<u>T</u>YIPTFGRGTSLIVHPY
(SEQ ID No: 14)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>MI</u>GG<u>T</u>YIPTFGRGTSLIVHPY
(SEQ ID No: 15)

Figure 6, cont.

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPLTGGTYIPTFGRGTSLIVHPY
(SEQ ID No: 16)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPLTGGSYIPTFGRGTSLIVHPY
(SEQ ID No: 17)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPATGGTYIPTFGRGTSLIVHPY
(SEQ ID No: 18)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPQTVPTYIPTFGRGTSLIVHPY
(SEQ ID No: 19)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPMSGGTYIPTFGRGTSLIVHPY
(SEQ ID No: 20)

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPYQSGHYMPTFGRGTSLIVHPY
(SEQ ID No: 21)

Figure 6, cont.

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGG<u>D</u>Y<u>T</u>PTFGRGTSLIVHPY
(SEQ ID No: 22)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>ML</u>GG<u>T</u>YIPTFGRGTSLIVHPY
(SEQ ID No: 23)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>LQD</u>G<u>T</u>YIPTFGRGTSLIVHPY
(SEQ ID No: 24)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>MTDS</u>YIPTFGRGTSLIVHPY
(SEQ ID No: 25)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>LVDP</u>YIPTFGRGTSLIVHPY
(SEQ ID No: 26)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRP<u>EVDA</u>YIPTFGRGTSLIVHPY
(SEQ ID No: 27)

Figure 6, cont.

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLEDSTYIPTFGRGTSLIVHPY
(SEQ ID No: 28)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPLVGGVYIPTFGRGTSLIVHPY
(SEQ ID No: 29)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGNYIPTFGRGTSLIVHPY
(SEQ ID No: 30)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTTGGSYIPTFGRGTSLIVHPY
(SEQ ID No: 31)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPISGGSYIPTFGRGTSLIVHPY
(SEQ ID No: 32)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPMSGGSYIPTFGRGTSLIVHPY
(SEQ ID No: 33)

Figure 6, cont.

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPMTGGSYIPTFGRGTSLIVHPY
(SEQ ID No: 34)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPISGGSYIPTFGRGTSLIVHPY
(SEQ ID No: 35)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTSGGTYIPTFGRGTSLIVHPY
(SEQ ID No: 36)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPTAGGSYIPAFGRGTSLIVHPY
(SEQ ID No: 37)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPASGGSYIPTFGRGTSLIVHPY
(SEQ ID No: 38)

MQEVTQIPAALSVPEGENLVLNCSFTDSAIYNLQWFRQ
DPGKGLTSLLLIQSSQREQTSGRLNASLDKSSGRSTLYI
AASQPGDSATYLCAVRPATGGSYIPTFGRGTSLIVHPY
(SEQ ID No: 39)

Figure 6, cont.

MQEVTQIPAALSVPEGENLVLNCSFTDSAIYNLQWFRQ
DPGKGLTSLLIQSSQREQTSGRLNASLDKSSGRSTLYI
AASQPGDSATYLCAVRPT_QYTQVPTFGRGTSLIVHPY
(SEQ ID No: 40)

MQEVTQIPAALSVPEGENLALNCSFTDSAIYNLQWFRQ
DPGKGLTSLLIQPSQREQTSGRLNASLDKSSGRSTLYI
AASQPGDSATYLCAVRPTSGGSYIPTFGRGTSLIVHPY
(SEQ ID No: 41)

MQEVTQIPAALSVPEGENLVLNCSFTDSAIYNLQWFRQ
DPGKGLTSLLIPFWQREQTSGRLNASLDKSSGRSTLYI
AASQPGDSATYLCAVRPTSGGSYIPTFGRGTSLIVHPY
(SEQ ID No: 42)

MQEVTQIPAALSVPEGENLVLNCSFTDSAIYNLQWFRQ
DPGKGLTSLLISPWQREQTSGRLNASLDKSSGRSTLYI
AASQPGDSATYLCAVRPTSGGSYIPTFGRGTSLIVHPY
(SEQ ID No: 43)

MQEVTQIPAALSVPEGENLVLNCSFTDSAIYNLQWFRQ
DPGKGLTSLLITPWQREQTSGRLNASLDKSSGRSTLYI
AASQPGDSATYLCAVRPTSGGSYIPTFGRGTSLIVHPY
(SEQ ID No: 44)

MQEVTQIPAALSVPEGENLVLNCSFTDSAIYNLQWFRQ
DPGKGLTSLLIQGWQREQTSGRLNASLDKSSGRSTLYI
AASQPGDSATYLCAVRPTSGGSYIPTFGRGTSLIVHPY
(SEQ ID No: 45)

Figure 6, cont.

MQEVTQIPAALSVPEGENLVLNCSFTDSAIYNLQWFRQ
DPGKGLTSLLL I<u>MGH</u>QREQTSGRLNASLDKSSGRSTLYI
AASQPGDSATYLCAVRPTSGGSYIPTFGRGTSLIVHPY
(SEQ ID No: 46)

MQEVTQIPAALSVPEGENLVLNCSFTDSAIYNLQWFRQ
DPGKGLTSLLL I<u>MGT</u>QREQTSGRLNASLDKSSGRSTLYI
AASQPGDSATYLCAVRPTSGGSYIPTFGRGTSLIVHPY
(SEQ ID No: 47)

MQEVTQIPAALSVPEGENLVLNCSFTDSAIYNLQWFRQ
DPGKGLTSLLL I<u>PFW</u>QREQTSGRLNASLDKSSGRSTLYI
AASQPGDSATYLCAVRP<u>LLD</u>G<u>T</u>YIPTFGRGTSLIVHPY
(SEQ ID No: 48)

MQEVTQIPAALSVPEGENLVLNCSFTDSAIYNLQWFRQ
DPGKGLTSLLL I<u>TPW</u>QREQTSGRLNASLDKSSGRSTLYI
AASQPGDSATYLCAVRP<u>LLD</u>G<u>T</u>YIPTFGRGTSLIVHPY
(SEQ ID No: 49)

MQEVTQIPAALSVPEGENLVLNCSFTDSAIYNLQWFRQ
DPGKGLTSLLL I<u>SPW</u>QREQTSGRLNASLDKSSGRSTLYI
AASQPGDSATYLCAVRP<u>LLD</u>G<u>T</u>YIPTFGRGTSLIVHPY
(SEQ ID No: 50)

MQEVTQIPAALSVPEGENLVLNCSFTDSAIYNLQWFRQ
DPGKGLTSLLL I<u>MGH</u>QREQTSGRLNASLDKSSGRSTLYI
AASQPGDSATYLCAVRP<u>LLD</u>G<u>T</u>YIPTFGRGTSLIVHPY
(SEQ ID No: 51)

Figure 6, cont.

MQEVTQIPAALSVPEGENLVLNCSFTDSAIYNLQWFRQ
DPGKGLTSLLLI<u>MGT</u>QREQTSGRLNASLDKSSGRSTLYI
AASQPGDSATYLCAVRP<u>LLD</u>G<u>T</u>YIPTFGRGTSLIVHPY
(SEQ ID No: 52)

MQEVTQIPAALSVPEGENLVLNCSFTDSAIYNLQWFRQ
DPGKGLTSLLLI<u>MGW</u>QREQTSGRLNASLDKSSGRSTLYI
AASQPGDSATYLCAVRP<u>LLD</u>G<u>T</u>YIPTFGRGTSLIVHPY
(SEQ ID No: 53)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>LR</u>GGSYIPTFGRGTSLIVHPY
(SEQ ID No: 54)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>NDGSG</u>SYIPTFGRGTSLIVHPY
(SEQ ID No: 55)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>AW</u>GG<u>N</u>YIPTFGRGTSLIVHPY
(SEQ ID No: 56)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>A</u>EGG<u>E</u>YIPTFGRGTSLIVHPY
(SEQ ID No: 57)

Figure 6, cont.

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>FT</u>GG<u>G</u>YIPTFGRGTSLIVHPY
(SEQ ID No: 58)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>V</u>SGG<u>D</u>YIPTFGRGTSLIVHPY
(SEQ ID No: 59)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>LDDGGR</u>YIPTFGRGTSLIVHPY
(SEQ ID No: 60)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>NT</u>GG<u>Q</u>YIPTFGRGTSLIVHPY
(SEQ ID No: 61)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>IA</u>GG<u>K</u>YIPTFGRGTSLIVHPY
(SEQ ID No: 62)

MQEVTQIPAALSVPEGENLVLNCSFTDSAIYNLQWFRQ
DPGKGLTSLLLI<u>SPW</u>QREQTSGRLNASLDKSSGRSTLYI
AASQPGDSATYLCAVRP<u>GT</u>GG<u>D</u>YIPTFGRGTSLIVHPY
(SEQ ID No: 63)

Figure 6, cont.

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPAAGGSDIPTFGRGTSLIVHPY
(SEQ ID No: 64)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPLAGGAYIPTFGRGTSLIVHPY
(SEQ ID No: 65)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPARGGDYIPTFGRGTSLIVHPY
(SEQ ID No: 66)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPLGGGIYIPTFGRGTSLIVHPY
(SEQ ID No: 67)

MQEVTQIPAALSVPEGENLVLNCSFTDSAIYNLQWFRQ
DPGKGLTSLLLISPWQREQTSGRLNASLDKSSGRSTLYI
AASQPGDSATYLCAVRPMGGGRYIPTFGRGTSLIVHPY
(SEQ ID No: 68)

MQEVTQIPAALSVPEGENLVLNCSFTDSAIYNLQWFRQ
DPGKGLTSLLLIQGWQREQTSGRLNASLDKSSGRSTLYI
AASQPGDSATYLCAVRPSVGNYIPTFGRGTSLIVHPY
(SEQ ID No: 69)

Figure 6, cont.

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>AT</u>GG<u>N</u>YIPTFGRGTSLIVHPY
(SEQ ID No: 70)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>LT</u>GG<u>A</u>YIPTFGRGTSLIVHPY
(SEQ ID No: 71)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>RES</u>GNYIPTFGRGTSLIVHPY
(SEQ ID No: 72)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>I</u>SGG<u>D</u>YIPTFGRGTSLIVHPY
(SEQ ID No: 73)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>AHN</u>G<u>N</u>YIPTFGRGTSLIVHPY
(SEQ ID No: 74)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>DNTWG T</u>YIPTFGRGTSLIVHPY
(SEQ ID No: 75)

Figure 6, cont.

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>V</u>EGG<u>D</u>YIPTFGRGTSLIVHPY
(SEQ ID No: 76)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>AAS</u>G<u>N</u>YIPTFGRGTSLIVHPY
(SEQ ID No: 77)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>I</u>SGG<u>E</u>YIPTFGRGTSLIVHPY
(SEQ ID No: 78)

MQEVTQIPAALSVPEGENLVLNCSFTDSAIYNLQWFRQ
DPGKGLTSLLLI<u>SP</u>WQREQTSGRLNASLDKSSGRSTLYI
AASQPGDSATYLCAVRP<u>IT</u>GG<u>G</u>YIPTFGRGTSLIVHPY
(SEQ ID No: 79)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>LK</u>GG<u>A</u>YIPTFGRGTSLIVHPY
(SEQ ID No: 80)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>AE</u>GGSYIPTFGRGTSLIVHPY
(SEQ ID No: 81)

Figure 6, cont.

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>ST</u>GG<u>N</u>YIPTFGRGTSLIVHPY
(SEQ ID No: 82)

MQEVTQIPAALSVPEGENLVLNCSFTDSAIYNLQWFRQ
DPGKGLTSLLLIQ<u>GW</u>QREQTSGRLNASLDKSSGRSTLYI
AASQPGDSATYLCAVRP<u>VDDGK</u>YIPTFGRGTSLIVHPY
(SEQ ID No: 83)

Figure 7

M G V T Q T P K F Q V L K T G Q S M T L Q C A Q D M N H E Y M S W Y R Q
D P G M G L R L I H Y S V G A G T T D R G E V P N G Y N V S R S T I E D F P L
R L L S A A P S Q T S V Y F C A S S Y L G N T G E L F F G E G S R L T V L
(SEQ ID No: 84)

M G V T Q T P K F Q V L K T G Q S M T L Q C A Q D M N H E Y M S W Y R Q
D P G M G L R L I H Y S V G A G T T D Q G E V P N G Y N V S R S T I E D F P
L R L L S A A P S Q T S V Y F C A S S Y L G N T G E L F F G E G S R L T V L
(SEQ ID No: 85)

M G V T Q T P K F Q V L K T G Q S M T L Q C A Q D M N H E Y M S W Y R Q
D P G M G L R L I H Y S V G A G T T D Q G E V P N G Y N V S R S T T E D F P
L R L L S A A P S Q T S V Y F C A S S N V G N T G E L F F G E G S R L T V L
(SEQ ID No: 86)

M G V T Q T P K F Q V L K T G Q S M T L Q C A Q D M N H E Y M S W Y R Q
D P G M G L R L I H Y S V G A G T T D Q G E V P N G Y N V S R S T T E D F P
L R L L S A A P S Q T S V Y F C A S S Y V G G T G E L F F G E G S R L T V L
(SEQ ID No: 87)

M G V T Q T P K F Q V L K T G Q S M T L Q C A Q D M N H E Y M S W Y R Q
D P G M G L R L I H Y S V G A G I T D Q G E V P N G Y N V S R S T I E D F P L
R L L S A A P S Q T S V Y F C A S S Y V G N T G E L F F G E G S R L T V L
(SEQ ID No: 88)

Figure 7, cont.

MGVTQTPKFQVLKTGQSMTLQCAQDMNHEYMSWYRQ
DPGMGLRLIHYSVGA T TDQGEVPNGYNVSRSTTEDFP
LRLLSAAPSQTSVYFCASSY L G D TGELFFGEGSRLTVL
(SEQ ID No: 89)

MGVTQTPKFQVLKTGQSMTLQCAQDMNHEYMSWYRQ
DPGMGLRLIHYSVG V G T TDQGEVPNGYNVSRSTTEDFP
LRLLSAAPSQTSVYFCASSY L G D TGELFFGEGSRLTVL
(SEQ ID No: 90)

MGVTQTPKFQVLKTGQS V TLQCAQDMNHEYMSWYRQ
DPGMGLRLIHYSVG V G T TDQGEVPNGYNVSRSTTEDFP
LRLLSAAPSQTSVYFCASSY L G D TGELFFGEGSRLTVL
(SEQ ID No: 91)

DPGMGLRLIHYSV S V G M TDQGEVPNGYNVSRSTTEDFP
LRLLSAAPSQTSVYFCASSYVGNTGELFFGEGSRLTVL
(SEQ ID No: 92)

MGVTQTPKFQVLKTGQSMTLQCAQDMNHEYMSWYRQ
DPGMGLRLIHYSV A I Q TTDQGEVPNGYNVSRSTTEDFPL
RLLSAAPSQTSVYFCASSYVGNTGELFFGEGSRLTVL
(SEQ ID No: 93)

MGVTQTPKFQVLKTGQSMTLQCAQDMNHEYMSWYRQ
DPGMGLRLIHYSV A I Q TTDQGEVPNGYNVSRST I EDFPL
RLLSAAPSQTSVYFCASSY L GNTGELFFGEGSRLTVL
(SEQ ID No: 94)

Figure 7, cont.

MGVTQTPKFQVLKTGQSMTLQCAQDMNHEYMSWYRQ
DPGMGLRLIHYSVS̲V̲GM̲TDQGEVPNGYNVSRSTI̲EDFP
LRLLSAAPSQTSVYFCASSYL̲GNTGELFFGEGSRLTVL
(SEQ ID No: 95)

MGVTQTPKFQVLKTGQSMTLQCAQDMNHEYMSWYRQ
DPGMGLRLIHYSVGAGT̲TDR̲GEVPNGYNVSRSTI̲EDFPL
RLLSAAPSQTSVYFCASSYVGTGELFFGEGSRLTVL
(SEQ ID No: 96)

MGVTQTPKFQVLKTGQSMTLQCAQDMNHEYMSWYRQ
DPGMGLRLIHYSVGAGT̲TDR̲GEVPNGYNVSRSTI̲EDFPL
RLLSAAPSQTSVYFCASSYVGD̲TGELFFGEGSRLTVL
(SEQ ID No: 97)

MGVTQTPKFQVLKTGQSMTLQCAQDMNHEYMSWYRQ
DPGMGLRLIHYSVGAGT̲TDR̲GEVPNGYNVSRSTI̲EDFPL
RLLSAAPSQTSVYFCASSYL̲GD̲TGELFFGEGSRLTVL
(SEQ ID No: 98)

MGVTQTPKFQVLKTGQSMTLQCAQDMNHEYMSWYRQ
DPGMGLRLIHYSVGAGT̲TDR̲GEVPNGYNVSRSTI̲EDFPL
RLLSAAPSQTSVYFCASSF̲VGD̲TGELFFGEGSRLTVL
(SEQ ID No: 99)

Figure 8a

N I Q N P D P A V Y Q L R D S K S S D K S V C L F T
D F D S Q T N V S Q S K D S D V Y I T D K (SEQ ID NO: 100)

Figure 8b

E D L N K V F P P E V A V F E P S E A E I S H T Q K A T
L V C L A T G F F P D H V E L S W W V N G K E V H S G V (SEQ ID NO: 101)

Figure 8c

E D L K N V F P P E V A V F E P S E A E I S H T Q K A T
L V C L A T G F Y P D H V E L S W W V N G K E V H S G V (SEQ ID NO: 102)

Figure 9

PEX954 gatctcgatcccgcgaaattaatacgactcactatagggagaccacaacggtttccctctagaaataatttgtttaactttaaga
aggagatataatcgatgtctaactcgagtgacaagtctgtctgcctattcaccgattttgattctcaaacaaatgtgtcacaaagt
aaggattctgatgtgtatatcacagacaaatgtgtgctagacatgaggtctatggacttcaagagcaacagtgctgtggcctg
gagcaacaaatctgactttgcatgtgcaaacgccttcaacaacagcattattccagaagacaccttcttccccagcccagaaa
gttcctaagcttgaattccgatccggctgctaacaaagcccgaaaggaagctgagttggctgctgccaccgctgagcaataa
ctagcataaccccttggggcctctaaacgggtcttgaggggttttttgctgaaaggaggaactatatccggataattcttgaag
acgaaagggcctcgtgatacgcctatttttataggttaatgtcatgataataatggtttcttagacgtgaggtggcactttcggg
gaaatgtgcgcggaacccctatttgtttatttttctaaatacattcaaatatgtatccgctcatgagacaataaccctgataaatgc
ttcaataatattttgttaaaattcgcgttaaattttgttaaatcagctcattttttaaccaataggccgaaatcggcaaaatcccttat
aaatcaaaagaatagaccgagatagggttgagtgttgttccagtttggaacaagagtccactattaaagaacgtggactccaa
cgtcaaagggcgaaaaaccgtctatcagggcgatggcccactacgtgaaccatcaccctaatcaagttttttggggtcgagg
tgccgtaaagcactaaatcggaacccaaagggagccccgatttagagcttgacggggaaagccggcgaacgtggcga
gaaaggaagggaagaaagcgaaaggagcgggcgctaggggcgctggcaagtgtagcggtcacgctgcgcgtaaccacc
acacccgccgcgcttaatgcgccgctacagggcgcgtcaggtggcactttcggggaaatgtgcgcggaacccctatttgtt
tattttctaaatacattcaaatatgtatccgctcatgagacaataaccctgataaatgcttcaataatattgaaaaaggaagagta
tgagtattcaacatttccgtgtcgcccttattccctttttgcggcattttgccttcctgttttgctcacccagaaacgctggtgaaa
gtaaaagatgctgaagatcagttgggtgcacgagtgggttacatcgaactggatctcaacagcggtaagatccttgagagttt
tcgccccgaagaacgttttccaatgatgagcacttttaaagttctgctatgtggcgcggtattatcccgtgttgacgccgggca
agagcaactcggtcgccgcatacactattctcagaatgacttggttgagtactcaccagtcacagaaaagcatcttacggatg
gcatgacagtaagagaattatgcagtgctgccataaccatgagtgataacactgcggccaacttacttctgacaacgatcgg
aggaccgaaggagctaaccgcttttttgcacaacatgggggatcatgtaactcgccttgatcgttgggaaccggagctgaat
gaagccataccaaacgacgagcgtgacaccacgatgcctgcagcaatggcaacaacgttgcgcaaactattaactggcga
actacttactctagcttcccggcaacaattaatagactggatggaggcggataaagttgcaggaccacttctgcgctcggcc
ttccggctggctggtttattgctgataaatctggagccggtgagcgtgggtctcgcggtatcattgcagcactggggccagat
ggtaagccctcccgtatcgtagttatctacacgacggggagtcaggcaactatggatgaacgaaatagacagatcgctgag
ataggtgcctcactgattaagcattggtaactgtcagaccaagtttactcatatatactttagattgatttaaaacttcatttttaattt
aaaaggatctaggtgaagatcctttttgataatctcatgaccaaaatcccttaacgtgagttttcgttccactgagcgtcagacc

Figure 9, cont.

ccgtagaaaagatcaaaggatcttcttgagatcctttttttctgcgcgtaatctgctgcttgcaaacaaaaaaaccaccgctacc
agcggtggtttgtttgccggatcaagagctaccaactctttttccgaaggtaactggcttcagcagagcgcagataccaaata
ctgtccttctagtgtagccgtagttaggccaccacttcaagaactctgtagcaccgcctacatacctcgctctgctaatcctgtt
accagtggctgctgccagtggcgataagtcgtgtcttaccgggttggactcaagacgatagttaccggataaggcgcagcg
gtcgggctgaacggggggttcgtgcacacagcccagcttggagcgaacgacctacaccgaactgagatacctacagcgt
gagctatgagaaagcgccacgcttcccgaagggagaaaggcggacaggtatccggtaagcggcagggtcggaacagg
agagcgcacgagggagcttccaggggaaacgcctggtatctttatagtcctgtcgggtttcgccacctctgacttgagcgt
cgatttttgtgatgctcgtcaggggggcggagcctatggaaaaacgccagcaacgcggcctttttacggttcctggccttttg
ctggccttttgctcacatgttctttcctgcgttatcccctgattctgtggataaccgtattaccgcctttgagtgagctgataccgct
cgccgcagccgaacgaccgagcgcagcgagtcagtgagcgaggaagcggaagagcgcctgatgcggtattttctccta
cgcatctgtgcggtatttcacaccgcaatggtgcactctcagtacaatctgctctgatgccgcatagttaagccagtatacact
ccgctatcgctacgtgactgggtcatggctgcgccccgacacccgccaacacccgctgacgcgccctgacgggcttgtct
gctcccggcatccgcttacagacaagctgtgaccgtctccgggagctgcatgtgtcagaggttttcaccgtcatcaccgaaa
cgcgcgaggcag (SEQ ID NO: 113)

Figure 10

PEX821
gatctcgatcccgcgaaattaatacgactcactatagggagaccacaacggtttccctctagaaataattttgtttaactttaaga
aggagatatacatatgaacgctggtgtcactcagacccccaaaattccaggtcctgaagacaggacagagcatgacactgca
gtgtgcccaggatatgaaccatgaatacatgtcctggtatcgacaagacccaggcatggggctgaggctgattcattactca
gttggtgctggtatcactgaccaaggagaagtccccaatggctacaatgtctccagatcaaccacagaggatttcccgctca
ggctgctgtcggctgctccctcccagacatctgtgtacttctgtgccagcaggccgggactagcgggagggcgaccagag
cagtacttcgggccgggcaccaggctcacggtcacagaggacctgaaaaacgtgttcccacccgaggtcgctgtgtttga
gccatcagaagcagagatctcccacacccaaaaggccacactggtgtgcctggccaccggtttctaccccgaccacgtgg
agctgagctggtgggtgaatgggaaggaggtgcacagtggggtctgcacagaccgcagccctcaaggagcagccg
ccctcaatgactccagatacgctctgagcagccgcctgagggtctcggccaccttctggcaggacccccgcaaccacttcc
gctgtcaagtccagtctacgggctctcggagaatgacgagtggacccaggataggccaaacccgtcacccagatcgtc
agcgccgaggcctggggtagagcagactaagcttgaattccgatccggctgctaacaaagcccgaaaggaagctgagttg
gctgctgccaccgctgagcaataactagcataaccccttggggcctctaaacgggtcttgaggggttttttgctgaaaggag
gaactatatccggataattcttgaagacgaaagggcctcgtgatacgcctatttttataggttaatgtcatgataataatggtttct
tagacgtcaggtggcactttcggggaaatgtgcgcggaacccctatttgtttatttttctaaatacattcaaatatgtatccgctc
atgagacaataaccctgataaatgcttcaataatatttgttaaaattcgcgttaaattttttgttaaatcagctcatttttaaccaata
ggccgaaatcggcaaaatcccttataaatcaaaagaatagaccgagataggtttgagtgttgttccagtttggaacaagagt
ccactattaaagaacgtggactccaacgtcaaaggcgaaaaaccgtctatcagggcgatggcccactacgtgaaccatca
ccctaatcaagttttttggggtcgaggtgccgtaaagcactaaatcggaaccctaaagggagccccgatttagagcttgac
ggggaaagccggcgaacgtggcgagaaaggaagggaagaaagcgaaaggagcgggcgctagggcgctggcaagtg
tagcggtcacgctgcgcgtaaccaccacacccgccgcgcttaatgcgccgctacagggcgcgtcaggtggcacttttcgg
ggaaatgtgcgcggaacccctatttgtttatttttctaaatacattcaaatatgtatccgctcatgagacaataaccctgataaatg
cttcaataatattgaaaaaggaagagtatgagtattcaacatttccgtgtcgcccttattcccttttttgcggcattttgccttcctgt
ttttgctcacccagaaacgctggtgaaagtaaaagatgctgaagatcagttgggtgcacgagtgggttacatcgaactggat
ctcaacagcggtaagatccttgagagttttcgccccgaagaacgttttccaatgatgagcacttttaaagttctgctatgtggcg
cggtattatcccgtgttgacgccgggcaagagcaactcggtcgccgcatacactattctcagaatgacttggttgagtactca
ccagtcacagaaaagcatcttacggatggcatgacagtaagagaattatgcagtgctgccataaccatgagtgataacactg
cggccaacttacttctgacaacgatcggaggaccgaaggagctaaccgcttttttgcacaacatgggggatcatgtaactcg
ccttgatcgttgggaaccggagctgaatgaagccataccaaacgacgagcgtgacaccacgatgcctgcagcaatggcaa
caacgttgcgcaaactattaactggcgaactacttactctagcttcccggcaacaattaatagactggatggaggcggataaa
gttgcaggaccacttctgcgctcggcccttccggctggctggtttattgctgataaatctggagccggtgagcgtgggtctcg
cggtatcattgcagcactggggccagatggtaagccctcccgtatcgtagttatctacacgacggggagtcaggcaactatg
gatgaacgaaatagacagatcgctgagataggtgcctcactgattaagcattggtaactgtcagaccaagtttactcatatata
ctttagattgatttaaaacttcattttaatttaaaaggatctaggtgaagatcctttttgataatctcatgaccaaaatcccttaacgt
gagttttcgttccactgagcgtcagaccccgtagaaaagatcaaaggatcttcttgagatcctttttttctgcgcgtaatctgctg
cttgcaaacaaaaaaaccaccgctaccagcggtggtttgtttgccggatcaagagctaccaactctttttccgaaggtaactg
gcttcagcagagcgcagataccaaatactgtccttctagtgtagccgtagttaggccaccacttcaagaactctgtagcaccg
cctacatacctcgctctgctaatcctgttaccagtggctgctgccagtggcgataagtcgtgtcttaccgggttggactcaaga
cgatagttaccggataaggcgcagcggtcgggctgaacggggggttcgtgcacacagcccagcttggagcgaacgacct
acaccgaactgagatacctacagcgtgagctatgagaaagcgccacgcttcccgaagggagaaaggcggacaggtatcc
ggtaagcggcagggtcggaacaggagagcgcacgagggagcttccaggggaaacgcctggtatctttatagtcctgtc
gggtttcgccacctctgacttgagcgtcgatttttgtgatgctcgtcaggggggcggagcctatggaaaaacgccagcaacg

Figure 10, cont.

cggccttttttacggttcctggcctttttgctggcctttttgctcacatgttctttcctgcgttatcccctgattctgtggataaccgtatta
ccgcctttgagtgagctgataccgctcgccgcagccgaacgaccgagcgcagcgagtcagtgagcgaggaagcggaag
agcgcctgatgcggtattttctccttacgcatctgtgcggtatttcacaccgcaatggtgcactctcagtacaatctgctctgatg
ccgcatagttaagccagtatacactccgctatcgctacgtgactgggtcatggctgcgccccgacacccgccaacacccgc
tgacgcgccctgacgggcttgtctgctcccggcatccgcttacagacaagctgtgaccgtctccgggagctgcatgtgtcag
aggttttcaccgtcatcaccgaaacgcgcgaggcag
(SEQ ID NO: 114)

Figure 11 pEX202 gatctcgatcccgcgaaattaatacgactcactatagggagaccacaacggtttccctctagaaataattttgtttaactttaaga
aggagatatacatatgcagaaggaagtggagcagaactctggaccctcagtgttccagagggagccattgcctctctcaa
ctgcacttacagtgaccgaggttcccagtccttcttctggtacagacaatatctgggaaaagccctgagttgataatgtccata
tactccaatggtgacaaagaagatggaaggtttacagcacagctcaataaagccagccagtatgtttctctgctcatcagaga
ctcccagcccagtgattcagccacctacctctgtgccgttacaactgacagctgggggaaattgcagtttggagcagggacc
caggttgtggtcaccccagatatccagaaccctgaccctgccgtgtaccagctgagagactctaaatccagtgacaagtctg
tctgcctattcaccgattttgattctcaaacaaatgtgtcacaaagtaaggattctgatgtgtatatcacagacaaaactgtgcta
gacatgaggtctatggacttcaagagcaacagtgctgtggcctggagcaacaaatctgactttgcatgtgcaaacgccttca
acaacagcattattccagaagacaccttcttccccagcccagaaagttccccggggggtagaatcgcccggctggaggaa
aaagtgaaaaccttgaaagctcagaactcggagctggcgtccacggccaacatgctcagggaacaggtggcacagcttaa
acagaaagtcatgaactactaggatccatggtaagcttgaattccgatccggctgctaacaaagcccgaaaggaagctgag
ttggctgctgccaccgctgagcaataactagcataacccttggggcctctaaacgggtcttgaggggttttttgctgaaagg
aggaactatatccggataattcttgaagacgaaagggcctcgtgatacgcctatttttataggttaatgtcatgataataatggtt
tcttagacgtcaggtggcactttcggggaaatgtgcgcggaacccctatttgtttatttttctaaatacattcaaatatgtatccg
ctcatgagacaataaccctgataaatgcttcaataatatattttgttaaaattcgcgttaaattttgttaaatcagctcatttttaacca
ataggccgaaatcggcaaaatcccttataaatcaaaagaatagaccgagatagggttgagtgttgttccagtttggaacaaga
gtccactattaaagaacgtggactccaacgtcaaagggcgaaaaaccgtctatcagggcgatggcccactacgtgaaccat
caccctaatcaagttttttggggtcgaggtgccgtaaagcactaaatcggaacctaaagggagcccccgatttagagcttg
acggggaaagccggcgaacgtggcgagaaaggaagggaagaaagcgaaaggagcgggcgctagggcgctggcaag
tgtagcggtcacgctgcgcgtaaccaccacacccgccgcgcttaatgcgccgctacagggcgcgtcaggtggcactttcg
gggaaatgtgcgcggaacccctatttgtttatttttctaaatacattcaaatatgtatccgctcatgagacaataaccctgataaat
gcttcaataatattgaaaaaggaagagtatgagtattcaacatttccgtgtcgcccttattcccttttttgcggcatttttgccttcct
gtttttgctcacccagaaacgctggtgaaagtaaaagatgctgaagatcagttgggtgcacgagtgggttacatcgaactgg
atctcaacagcggtaagatccttgagagttttcgccccgaagaacgttttccaatgatgagcacttttaaagttctgctatgtgg
cgcggtattatcccgtgttgacgccgggcaagagcaactcggtcgccgcatacactattctcagaatgacttggttgagtact
caccagtcacagaaaagcatcttacggatggcatgacagtaagagaattatgcagtgctgccataaccatgagtgataacac
tgcggccaacttacttctgacaacgatcggaggaccgaaggagctaaccgcttttttgcacaacatgggggatcatgtaact
cgccttgatcgttgggaaccggagctgaatgaagccataccaaacgacgagcgtgacaccacgatgcctgcagcaatggc
aacaacgttgcgcaaactattaactggcgaactacttactctagcttcccggcaacaattaatagactggatggaggcggata
aagttgcaggaccacttctgcgctcggcccttccggctggctggtttattgctgataaatctggagccggtgagcgtgggtct
cgcggtatcattgcagcactggggccagatggtaagccctcccgtatcgtagttatctacacgacggggagtcaggcaact
atggatgaacgaaatagacagatcgctgagataggtgcctcactgattaagcattggtaactgtcagaccaagtttactcatat
atactttagattgatttaaaacttcatttttaatttaaaaggatctaggtgaagatcctttttgataatctcatgaccaaaatcccttaa
cgtgagttttcgttccactgagcgtcagaccccgtagaaaagatcaaaggatcttcttgagatcctttttttctgcgcgtaatctg
ctgcttgcaaacaaaaaaaccaccgctaccagcggtggtttgtttgccggatcaagagctaccaactctttttccgaaggtaa
ctggcttcagcagagcgcagataccaaatactgtccttctagtgtagccgtagttaggccaccacttcaagaactctgtagca
ccgcctacatacctcgctctgctaatcctgttaccagtggctgctgccagtggcgataagtcgtgtcttaccgggttggactca
agacgatagttaccggataaggcgcagcggtcgggctgaacggggggttcgtgcacacagcccagcttggagcgaacg
acctacaccgaactgagatacctacagcgtgagctatgagaaagcgccacgcttcccgaagggagaaaggcggacaggt
atccggtaagcggcagggtcggaacaggagagcgcacgagggagcttccagggggaaacgcctggtatctttatagtcct
gtcgggtttcgccacctctgacttgagcgtcgatttttgtgatgctcgtcaggggggcggagcctatggaaaaacgccagca
acgcggcctttttacggttcctggccttttgctggccttttgctcacatgttctttcctgcgttatcccctgattctgtggataaccgt

Figure 11, cont.

attaccgcctttgagtgagctgataccgctcgccgcagccgaacgaccgagcgcagcgagtcagtgagcgaggaagcgg
aagagcgcctgatgcggtattttctccttacgcatctgtgcggtatttcacaccgcaatggtgcactctcagtacaatctgctct
gatgccgcatagttaagccagtatacactccgctatcgctacgtgactgggtcatggctgcgccccgacaccegccaacac
ccgctgacgcgccctgacgggcttgtctgctcccggcatccgcttacagacaagctgtgaccgtctccgggagctgcatgt
gtcagaggttttcaccgtcatcaccgaaacgcgcgaggcag
(SEQ ID NO: 115)

Figure 12 pEX205 gatctcgatcccgcgaaattaatacgactcactatagggagaccacaacggtttccctctagaaataattttgtttaactttaagaaggagat
atacatatgaacgctggtgtcactcagaccccaaaattccaggtcctgaagacaggacagagcatgacactgcagtgtgcccaggatat
gaaccatgaatacatgtcctggtatcgacaagacccaggcatggggctgaggctgattcattactcagttggtgctggtatcactgacca
aggagaagtccccaatggctacaatgtctccagatcaaccacagaggatttccc gctcaggctgctgtcggctgctccctcccagacat
ctgtgtacttctgtgccagcaggccgggactagcgggagggcgaccagagcagtacttcgggccgggcaccaggctcacggtcaca
gaggacctgaaaaacgtgttcccacccgaggtcgctgtgtttgagccatcagaagcagagatctcccacacccaaaaggccacactgg
tgtgcctggccacaggcttctaccccgaccacgtggagctgagctggtgggtgaatgggaaggaggtgcacagtggggtcagcaca
gacccgcagcccctcaaggagcagcccgccctcaatgactccagatacgctctgagcagccgcctgagggtctcggccaccttctgg
caggaccccgcaaccacttccgctgtcaagtccagttctacgggctctcggagaatgacgagtggacccaggataggccaaaccc
gtcacccagatcgtcagcgccgaggcctggggtagagcagaccccggggtctgactgatacactccaagcggagacagatcaactt
gaagacaagaagtctgcgttgcagaccgagattgccaatctactgaaagagaaggaaaaactagagttcatcctggcagcttacggatc
cggtggtggtctgaacgatattttt gaagctcagaaaatcgaatggcattaagcttgaattccgatccggctgctaacaaagcccgaaag
gaagctgagttggctgctgccaccgctgagcaataactagcataacccc ttgggg cctctaaacgggtcttgagggg ttttttgctgaaa
ggaggaactatatccggataattcttgaagacgaaagggcctcgtgatacgcctattttataggttaatgtcatgataataatggtttcttag
acgtcaggtggcacttttcggggaaatgtgcgcggaaccccta tttgttta ttttt ctaaatacattcaaatatgtatccgctcatgagacaat
aaccctgataaatgcttcaataatatttt gttaaaattcgcgttaaattttt gttaaatcagctcatttttta accaataggccgaaatcggcaaa
atcccttataaatcaaaagaatagaccgagatagggttgagtgttgttccagtttggaacaagagtccactattaaagaacgtggactcca
acgtcaaagggcgaaaaaccgtctatcagggcgatggcccactacgtgaaccatcaccctaatcaagttttttgggg tcgaggtgccgt
aaagcactaaatcggaacccta aagggagccccc gatttagagcttgacggggaaagccggcgaacgtggcgagaaaggaaggga
agaaagcgaaaggagcgggcgctagggcgctggcaagtgtagcggtcacgctgcgcgtaaccaccacacccgccgcgcttaatgc
gccgctacagggcgcgtcaggtggcacttttcggggaaatgtgcgcggaaccccta tttgttta ttttt ctaaatacattcaaatatgtatcc
gctcatgagacaataaccctgataaatgcttcaataatattgaaaaaggaagagtatgagtattcaacatttccgtgtcgcccttattccctt
tttt gcggcattttgccttcctgtttttgctcacccagaaacgctggtgaaagtaaaagatgctgaagatcagttgggtgcacgagtgggtta
catcgaactggatctcaacagcggtaagatccttgagagttttcgccccgaagaacgttttccaatgatgagcacttttaaagttctgctatg
tggcgcggtattatcccgtgttgacgccgggcaagagcaactcggtcgccgcatacactattctcagaatgacttggttgagtactcacc
agtcacagaaaagcatcttacggatggcatgacagtaagagaattatgcagtgctgccataaccatgagtgataacactgcggccaactt
acttctgacaacgatcggaggaccgaaggagctaaccgcttttttgcacaacatgggggatcatgtaactcgccttgatcgttgggaacc
ggagctgaatgaagccataccaaacgacgagcgtgacaccacgatgcctgcagcaatggcaacaacgttgcgcaaactattaactgg
cgaactacttactctagcttcccggcaacaattaatagactggatgg aggcggataaagttgcaggaccacttctgcgctcggcccttcc
ggctggctggtttattgctgataaatctggagccggtgagcgtgggtctcgcggtatcattgcagcactggggccagatggtaagccctc
ccgtatcgtagttatctacacgacggggagtcaggcaactatggatgaacgaaatagacagatcgctgagataggtgcctcactgattaa
gcattggtaactgtcagaccaagtttactcatatatactttagattgatttaaaacttcatttttaatttaaaaggatctaggtgaagatccttttg
ataatctcatgaccaaaatcccttaacgtgagttttcgttccactgagcgtcagaccccgtagaaaagatcaaaggatcttcttgagatcctt
ttttt ctgcgcgtaatctgctgcttgcaaacaaaaaaccaccgctaccagcggtggtttgtttgccggatcaagagctaccaactctttttc
cgaaggtaactggcttcagcagagcgcagataccaaatactgtccttctagtgtagccgtagttaggccaccacttcaagaactctgtag
caccgcctacatacctcgctctgctaatcctgttaccagtggctgctgccagtggcgataagtcgtgtcttaccgggttggactcaagacg
atagttaccggataaggcgcagcggtcgggctgaacggggggttcgtgcacacagcccagcttggagcgaacgacctacaccgaac
tgagatacctacagcgtgagctatgagaaagcgccacgcttcccgaagggagaaaggcggacaggtatccggtaagcggcagggtc
ggaacaggagagcgcacgagggagcttccagggggaaacgcctggtatctttatagtcctgtcgggtttcgccacctctgacttgagc
gtcgatttttgtgatgctcgtcaggggggcggagcctatggaaaaacgccagcaacgcggcctttttacggttcctggccttttgctggcc
ttttgctcacatgttctttcctgcgttatcccctgattctgtggataaccgtattaccgcctttgagtgagctgataccgctcgccgcagccga
acgaccgagcgcagcgagtcagtgagcgaggaagcggaagagcgcctgatgcggtattttctccttacgcatctgtgcggtatttcaca
ccgcaatggtgcactctcagtacaatctgctctgatgccgcatagttaagccagtatacactccgctatcgctacgtgactgggtcatggc
tgcgccccgacacccgccaacacccgctgacgcgccctgacgggcttgtctgctcccggcatccgcttacagacaagctgtgaccgtc
tccgggagctgcatgtgtcagaggttttcaccgtcatcaccgaaacgcgcgaggcag (SEQ ID NO: 116)

Figure 13

MGVTQTPKFQVLKTGQSMTLQCAQDMNHEYMSWYRQ
DPGMGLRLIHYSV<u>AIQT</u>TDQGEVPNGYNVSRST<u>I</u>EDFPL
RLLSAAPSQTSVYFCASSYVG<u>D</u>TGELFFGEGSRLTVL
(SEQ ID No: 117)

MGVTQTPKFQVLKTGQSMTLQCAQDMNHEYMSWYRQ
DPGMGLRLIHYSV<u>AIQT</u>TD<u>R</u>GEVPNGYNVSRST<u>I</u>EDFPL
RLLSAAPSQTSVYFCASSY<u>L</u>GNTGELFFGEGSRLTVL
(SEQ ID No: 118)

MGVTQTPKFQVLKTGQSMTLQCAQDMNHEYMSWYRQ
DPGMGLRLIHYSV<u>AIQT</u>TDQGEVPNGYNVSRST<u>I</u>EDFPL
RLLSAAPSQTSVYFCASSYVGNTGELFFGEGSRLTVL
(SEQ ID No: 119)

MGVTQTPKFQVLKTGQSMTLQCAQDMNHEYMSWYRQ
DPGMGLRLIHYSV<u>SV</u>G<u>M</u>TD<u>R</u>GEVPNGYNVSRSTTEDFP
LRLLSAAPSQTSVYFCASSYVG<u>D</u>TGELFFGEGSRLTVL
(SEQ ID No: 120)

MGVTQTPKFQVLKTGQSMTLQCAQDMNHEYMSWYRQ
DPGMGLRLIHYSV<u>AIQT</u>TD<u>R</u>GEVPNGYNVSRST<u>I</u>EDFPL
RLLSAAPSQTSVYFCASSYVGNTGELFFGEGSRLTVL
(SEQ ID No: 121)

Figure 14a

C58c61 alpha with TRAC

MKQEVTQIPAALSVPEGENLVLNCSFTDSAIYNLQWFR
QDPGKGLTSLLLI<u>TPW</u>QREQTSGRLNASLDKSSGRSTLY
IAASQPGDSATYLCAVRP<u>LLD</u>G<u>T</u>YIPTFGRGTSLIVHPYI
QNPDPAVYQLRDSKSSDKSVCLFTDFDSQTNVSQSKDS
DVYITDK (SEQ ID NO: 122)

Figure 14b

C58c61 beta with TRBC1

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRLLSAAPSQTSVYFCASSY<u>L</u>GNTGELFFGEGSRLTVL
EDLNKVFPPEVAVFEPSEAEISHTQKATLVCLATGFFPD
HVELSWWVNGKEVHSGV (SEQ ID NO: 123)

Figure 14c

C58c61 beta with TRBC2

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRLLSAAPSQTSVYFCASSY<u>L</u>GNTGELFFGEGSRLTVL
EDLKNVFPPEVAVFEPSEAEISHTQKATLVCLATGFYPD
HVELSWWVNGKEVHSGV (SEQ ID NO: 124)

Figure 14d

C58c61 beta with TRBC2 fused to wt human IL-2

MNAGVTQTPKFQVLKTGQSMTLQCAQDMNHEYMSWY
RQDPGMGLRLIHYSV<u>AIQT</u>TDQGEVPNGYNVSRST<u>I</u>EDF
PLRLLSAAPSQTSVYFCASSY<u>L</u>GNTGELFFGEGSRLTVL
EDLKNVFPPEVAVFEPSEAEISHTQKATLVCLATGFYPD
HVELSWWVNGKEVHSGV*PGAPTSSSTKKTQLQLEHLLL*
*DLQMILNGINNYKNPKLTRMLTFKFYMPKKATELKHLQCL*
*EEELKPLEEVLNLAQSKNFHLRPRDLISNINVIVLELKGSE*
*TTFMCEYADETATIVEFLNRWITFCQSIISTLT*

(SEQ ID NO: 125)

HIGH AFFINITY NY-ESO T CELL RECEPTORS

This application is a division of Ser. No. 11/596,458 filed on Nov. 13, 2006 as a national stage application of PCT/GB2005/001924 filed on May 18, 2005. PCT/GB2005/001824 claims the benefit of GB 0411123.3 filed on May 19, 2004 and GB 0419643.2 filed on Sep. 3, 2004.

This application incorporates by reference the contents of a 145 kb text file created on Sep. 30, 2010 and named "12854691_sequence_listing.txt," which is the sequence listing for this application.

The present invention relates to T cell receptors (TCRs) having the property of binding to SLLMWITQC (SEQ ID NO:126)-HLA-A*0201 and comprising at least one TCR α chain variable domain and/or at least one TCR β chain variable domain CHARACTERISED IN THAT said TCR has a $K_{off}$ for the said SLLMWITQC (SEQ ID NO:126)-HLA-A*0201 complex of less than or equal to 1 μM and/or has an off-rate ($k_{off}$) for the SLLMWITQC (SEQ ID NO:126)-HLA-A*0201 complex of $1 \times 10^{-3}$ $S^{-1}$ or slower.

BACKGROUND TO THE INVENTION

The SLLMWITQC (SEQ ID NO:126) peptide is derived from the NY-ESO-I protein that is expressed by a range of tumours (Chen et al., (1997) *PNAS USA* 94 1914-1918). The Class I HLA molecules of these cancerous cells present peptides from this protein, including SLLMWITQC (SEQ ID NO:126). Therefore, the SLLMWITQC (SEQ ID NO:126)-HLA-A2 complex provides a cancer marker that TCRs can target, for example for the purpose of delivering cytotoxic or immuno-stimulatory agents to the cancer cells. However, for that purpose it would be desirable if the TCR had a higher affinity and/or a slower off-rate for the peptide-HLA complex than native TCRs specific for that complex.

BRIEF DESCRIPTION OF THE INVENTION

This invention makes available for the first time TCRs having high affinity ($K_D$) of the interaction less than or equal to 1 μM, and/or a slower off-rate ($k_{off}$) of $1 \times 10^{-3}$ $S^{-1}$ or slower, for the SLLMWITQC (SEQ ID NO:126)-HLA-A*0201 complex. Such TCRs are useful, either alone or associated with a therapeutic agent, for targeting cancer cells presenting that complex.

DETAILED DESCRIPTION OF THE INVENTION

The present invention provides a T-cell receptor (TCR) having the property of binding to SLLMWITQC (SEQ ID NO:126)-HLA-A*0201 and comprising at least one TCR α chain variable domain and/or at least one TCR β chain variable domain CHARACTERISED IN THAT said TCR has a $K_D$ for the said SLLMWITQC (SEQ ID NO:126)-HLA-A*0201 complex of less than or equal to 1 μM and/or has an off-rate ($k_{off}$) for the SLLMWITQC (SEQ ID NO:126)-HLA-A*0201 complex of $1 \times 10^{-3}$ $S^{-1}$ or slower. The $K_D$ and/or ($k_{off}$) measurement can be made by any of the known methods. A preferred method is the Surface Plasmon Resonance (Biacore) method of Example 5.

For comparison, the interaction of a disulfide-linked soluble variant of the native 1G4 TCR (see SEQ ID NO: 9 for TCR α chain and SEQ ID NO: 10 for TCR β chain) and the SLLMWITQC-HLA-A*0201 complex has a KD of approximately 10 μM, an off-rate ($k_{off}$) of $1.28 \times 10^{-1}$ $S^{-1}$ and a half-life of 0.17 minutes as measured by the Biacore-base method of Example 5.

The native 1G4 TCR specific for the SLLMWITQC (SEQ ID NO:126)-HLA-A*0201 complex has the following Valpha chain and Vbeta chain gene usage:
Alpha chain—TRA V21
Beta chain:—TRBV 6.5

The native 1G4 TCR can be used as a template into which various mutations that impart high affinity and/or a slow off-rate for the interaction between TCRs of the invention and the SLLMWITQC (SEQ ID NO:126)-HLA-A*0201 complex can be introduced. Thus the invention includes TCRs which are mutated relative to the native 1G4 TCR α chain variable domain (see FIG. 1a and SEQ ID No: 1) and/or β chain variable domain (see FIG. 1b and SEQ ID NO: 2) in at least one complementarity determining region (CDR) and/or variable domain framework region thereof. It is also contemplated that other hypervariable regions in the variable domains of the TCRs of the invention, such as the hypervariable 4 (HV4) regions, may be mutated so as to produce a high affinity mutant.

Native TCRs exist in heterodimeric αβ or γδ forms. However, recombinant TCRs consisting of a single TCR α or TCR β chain have previously been shown to bind to peptide MHC molecules.

In one embodiment the TCR of the invention comprise both an α chain variable domain and an TCR β chain variable domain.

As will be obvious to those skilled in the art the mutation(s) in the TCR α chain sequence and/or TCR β chain sequence may be one or more of substitution(s), deletion(s) or insertion(s). These mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see (Sambrook & Russell, (2001) Molecular Cloning—A Laboratory Manual ($3^{rd}$ Ed.) CSHL Press) Further information on LIC procedures can be found in (Rashtchian, (1995) *Curr Opin Biotechnol* 6 (1): 30-6)

It should be noted that any αβ TCR that comprises similar Valpha and Vbeta gene usage and therefore amino acid sequence to that of the 1G4 TCR could make a convenient template TCR. It would then be possible to introduce into the DNA encoding one or both of the variable domains of the template αβ TCR the changes required to produce the mutated high affinity TCRs of the invention. As will be obvious to those skilled in the art, the necessary mutations could be introduced by a number of methods, for example site-directed mutagenesis.

The TCRs of the invention include those in which one or more of the TCR alpha chain variable domain amino acids corresponding to those listed below are mutated relative to the amino acid occurring at these positions in the sequence provided for the native 1G4 TCR alpha chain variable domain in FIG. 1a and SEQ ID No: 1.

Unless stated to the contrary, the TCR amino acid sequences herein are generally provided including an N-terminal methionine (Met or M) residue. As will be known to those skilled in the art this residue may be removed during the production of recombinant proteins. Furthermore, unless stated to the contrary, the soluble TCR and TCR variable domain sequences have been truncated at the N-terminus thereof (Resulting in the lose of the N-terminal "K" and "NA"

in the TCR alpha and beta chain sequences respectively). As will be obvious to those skilled in the art these "missing" N-terminal TCR residues may be re-introduced into the TCRs of the present invention. As will also be obvious to those skilled in the art, it may be possible to truncate the sequences provided at the C-terminus and/or N-terminus thereof, by 1, 2, 3, 4, 5 or more residues, without substantially affecting the pMHC binding characteristics of the TCR, all such trivial variants are encompassed by the present invention.

As used herein the term "variable domain" is understood to encompass all amino acids of a given TCR which are not included within the constant domain as encoded by the TRAC gene for TCR α chains and either the TRBC1 or TRBC2 for TCR β chains. (T cell receptor Factsbook, (2001) LeFranc and LeFranc, Academic Press, ISBN 0-12-441352-8)

As is known to those skilled in the art, part of the diversity of the TCR repertoire is due to variations which occur in the amino acid encoded by the codon at the boundary between the variable domain, as defined herein, and the constant domain. For example, the codon that is present at this boundary in the wild-type 1G4 TCR sequence results in the presence of the Tyrosine (Y) residue at the C-terminal of the variable domain sequences herein. This Tyrosine replaces the N-terminal Asparagine (N) residue encoded by the TRAC gene shown in FIG. 8A.

Embodiments of the invention include mutated TCRs which comprise mutation of one or more of alpha chain variable domain amino acids corresponding to: 20V, 51Q, 52S, 53S, 94P, 95T, 96S, 97G, 98G, 99S, 100Y, 101I and 103T, for example the amino acids:

20A
51P/S/T or M
52P/F or G
53W/H or T
94H or A
95L/M/A/Q/Y/E/I/F/V/N/G/S/D or R
96L/T/Y/I/Q/V/E/X/A/W/R/G/H/D or K
97D/N/V/S/T or A
98P/H/S/T/W or A
99T/Y/D/H/V/N/E/G/Q/K/A/I or R
100F/M or D
101P/T/ or M
103A

The numbering used above is the same as that shown in FIG. 1a and SEQ ID No: 1

Embodiments of the invention also include TCRs which comprise mutation of one or more of the TCR beta chain variable domain amino acids corresponding to those listed below, are relative to the amino acid occurring at these positions in the sequence provided for the native 1G4 TCR alpha chain variable domain of the native 1G4 TCR beta chain in FIG. 1b and SEQ ID No: 2. The amino acids referred to which may be mutated are: 18M, 50G, 51A, 52G, 53I, 55D, 56Q, 70T, 94Y, 95V and 97N, for example:

18V
50S or A
51V or I
52Q
53T or M
55R
56R
70I
94N or F
95L
97G or D

The numbering used above is the same as that shown in FIG. 1b and SEQ ID No: 2

Further preferred embodiments of the invention are provided by TCRs comprising one of the mutated alpha chain variable domain amino acid sequences shown in FIG. 6 (SEQ ID Nos: 11 to 83). Phenotypically silent variants of such TCRs also form part of this invention.

Additional preferred embodiments of the invention are provided by TCRs comprising one of the mutated beta chain variable domain amino acid sequences shown in FIG. 7 or 13. (SEQ ID Nos: 84 to 99 or 117 to 121). Phenotypically silent variants of such TCRs also form part of this invention.

Native TCRs exist in heterodimeric αβ or γδ forms. However, recombinant TCRs consisting of αα or ββ homodimers have previously been shown to bind to peptide MHC molecules. Therefore, one embodiment of the invention is provided by TCR αα or TCR ββ homodimers.

Further preferred embodiments are provided by TCRs of the invention comprising the alpha chain variable domain amino acid sequence and the beta chain variable domain amino acid sequence combinations listed below, phenotypically silent variants of such TCRs also form part of this invention:

| Alpha chain variable domain sequence, SEQ ID NO: | Beta chain variable domain sequence, SEQ ID NO: |
|---|---|
| 1 | 84 |
| 1 | 85 |
| 1 | 86 |
| 1 | 87 |
| 1 | 88 |
| 11 | 84 |
| 12 | 84 |
| 12 | 85 |
| 12 | 90 |
| 11 | 85 |
| 11 | 86 |
| 11 | 92 |
| 11 | 93 |
| 13 | 86 |
| 14 | 84 |
| 14 | 85 |
| 15 | 84 |
| 15 | 85 |
| 16 | 84 |
| 16 | 85 |
| 17 | 86 |
| 18 | 86 |
| 19 | 84 |
| 20 | 86 |
| 21 | 84 |
| 21 | 85 |
| 22 | 84 |
| 23 | 86 |
| 24 | 84 |
| 25 | 84 |
| 26 | 84 |
| 27 | 84 |
| 28 | 84 |
| 29 | 84 |
| 30 | 84 |
| 31 | 84 |
| 32 | 84 |
| 33 | 84 |
| 20 | 86 |
| 34 | 86 |
| 35 | 89 |
| 36 | 89 |
| 37 | 89 |
| 38 | 89 |
| 39 | 89 |
| 16 | 89 |
| 17 | 89 |
| 31 | 89 |

| Alpha chain variable domain sequence, SEQ ID NO: | Beta chain variable domain sequence, SEQ ID NO: |
|---|---|
| 40 | 89 |
| 1 | 90 |
| 1 | 91 |
| 41 | 90 |
| 42 | 2 |
| 42 | 85 |
| 42 | 92 |
| 1 | 92 |
| 1 | 93 |
| 43 | 92 |
| 44 | 92 |
| 45 | 92 |
| 46 | 92 |
| 47 | 92 |
| 48 | 84 |
| 49 | 94 |
| 50 | 84 |
| 50 | 94 |
| 51 | 94 |
| 51 | 95 |
| 1 | 94 |
| 1 | 85 |
| 51 | 84 |
| 52 | 84 |
| 52 | 94 |
| 52 | 95 |
| 53 | 84 |
| 49 | 95 |
| 49 | 94 |
| 54 | 92 |
| 55 | 92 |
| 56 | 92 |
| 57 | 92 |
| 58 | 92 |
| 59 | 92 |
| 60 | 92 |
| 61 | 92 |
| 62 | 92 |
| 63 | 92 |
| 64 | 92 |
| 65 | 92 |
| 66 | 92 |
| 67 | 92 |
| 68 | 92 |
| 69 | 92 |
| 70 | 92 |
| 71 | 92 |
| 72 | 92 |
| 73 | 92 |
| 74 | 92 |
| 75 | 92 |
| 76 | 92 |
| 77 | 92 |
| 78 | 92 |
| 79 | 92 |
| 80 | 92 |
| 81 | 92 |
| 82 | 92 |
| 83 | 92 |
| 11 | 96 |
| 11 | 97 |
| 11 | 98 |
| 11 | 99 |
| 1 | 89 |
| 50 | 117 |
| 49 | 117 |
| 50 | 118 |
| 49 | 119 |
| 50 | 119 |
| 58 | 93 |
| 49 | 118 |
| 1 | 119 |
| 1 | 117 |
| 55 | 120 |
| 56 | 120 |
| 50 | 121 |
| 50 | 120 |
| 49 | 121 |
| 49 | 120 |
| 48 | 118 |
| 53 | 95 |

Preferred embodiments provide a TCR of the invention comprising:

the alpha chain variable domain shown in the SEQ E) NO: 49 and the beta chain variable domain shown in the SEQ ID NO: 94, or phenotypically silent variants thereof.

In another preferred embodiment TCRs of the invention comprising the variable domain combinations detailed above further comprise the alpha chain constant region amino acid sequence shown in FIG. 8a (SEQ ID NO: 100) and one of the beta chain amino acid constant region sequences shown in FIGS. 8b and 8c (SEQ ID NOs: 101 and 102) or phenotypically silent variants thereof.

As used herein the term "phenotypically silent variants" is understood to refer to those TCRs which have a KD for the said SLLMWITQC (SEQ ID NO:126)-HLA-A*0201 complex of less than or equal to 1 µM and/or have an off-rate ($k_{off}$) of $1 \times 10^{-3}$ $S^{-1}$ or slower. For example, as is known to those skilled in the art, it may be possible to produce TCRs that incorporate minor changes in the constant and/or variable domains thereof compared to those detailed above without altering the affinity and/or off-rate for the interaction with the SLLMWITQC (SEQ ID NO:126)-HLA-A*0201 complex. Such trivial variants are included in the scope of this invention. Those TCRs in which one or more conservative substitutions have been made also form part of this invention.

In one broad aspect, the TCRs of the invention are in the form of either single chain TCRs (scTCRs) or dimeric TCRs (dTCRs) as described in WO 04/033685 and WO 03/020763.

A suitable scTCR form comprises a first segment constituted by an amino acid sequence corresponding to a TCR α chain variable domain, a second segment constituted by an amino acid sequence corresponding to a TCR β chain variable domain sequence fused to the N terminus of an amino acid sequence corresponding to a TCR β chain constant domain extracellular sequence, and a linker sequence linking the C terminus of the first segment to the N terminus of the second segment.

Alternatively the first segment may be constituted by an amino acid sequence corresponding to a TCR β chain variable domain, the second segment may be constituted by an amino acid sequence corresponding to a TCR α chain variable domain sequence fused to the N terminus of an amino acid sequence corresponding to a TCR α chain constant domain extracellular sequence.

The above scTCRs may further comprise a disulfide bond between the first and second chains, said disulfide bond being one which has no equivalent in native αβT cell receptors, and wherein the length of the linker sequence and the position of the disulfide bond being such that the variable domain sequences of the first and second segments are mutually orientated substantially as in native αβ T cell receptors.

More specifically the first segment may be constituted by an amino acid sequence corresponding to a TCR α chain variable domain sequence fused to the N terminus of an amino acid sequence corresponding to a TCR α chain constant domain extracellular sequence, the second segment may be constituted by an amino acid sequence corresponding to a TCR β chain variable domain fused to the N terminus of an amino acid sequence corresponding to TCR β chain constant domain extracellular sequence, and a disulfide bond may be provided between the first and second chains, said disulfide bond being one which has no equivalent in native αβ T cell receptors.

In the above scTCR forms, the linker sequence may link the C terminus of the first segment to the N terminus of the second segment, and may have the formula -PGGG-(SGGGG)$_n$-P- wherein n is 5 or 6 and P is proline, G is glycine and S is serine.

```
                                              (SEQ ID NO: 103)
-PGGG-SGGGGSGGGGSGGGGSGGGGSGGGG-P (SEQ ID NO: 104)
-PGGG-SGGGGSGGGGSGGGGSGGGGSGGGGSGGGG-P
```

A suitable dTCR form of the TCRs of the present invention comprises a first polypeptide wherein a sequence corresponding to a TCR α chain variable domain sequence is fused to the N terminus of a sequence corresponding to a TCR α chain constant domain extracellular sequence, and a second polypeptide wherein a sequence corresponding to a TCR β chain variable domain sequence fused to the N terminus a sequence corresponding to a TCR β chain constant domain extracellular sequence, the first and second polypeptides being linked by a disulfide bond which has no equivalent in native αβ T cell receptors.

The first polypeptide may comprise a TCR α chain variable domain sequence is fused to the N terminus of a sequence corresponding to a TCR α chain constant domain extracellular sequence, and a second polypeptide wherein a sequence corresponding to a TCR β chain variable domain sequence is fused to the N terminus a sequence corresponding to a TCR β chain constant domain extracellular sequence, the first and second polypeptides being linked by a disulfide bond between cysteine residues substituted for Thr 48 of exon 1 of TRAC*01 and Ser 57 of exon 1 of TRBC1*01 or TRBC2*01 or the non-human equivalent thereof. ("TRAC" etc. nomenclature herein as per T cell receptor Factsbook, (2001) LeFranc and LeFranc, Academic Press, ISBN 0-12-441352-8)

The dTCR or scTCR form of the TCRs of the invention may have amino acid sequences corresponding to human αβ TCR extracellular constant and variable domain sequences, and a disulfide bond may link amino acid residues of the said constant domain sequences, which disulfide bond has no equivalent in native TCRs.

The disulfide bond is between cysteine residues corresponding to amino acid residues whose β carbon atoms are less than 0.6 nm apart in native TCRs, for example between cysteine residues substituted for Thr 48 of exon 1 of TRAC*01 and Ser 57 of exon 1 of TRBC1*01 or TRBC2*01 or the non-human equivalent thereof. Other sites where cysteines can be introduced to form the disulfide bond are the following residues in exon 1 of TRAC*01 for the TCR α chain and TRBC1*01 or TRBC2*01 for the TCR β chain:

| TCR α chain | TCR β chain | Native β carbon separation (nm) |
|---|---|---|
| Thr 45 | Ser 77 | 0.533 |
| Tyr 10 | Ser 17 | 0.359 |
| Thr 45 | Asp 59 | 0.560 |
| Ser 15 | Glu 15 | 0.59 |

In addition to the non-native disulfide bond referred to above, the dTCR or scTCR form of the TCRs of the invention may include a disulfide bond between residues corresponding to those linked by a disulfide bond in native TCRs.

The dTCR or scTCR form of the TCRs of the invention preferably does not contain a sequence corresponding to transmembrane or cytoplasmic sequences of native TCRs.

Preferred embodiments of the invention provide a soluble TCR consisting of:
the alpha chain amino acid sequence of SEQ ID NO: 122 and beta chain amino acid sequence SEQ ID NO: 123:
the alpha chain amino acid sequence of SEQ ID NO: 122 and beta chain amino acid sequence SEQ ID NO: 124;

SEQ ID NOs: 122, 123 and 124 have been provided in a form which includes the N-terminal methionine (M) and the N-terminal "K" and "NA" in the TCR alpha and beta chain sequences respectively.

PEGylated TCR Monomers

In one particular embodiment a TCR of the invention is associated with at least one polyalkylene glycol chain(s). This association may be cause in a number of ways known to those skilled in the art. In a preferred embodiment the polyalkylene chain(s) is/are covalently linked to the TCR. In a further embodiment the polyethylene glycol chains of the present aspect of the invention comprise at least two polyethylene repeating units.

Multivalent TCR Complexes

One aspect of the invention provides a multivalent TCR complex comprising at least two TCRs of the invention. In one embodiment of this aspect, at least two TCR molecules are linked via linker moieties to form multivalent complexes. Preferably the complexes are water soluble, so the linker moiety should be selected accordingly. Furthermore, it is preferable that the linker moiety should be capable of attachment to defined positions on the TCR molecules, so that the structural diversity of the complexes formed is minimised. One embodiment of the present aspect is provided by a TCR complex of the invention wherein the polymer chain or peptidic linker sequence extends between amino acid residues of each TCR which are not located in a variable region sequence of the TCR.

Since the complexes of the invention may be for use in medicine, the linker moieties should be chosen with due regard to their pharmaceutical suitability, for example their immunogenicity.

Examples of linker moieties which fulfil the above desirable criteria are known in the art, for example the art of linking antibody fragments.

There are two classes of linker that are preferred for use in the production of multivalent TCR molecules of the present invention. A TCR complex of the invention in which the TCRs are linked by a polyalkylene glycol chain provides one embodiment of the present aspect.

The first are hydrophilic polymers such as polyalkylene glycols. The most commonly used of this class are based on polyethylene glycol or PEG, the structure of which is shown below.

$HOCH_2CH_2O(CH_2CH_2O)_n\text{—}CH_2CH_2OH$

Wherein n is greater than two. However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the PK profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) Tumor Targetting 4 235-244) The size of the hydrophilic polymer used my in particular be selected on the basis of the intended therapeutic use of the TCR complex. Thus for example, where the product is intended to leave the circulation and penetrate tissue, for example for use in the treatment of a tumour, it may be advantageous to use low molecular weight polymers in the order of 5 KDa. There are numerous review papers and books that detail the use of PEG and similar molecules in pharmaceutical formulations. For example, see Harris (1992) Polyethylene Glycol Chemistry—Biotechnical and Biomedical Applications, Plenum, New York, N.Y. or Harris & Zalipsky (1997) Chemistry and Biological Applications of Polyethylene Glycol ACS Books, Washington, D.C.

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the TCR. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

—$(CH_2)_n$— wherein n=2 to 5
—$(CH_2)_3NHCO(CH_2)_2$

A TCR complex of the invention in which a divalent alkylene spacer radical is located between the polyalkylene glycol chain and its point of attachment to a TCR of the complex provides a further embodiment of the present aspect.

A TCR complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| TCR Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |
| TCR dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order TCR multimers | | |
| 15K, 3 arms, Mal$_3$ (for trimer) | Nektar | OJOONO3 |
| 20K, 4 arms, Mal$_4$ (for tetramer) | Nektar | OJOOPO4 |
| 40K, 8 arms, Mal$_8$ (for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
Vinyl sulfone
Benzotriazole carbonate
Succinimidyl proprionate
Succinimidyl butanoate
Thio-ester
Acetaldehydes
Acrylates
Biotin
Primary amines As stated above non-PEG based polymers also provide suitable linkers for multimerising the TCRs of the present invention. For example, moieties containing maleimide termini linked by aliphatic chains such as BMH and BMOE (Pierce, products Nos. 22330 and 22323) can be used.

Peptidic linkers are the other class of TCR linkers. These linkers are comprised of chains of amino acids, and function to produce simple linkers or multimerisation domains onto which TCR molecules can be attached. The biotin/streptavidin system has previously been used to produce TCR tetramers (see WO/99/60119) for in-vitro binding studies. However, stepavidin is a microbially-derived polypeptide and as such not ideally suited to use in a therapeutic.

A TCR complex of the invention in which the TCRs are linked by a peptidic linker derived from a human multimerisation domain provides a further embodiment of the present aspect.

There are a number of human proteins that contain a multimerisation domain that could be used in the production of multivalent TCR complexes. For example the tetramerisation domain of p53 which has been utilised to produce tetramers of scFv antibody fragments which exhibited increased serum persistence and significantly reduced off-rate compared to the monomeric scFV fragment. (Willuda et al. (2001) J. Biol. Chem. 276 (17) 14385-14392) Haemoglobin also has a tetramerisation domain that could potentially be used for this kind of application.

A multivalent TCR complex of the invention comprising at least two TCRs provides a final embodiment of this aspect, wherein at least one of said TCRs is associated with a therapeutic agent.

In one aspect a TCR (or multivalent complex thereof) of the present invention may alternatively or additionally comprise a reactive cysteine at the C-terminal or N-terminal of the alpha or beta chains thereof.

Diagnostic and Therapeutic Use

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains.

In one aspect the TCR of the invention may be associated with a therapeutic agent or detectable moiety. For example, said therapeutic agent or detectable moiety may be covalently linked to the TCR.

In one embodiment of the invention said therapeutic agent or detectable moiety is covalently linked to the C-terminus of one or both TCR chains. In one aspect the scTCR or one or both of the dTCR chains of TCRs of the present invention may be labelled with an detectable moiety, for example a label that is suitable for diagnostic purposes. Such labelled TCRs are useful in a method for detecting a SLLMWITQC (SEQ ID NO:126)-HLA-A*0201 complex which method comprises contacting the TCR ligand with a TCR (or a multimeric high affinity TCR complex) which is specific for the TCR ligand; and detecting binding to the TCR ligand. In tetrameric TCR complexes formed for example, using biotinylated heterodimers, fluorescent streptavidin can be used to provide a detectable label. Such a fluorescently-labelled TCR tetramer is suitable for use in FACS analysis, for example to detect antigen presenting cells carrying the SLLMWITQC (SEQ ID NO:126)-HLA-A*0201 complex for which these high affinity TCRs are specific.

Another manner in which the soluble TCRs of the present invention may be detected is by the use of TCR-specific antibodies, in particular monoclonal antibodies. There are many commercially available anti-TCR antibodies, such as αF1 and βF1, which recognise the constant domains of the α and β chains, respectively.

In a further aspect a TCR (or multivalent complex thereof) of the present invention may alternatively or additionally be associated with (e.g. covalently or otherwise linked to) a therapeutic agent which may be, for example, a toxic moiety for use in cell killing, or an immune effector molecule such as an interleukin or a cytokine. A multivalent TCR complex of the invention may have enhanced binding capability for a TCR ligand compared to a non-multimeric wild-type or T cell receptor heterodimer of the invention. Thus, the multivalent TCR complexes according to the invention are particularly useful for tracking or targeting cells presenting particular antigens in vitro or in vivo, and are also useful as intermediates for the production of further multivalent TCR complexes having such uses. These TCRs or multivalent TCR complexes may therefore be provided in a pharmaceutically acceptable formulation for use in vivo.

The invention also provides a method for delivering a therapeutic agent to a target cell, which method comprises contacting potential target cells with a TCR or multivalent TCR complex in accordance with the invention under conditions to allow attachment of the TCR or multivalent TCR complex to the target cell, said TCR or multivalent TCR complex being specific for the SLLMWITQC (SEQ ID NO:126)-HLA-A*0201 complex and having the therapeutic agent associated therewith.

In particular, the soluble TCR or multivalent TCR complex of the present invention can be used to deliver therapeutic agents to the location of cells presenting a particular antigen. This would be useful in many situations and, in particular, against tumours. A therapeutic agent could be delivered such that it would exercise its effect locally but not only on the cell it binds to. Thus, one particular strategy envisages anti-tumour molecules linked to TCRs or multivalent TCR complexes according to the invention specific for tumour antigens.

Many therapeutic agents could be employed for this use, for instance radioactive compounds, enzymes (perforin for example) or chemotherapeutic agents (cis-platin for example). To ensure that toxic effects are exercised in the desired location the toxin could be inside a liposome linked to streptavidin so that the compound is released slowly. This will prevent damaging effects during the transport in the body and ensure that the toxin has maximum effect after binding of the TCR to the relevant antigen presenting cells.

Other suitable therapeutic agents include:

small molecule cytotoxic agents, i.e. compounds with the ability to kill mammalian cells having a molecular weight of less than 700 daltons. Such compounds could also contain toxic metals capable of having a cytotoxic effect. Furthermore, it is to be understood that these small molecule cytotoxic agents also include pro-drugs, i.e. compounds that decay or are converted under physiological conditions to release cytotoxic agents. Examples of such agents include cis-platin, maytansine derivatives, rachelmycin, calicheamicin, docetaxel, etoposide, gemcitabine, ifosfamide, irinotecan, melphalan, mitoxantrone, sorfimer sodiumphotofrin II, temozolmide, topotecan, trimetreate glucuronate, auristatin E vincristine and doxorubicin;

peptide cytotoxins, i.e. proteins or fragments thereof with the ability to kill mammalian cells. Including but not limited to, ricin, diphtheria toxin, pseudomonas bacterial exotoxin A, DNAase and RNAase;

radio-nuclides, i.e. unstable isotopes of elements which decay with the concurrent emission of one or more of α or β particles, or γ rays including but not limited to, iodine 131, rhenium 186, indium 111, yttrium 90, bismuth 210 and 213, actinium 225 and astatine 213; chelating agents may be used to facilitate the association of these radio-nuclides to the high affinity TCRs, or multimers thereof;

prodrugs, including but not limited to, antibody directed enzyme pro-drugs;

immuno-stimulants, i.e. moieties which stimulate immune response. Including but not limited to, cytokines such as IL-2 and IFN, Superantigens and mutants thereof, TCR-HLA fusions and chemokines such as IL-8, platelet factor 4, melanoma growth stimulatory protein, etc, antibodies or fragments thereof, complement activators, xenogeneic protein domains, allogeneic protein domains, viral/bacterial protein domains, viral/bacterial peptides and anti-T cell determinant antibodies (e.g. anti-CD3 or anti-CD28).

Functional Antibody Fragments and Variants

Antibody fragments and variants/analogues which are suitable for use in the compositions and methods described herein include, but are not limited to, the following.

Antibody Fragments

As is known to those skilled in the art, it is possible to produce fragments of a given antibody which retain substantially the same binding characteristics as those of the parent antibody. The following provides details of such fragments:

Minibodies—These constructs consist of antibodies with a truncated Fc portion. As such they retain the complete binding domains of the antibody from which are derived.

Fab fragments—These comprise a single immunoglobulin light chain covalently-linked to part of an immunoglobulin heavy chain. As such, Fab fragments comprise a single antigen combining site. Fab fragments are defined by the portion of an IgG that can be liberated by treatment with papain. Such fragments are commonly produced via recombinant DNA techniques. (Reeves et al., (2000) *Lecture Notes on Immunology* (4th Edition) Published by Blackwell Science)

F(ab')$_2$ fragments—These comprise both antigen combining sites and the hinge region from a single antibody. F(ab')$_2$ fragments are defined by the portion of an IgG that can be liberated by treatment with pepsin. Such fragments are commonly produced via recombinant DNA techniques. (Reeves et al., (2000) *Lecture Notes on Immunology* (4th Edition) Published by Blackwell Science)

Fv fragments—These comprise an immunoglobulin variable heavy domain linked to an immunoglobulin variable light domain. A number of Fv designs have been produced. These include dsFvs, in which the association between the two domains is enhanced by an introduced disulfide bond. Alternatively, scFVs can be formed using a peptide linker to bind the two domains together as a single polypeptide. Fvs constructs containing a variable domain of a heavy or light immunoglobulin chain associated to the variable and constant domain of the corresponding immunoglobulin heavy or light chain have also been produced. FV have also been multimerised to form diabodies and triabodies (Maynard et al., (2000) *Annu Rev Biomed Eng* 2 339-376)

Nanobodies™—These constructs, marketed by Ablynx (Belgium), comprise synthetic single immunoglobulin variable heavy domain derived from a camelid (e.g. camel or llama) antibody.

Domain Antibodies—These constructs, marketed by Domantis (Belgium), comprise an affinity matured single immunoglobulin variable heavy domain or immunoglobulin variable light domain.

Antibody Variants and Analogues

The defining functional characteristic of antibodies in the context of the present invention is their ability to bind specifically to a target ligand. As is known to those skilled in the art it is possible to engineer such binding characteristics into a range of other proteins. Examples of antibody variants and analogues suitable for use in the compositions and methods of the present invention include, but are not limited to, the following.

Protein scaffold-based binding polypeptides—This family of binding constructs comprise mutated analogues of proteins which contain native binding loops. Examples include Affibodies, marketed by Affibody (Sweden), which are based on a three-helix motif derived from one of the IgG binding domains of *Staphylococcus aureus* Protein A. Another example is provided by Evibodies, marketed by EvoGenix (Australia) which are based on the extracellular domains of CTLA-4 into which domains similar to antibody binding loops are grafted. A final example, Cytokine Traps marketed by Regeneron Pharmaceuticals (US), graft cytokine receptor domains into antibody scaffolds. (Nygren et al., (2000) *Current Opinion in Structural biology* 7 463-469) provides a review of the uses of scaffolds for engineering novel binding sites in proteins. This review mentions the following proteins as sources of scaffolds: CP1 zinc finger, Tendamistat, Z domain (a protein A analogue), PST1, Coiled coils, LACI-D1 and cytochrome $b_{562}$. Other protein scaffold studies have reported the use of Fibronectin, Green fluorescent protein (GFP) and ankyrin repeats.

As is known to those skilled in the art antibodies or fragments, variants or analogues thereof can be produced which bind to various parts of a given protein ligand. For example, anti-CD3 antibodies can be raised to any of the polypeptide chains from which this complex is formed (i.e., γ, δ, ε, ζ, and η CD3 chains) Antibodies which bind to the ε CD3 chain are the preferred anti-CD3 antibodies for use in the compositions and methods of the present invention.

Soluble TCRs or multivalent TCR complexes of the invention may be linked to an enzyme capable of converting a prodrug to a drug. This allows the prodrug to be converted to the drug only at the site where it is required (i.e. targeted by the sTCR).

It is expected that the high affinity SLLMWITQC (SEQ ID NO:126)-HLA-A*0201 specific TCRs disclosed herein may be used in methods for the diagnosis and treatment of cancer.

For cancer treatment, the localisation in the vicinity of tumours or metastasis would enhance the effect of toxins or immunostimulants. For vaccine delivery, the vaccine antigen could be localised in the vicinity of antigen presenting cells, thus enhancing the efficacy of the antigen. The method can also be applied for imaging purposes.

One embodiment is provided by an isolated cell presenting a TCR of the invention. For example, said cell may be a T cell.

Further embodiments of the invention are provided by a pharmaceutical composition comprising:

a TCR or a multivalent TCR complex of the invention (optionally associated with a therapeutic agent), or a plurality of cells presenting at least one TCR of the invention, together with a pharmaceutically acceptable carrier;

The invention also provides a method of treatment of cancer comprising administering to a subject suffering such cancer disease an effective amount of a TCR or a multivalent TCR complex of the invention (optionally associated with a therapeutic agent), or a plurality of cells presenting at least one TCR of the invention. In a related embodiment the invention provides for the use of a TCR or a multivalent TCR complex of the invention (optionally associated with a therapeutic agent), or a plurality of cells presenting at least one TCR of the invention, in the preparation of a composition for the treatment of cancer.

Therapeutic or imaging TCRs in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by admixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A scTCR or dTCR (which preferably is constituted by constant and variable sequences corresponding to human sequences) of the present invention maybe provided in substantially pure form, or as a purified or isolated preparation. For example, it may be provided in a form which is substantially free of other proteins.

The invention also provides a method of producing a high affinity TCR having the property of binding to SLLMWITQC (SEQ ID NO:126)-HLA-A*0201. CHARACTERISED IN THAT the TCR (i) comprises at least one TCR α chain variable domain and/or at least one TCR β chain variable domain and (ii) has a KD for the said SLLMWITQC (SEQ ID NO:126)-HLA-A*0201 complex of less than or equal to 1 µM and/or an off-rate (kOff) for the SLLMWITQC (SEQ ID NO:126)-HLA-A*0201 complex of $1 \times 10^{-3}$ $S^{-1}$ or slower, wherein the method comprises:

(a) the production of a TCR comprising the α and β chain variable domains of the 1G4 TCR wherein one or both of the α and β chain variable domains comprise a mutation(s) in one or more of the amino acids identified in claims 7 and 8;

(b) contacting said mutated TCR with SLLMWITQC(SEQ ID NO:126)-HLA-A*0201 under conditions suitable to allow the binding of the TCR to SLLMWITQC (SEQ ID NO:126)-HLA-A*0201;

and measuring the $K_D$ and/or $k_{off}$ of the interaction.

Preferred features of each aspect of the invention are as for each of the other aspects mutatis mutandis. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIGS. 1*a* and 1*b* details the alpha chain variable domain amino acid and beta chain variable domain amino acid sequences of the native 1G4 TCR respectively.

FIGS. 2*a* and 2*b* show respectively the DNA sequence of soluble versions of the native 1G4 TCR α and β chains.

FIGS. 3*a* and 3*b* show respectively the 1G4 TCR α and β chain extracellular amino acid sequences produced from the DNA sequences of FIGS. 2*a* and 2*b*.

FIGS. 4*a* and 4*b* show respectively the DNA sequence of soluble versions of the 1G4 TCR α and β chains mutated to include additional cysteine residues to form a non-native disulphide bond. The mutated codon is indicated by shading.

FIGS. 5*a* and 5*b* show respectively the 1G4 TCR α and β chain extracellular amino acid sequences produced from the DNA sequences of FIGS. 4*a* and 4*b*. The introduced cysteine is indicated by shading.

FIG. 6 details the alpha chain variable domain amino acid sequences of the high affinity 1G4 TCR variants.

FIG. 7 details the beta chain variable domain amino acid sequences of the high affinity 1G4 TCR variants.

FIG. 8*a* details the amino acid sequence of a soluble form of TRAC.

FIG. 8*b* details the amino acid sequence of a soluble form of TRBC1.

FIG. 8*c* details the amino acid sequence of a soluble form of TRBC2.

FIG. 9 details the DNA sequence of the pEX954 plasmid.
FIG. 10 details the DNA sequence of the pEX821 plasmid.
FIG. 11 details the DNA sequence of the pEX202 plasmid.
FIG. 12 details the DNA sequence of the pEX205 plasmid.

FIG. 13 details further beta chain variable domain amino acid sequences of the high affinity 1G4 TCR variants.

FIG. 14*a* details the alpha chain amino acid sequences of a preferred soluble high affinity 1G4 TCR variant.

FIG. 14*b* details the beta chain amino acid sequences of a preferred (c58c61) soluble high affinity 1G4 TCR variant utilising the TRBC1 constant domain.

FIG. 14*c* details the beta chain amino acid sequences of a preferred (c58c61) soluble high affinity 1G4 TCR variant utilising the TRBC2 constant domain.

FIG. 14*d* details the beta chain amino acid sequences of a preferred (c58c61) soluble high affinity 1G4 TCR using the TRBC2 encoded constant region fused via a peptide linker to wild-type human IL-2.

FIG. 15*a* shows FACs staining of T2 cell pulsed with a range of NY-ESO-analogue SLLMWITQV (SEQ ID NO:127) peptide concentrations using the high affinity c58c61 1G4 TCR-IL-2 fusion proteins.

FIG. 15*b* shows FACs staining of T2 cell pulsed with a range of NY-ESO-derived SLLMWITQC (SEQ ID NO:126) peptide concentrations using the high affinity c58c61 1G4 TCR-IL-2 fusion proteins.

Example 1

Figure 15A:
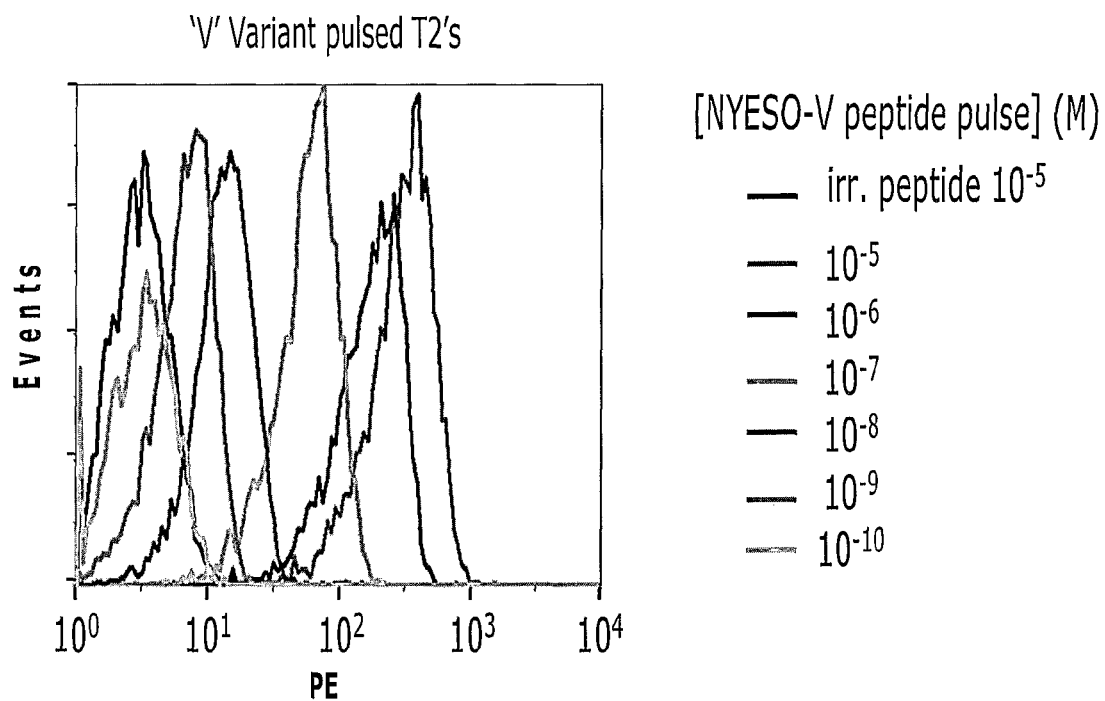

Production of a Soluble Disulfide-Linked TCR Comprising the Native 1G4 TCR Variable Domain RNA Isolation Total RNA was isolated from 10000 clonal T cells by re-suspension in 100 µl tri-reagent (Sigma) and processing of the lysate according to the manufacturer's instructions. After the final precipitation the RNA was re-dissolved in 12.5 µl RNAse free water.

cDNA Production

To the above sample of RNA, 2.5/µl of 10 mM oligo-dT$^{15}$ (Promega) was added and the sample incubated at 60° C. for 2 minutes then placed on ice. Reverse transcription was carried out using OmniscriptRT kit (Qiagen) by addition of 2 \ RT buffer (10×), 2 µl 5 mM dNTP, 1 µl Omniscript reverse transcriptase. The sample was mixed and incubated for 1 hour at 37° C. cDNA was then stored at −80° C.

The above cDNA was used as template. A panel of forward primers covering all possible alpha and beta variable chains was used to screen for, and amplify by PCR, alpha and beta chains genes. Primer sequences used for TCR chain gene amplification were designed from the NCBI website (ncbi.nlm.nih.gov/Entrez/) using accession numbers obtained from the T cell receptor Factsbook, (2001) LeFranc and LeFranc, Academic Press, ISBN 0-12-441352-8. Alpha-chain forward primers were designed to contain a ClaI restriction site and the universal alpha chain reverse primer a SalI restriction site. Beta-chain forward primers were designed to contain an AseI restriction site and universal beta reverse primer an AgeI restriction site.

Recipient vectors for the TCR gene fragments were based on a pGMT7 parent plasmid, which contains the T7 promoter for high level expression in *E. coli* strain BL21-DE3(pLysS) (Pan et al., *Biotechniques* (2000) 29 (6): 1234-8).

Alpha chain purified PCR products were digested with ClaI and SalII and ligated into pEX954 (see FIG. 9) cut with ClaI and XhoI.

Beta chain purified PCR products were digested with AseI and AgeI and ligated into pEX821 (See FIG. 10) cut with NdeI/AgeI.

Ligation

The cut PCR product and cut vector were ligated using a rapid DNA ligation kit (Roche) following the manufacturers instructions.

Ligated plasmids were transformed into competent *E. coli* strain XL1-blue cells and plated out on LB/agar plates containing 100 mg/ml ampicillin. Following incubation overnight at 37° C., single colonies were picked and grown in 10 ml LB containing 100 mg/ml ampicillin overnight at 37° C. with shaking. Cloned plasmids were purified using a Miniprep kit (Qiagen) and the insert was sequenced using an automated DNA sequencer (Lark Technologies).

FIGS. 4*a* and 4*b* show respectively the DNA sequence of soluble versions of the 1G4 TCR α and β chains mutated to include additional cysteine residues to form a non-native disulphide bond.

FIGS. 5*a* and 5*b* show respectively the NY-ESO TCR α and β chain extracellular amino acid sequences produced from the DNA sequences of FIGS. 4*a* and 4*b*.

Example 2

Production of High Affinity Variants of the Soluble Disulfide Linked 1G4 TCR

The soluble disulfide-linked native 1G4 TCR produced as described in Example 1 can be used a template from which to produce the TCRs of the invention which have an increased affinity for the SLLMWITQC (SEQ ID NO: 126)-HLA-A*0201 complex.

The amino sequences of the mutated TCR alpha and beta chain variable domains which demonstrate high affinity for the SLLMWITQC (SEQ ID NO:126)-HLA-A*0201 complex are listed in FIGS. 6 and 7 respectively (SEQ ID Nos: 11-83 and 84-99 respectively). As is known to those skilled in the art the necessary codon changes required to produce these mutated chains can be introduced into the DNA encoding these chains by site-directed mutagenesis. (QUICK-CHANGE™ Site-Directed Mutagenesis Kit from Stratagene).

Briefly, this is achieved by using primers that incorporate the desired codon change(s) and the plasmids containing the relevant 1G4 TCR chain as a template for the mutagenesis:

Mutagenesis was carried out using the following conditions: 50 ng plasmid template, 1 µl of 10 mM dNTP, 5 µl of 10×Pfu DNA polymerase buffer as supplied by the manufacturer, 25 pmol of fwd primer, 25 pmol of rev primer, 1 µl pfu DNA polymerase in total volume 50 µl. After an initial denaturation step of 2 mins at 95 C, the reaction was subjected to 25 cycles of denaturation (95 C, 10 secs), annealing (55 C 10 secs), and elongation (72 C, 8 mins). The resulting product was digested with DpnI restriction enzyme to remove the template plasmid and transformed into *E. coli* strain XL1-blue. Mutagenesis was verified by sequencing.

Example 3

Production of Soluble "Zippered" High Affinity TCRs

Alpha Chain—c-jun Leucine Zipper

The construct was made by PCR stitching.

For the 5'-end of the gene the plasmid coding for the high affinity TCR alpha chains and containing the code for the introduced inter-chain di-sulfide bridge was used as template. PCR with the following two primer pairs generated the desired variable domain.

```
5'-TRAV21 fwd
                                     (SEQ ID NO: 105)
tctctcattaatgaaacaggaggtgacgcagattcct C-alpha rev
                                     (SEQ ID NO: 106)
CGGCAGGGTCAGGGTTCTGG
```

For the 3'-end of the gene the plasmid pEX202 (see FIG. 11), coding for a wild type affinity TCR alpha chain fused to human c-jun leucine zipper domain and not containing the code for the introduced inter-chain di-sulfide bridge, was used as template. PCR with the following primer pair generated the desired constant domain.

```
                                     (SEQ ID NO: 107)
  C-alpha fwd    CCAGAACCCTGACCCTGCCG (SEQ ID NO: 108)
  3'-alpha rev   aagcttcccgggggaactttctgggctggg
```

The two products were mixed and diluted 1000 fold and 1 µl was used as template in a 50 µl PCR with 5'-TRAV21 fwd and 3'-alpha rev primers.

The resulting PCR product was digested using restriction enzymes AseI and XmaI and ligated into pEX202 cut with NdeI and XmaI.

PCRs were carried out using the following conditions: 50 pg plasmid template, 1 µl of 10 mM dNTP, 5 µl of 10×Pfu DNA polymerase buffer as supplied by the manufacturer, 25 pmol of fwd primer, 25 pmol of rev primer, 1 µl Pfu DNA polymerase in total volume 50 µl. After an initial denaturation step of 2 mins at 95 C, the reaction was subjected to 30 cycles of denaturation (95 C, 10 secs), annealing (55 C 10 secs), and elongation (72 C, 2 mins).

Beta Chain—c-fos Leucine Zipper

The construct was made by PCR stitching.

For the 5'-end of the gene plasmids coding for the high affinity TCR beta chains and containing the introduced interchain di-sulfide bridge were used as template. PCR with the following two primers generated the desired variable domain gene fragment.

```
                            (SEQ ID NO: 109)
TRBV6-5 fwd    tctctcattaatgaatgctggtgtcactcagacccc (SEQ ID NO: 110)
C-beta rev     CTTCTGATGGCTCAAACACAGC
```

For the 3'-end of the gene the plasmid pEX205 (see FIG. 12), coding for a wild type affinity TCR beta chain fused to the human c-fos leucine zipper domain and not containing the code for the introduced inter-chain di-sulfide bridge, was used as template. PCR with the following two primers generated the desired constant domain gene fragment.

```
                            (SEQ ID NO: 111)
C-beta fwd    GCTGTGTTTGAGCCATCAGAAG (SEQ ID NO: 112)
TRBC rev      aagcttcccggggtctgctctaccccaggc
```

The two products were mixed and diluted 1000 fold and 1 µl was used as template in a 50 µl PCR with TRBV6-5 fwd and TRBC rev primers. PCRs were carried out as described above.

The resulting PCR product was digested using restriction enzymes AseI and XmaI and ligated into pEX205 cut with NdeI and XmaI.

Example 4

Expression, Refolding and Purification of Soluble TCR

The expression plasmids containing the mutated α-chain and β-chain respectively as prepared in Examples 1, 2 or 3 were transformed separately into *E. coli* strain BL21pLysS, and single ampicillin-resistant colonies were grown at 37° C. in TYP (ampicillin 100 µg/ml) medium to $OD_{600}$ of 0.4 before inducing protein expression with 0.5 mM IPTG. Cells were harvested three hours post-induction by centrifugation for 30 minutes at 4000 rpm in a Beckman J-6B. Cell pellets were re-suspended in a buffer containing 50 mM Tris-HCl, 25% (w/v) sucrose, 1 mM NaEDTA, 0.1% (w/v) NaAzide, 10 mM DTT, pH 8.0. After an overnight freeze-thaw step, re-suspended cells were sonicated in 1 minute bursts for a total of around 10 minutes in a Milsonix XL2020 sonicator using a standard 12 mm diameter probe. Inclusion body pellets were recovered by centrifugation for 30 minutes at 13000 rpm in a Beckman J2-21 centrifuge. Three detergent washes were then carried out to remove cell debris and membrane components. Each time the inclusion body pellet was homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 13000 rpm in a Beckman J2-21. Detergent and salt was then removed by a similar wash in the following buffer: 50 mM Tris-HCl, 1 mM NaEDTA, 0.1% (w/v) NaAzide, 2 mM DTT, pH 8.0. Finally, the inclusion bodies were divided into 30 mg aliquots and frozen at −70° C. Inclusion body protein yield was quantitated by solubilising with 6M guanidine-HCl and measurement with a Bradford dye-binding assay (PerBio).

Approximately 30 mg of TCR β chain and 60 mg of TCR α chain solubilised inclusion bodies were thawed from frozen stocks, samples were then mixed and the mixture diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured TCR chains was then injected into 1 liter of the following refolding buffer: 100 mM Tris pH 8.5, 400 mM L-Arginine, 2 mM EDTA, 5 mM reduced Glutathione, 0.5 mM oxidised Glutathione, 5M urea, 0.2 mM PMSF. The redox couple (2-mercaptoethylamine and cystamine (to final concentrations of 6.6 mM and 3.7 mM, respectively) were added approximately 5 minutes before addition of the denatured TCR chains. The solution was left for 5 hrs±15 minutes. The refolded TCR was dialysed in Spectrapor 1 membrane (Spectrum; Product No. 132670) against 10 L 10 mM Tris pH 8.1 at 5° C.±3° C. for 18-20 hours. After this time, the dialysis buffer was changed to fresh 10 mM Tris pH 8.1 (10 L) and dialysis was continued at 5° C. 13° C. for another 20-22 hours.

sTCR was separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions were stored at 4° C. and analysed by Coomassie-stained SDS-PAGE before being pooled and concentrated. Finally, the sTCR was purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 50 kDa was pooled and concentrated prior to characterisation by BIAcore surface plasmon resonance analysis.

Example 5

Biacore Surface Plasmon Resonance Characterisation of sTCR Binding to Specific pMHC A surface plasmon resonance biosensor (Biacore 3000™) was used to analyse the binding of a sTCR to its peptide-MHC ligand. This was facilitated by producing single pMHC complexes (described below) which were immobilised to a streptavidin-coated binding surface in a semi-oriented fashion, allowing efficient testing of the binding of a soluble T-cell receptor to up to four different pMHC (immobilised on separate flow cells) simultaneously. Manual injection of HLA complex allows the precise level of immobilised class I molecules to be manipulated easily.

Biotinylated class I HLA-A*0201 molecules were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). HLA-A*0201-heavy chain was expressed with a C-terminal biotinylation tag which replaces the transmembrane and cytoplasmic domains of the protein in an appropriate construct. Inclusion body expression levels of ~75 mg/liter bacterial culture were obtained. The MHC light-chain or β2-microglobulin was also expressed as inclusion bodies in *E. coli* from an appropriate construct, at a level of ~500 mg/liter bacterial culture.

E. coli cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/liter heavy chain, 30 mg/liter β2m into 0.4 M L-Arginine-HCl, 100 mM Tris pH 8.1, 3.7 mM cystamine, mM cysteamine, 4 mg/ml of the SLLMWITQC peptide required to be loaded by the HLA-A*0201 molecule, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 µm cellulose acetate filter and loaded onto a POROS 50HQ anion exchange column (8 ml bed volume). Protein was eluted with a linear 0-500 mM NaCl gradient. HLA-A*0201-peptide complex eluted at approximately 250 mM NaCl, and peak fractions were collected, a cocktail of protease inhibitors (Calbiochem) was added and the fractions were chilled on ice.

Biotinylation tagged pMHC molecules were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl2, and 5 µg/ml BirA enzyme (purified according to O'Callaghan et al. (1999) Anal. Biochem. 266: 9-15). The mixture was then allowed to incubate at room temperature overnight.

The biotinylated pHLA-A*0201 molecules were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pHLA-A*0201 molecules eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pHLA-A*0201 molecules were stored frozen at −20° C. Streptavidin was immobilised by standard amine coupling methods.

Such immobilised complexes are capable of binding both T-cell receptors and the coreceptor CD8αα, both of which may be injected in the soluble phase. Specific binding of TCR is obtained even at low concentrations (at least 40 µg/ml), implying the TCR is relatively stable. The pMHC binding properties of sTCR are observed to be qualitatively and quantitatively similar if sTCR is used either in the soluble or immobilised phase. This is an important control for partial activity of soluble species and also suggests that biotinylated pMHC complexes are biologically as active as non-biotinylated complexes.

The interactions between 1G4 sTCR containing a novel inter-chain bond and its ligand/MHC complex or an irrelevant HLA-peptide combination, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the individual HLA-peptide complexes in separate flow cells via binding between the biotin cross linked onto β2m and streptavidin which have been chemically cross linked to the activated surface of the flow cells. The assay was then performed by passing sTCR over the surfaces of the different flow cells at a constant flow rate, measuring the SPR response in doing so.

To Measure Equilibrium Binding Constant

Serial dilutions of WT 1G4 sTCR were prepared and injected at constant flow rate of 5 µl min-1 over two different flow cells; one coated with ~1000 RU of specific SLLM-WITQC (SEQ ID NO:126)-HLA-A*0201 complex, the second coated with ~1000 RU of non-specific HLA-A2-peptide complex. Response was normalised for each concentration using the measurement from the control cell. Normalised data response was plotted versus concentration of TCR sample and fitted to a hyperbola in order to calculate the equilibrium binding constant, $K_D$. (Price & Dwek, Principles and Problems in Physical Chemistry for Biochemists (2nd Edition) 1979, Clarendon Press, Oxford).

To Measure Kinetic Parameters

For high affinity TCRs $K_D$ was determined by experimentally measuring the dissociation rate constant, kd, and the association rate constant, ka. The equilibrium constant $K_D$ was calculated as kd/ka. TCR was injected over two different cells one coated with ~300 RU of specific HLA-A2-nyeso peptide complex, the second coated with ~300 RU of non-specific HLA-A2-peptide complex. Flow rate was set at 50 µl/min. Typically 250 µl of TCR at ~3 µM concentration was injected. Buffer was then flowed over until the response had returned to baseline. Kinetic parameters were calculated using Biaevaluation software. The dissociation phase was also fitted to a single exponential decay equation enabling calculation of half-life.

Results

The interaction between a soluble disulfide-linked native 1G4 TCR (consisting of the α and β TCR chains detailed in SEQ ID NOs 9 and 10 respectively) and the SLLMWITQC (SEQ ID NO:126)-HLA-A*0201 complex was analysed using the above methods and demonstrated a $K_D$ of 15 µM and a $k_{off}$ of $1.28 \times 10^{-1}$ $S^{-1}$.

The TCRs specified in the following table have a $K_D$ of less than or equal to 1 µM and/or a $k_{off}$ of $1 \times 10^{-3}$ $S^{-1}$ or slower.

| Alpha chain variable domain sequence, SEQ ID NO: | Beta chain variable domain sequence, SEQ ID NO: |
|---|---|
| 1 | 84 |
| 1 | 85 |
| 1 | 86 |
| 1 | 87 |
| 1 | 88 |
| 11 | 84 |
| 12 | 84 |
| 12 | 85 |
| 12 | 90 |
| 11 | 85 |
| 11 | 86 |
| 11 | 92 |
| 11 | 93 |
| 13 | 86 |
| 14 | 84 |
| 14 | 85 |
| 15 | 84 |
| 15 | 85 |
| 16 | 84 |
| 16 | 85 |
| 17 | 86 |
| 18 | 86 |
| 19 | 84 |

| Alpha chain variable domain sequence, SEQ ID NO: | Beta chain variable domain sequence, SEQ ID NO: |
|---|---|
| 20 | 86 |
| 21 | 84 |
| 21 | 85 |
| 22 | 84 |
| 23 | 86 |
| 24 | 84 |
| 25 | 84 |
| 26 | 84 |
| 27 | 84 |
| 28 | 84 |
| 29 | 84 |
| 30 | 84 |
| 31 | 84 |
| 32 | 84 |
| 33 | 84 |
| 20 | 86 |
| 34 | 86 |
| 35 | 89 |
| 36 | 89 |
| 37 | 89 |
| 38 | 89 |
| 39 | 89 |
| 16 | 89 |
| 17 | 89 |
| 31 | 89 |
| 40 | 89 |
| 1 | 90 |
| 1 | 91 |
| 41 | 90 |
| 42 | 2 |
| 42 | 85 |
| 42 | 92 |
| 1 | 92 |
| 1 | 93 |
| 43 | 92 |
| 44 | 92 |
| 45 | 92 |
| 46 | 92 |
| 47 | 92 |
| 48 | 84 |
| 49 | 94 |
| 50 | 84 |
| 50 | 94 |
| 51 | 94 |
| 51 | 95 |
| 1 | 94 |
| 1 | 85 |
| 51 | 84 |
| 52 | 84 |
| 52 | 94 |
| 52 | 95 |
| 53 | 84 |
| 49 | 95 |
| 49 | 94 |
| 54 | 92 |
| 55 | 92 |
| 56 | 92 |
| 57 | 92 |
| 58 | 92 |
| 59 | 92 |
| 60 | 92 |
| 61 | 92 |
| 62 | 92 |
| 63 | 92 |
| 64 | 92 |
| 65 | 92 |
| 66 | 92 |
| 67 | 92 |
| 68 | 92 |
| 69 | 92 |
| 70 | 92 |
| 71 | 92 |
| 72 | 92 |
| 73 | 92 |
| 74 | 92 |
| 75 | 92 |
| 76 | 92 |
| 77 | 92 |
| 78 | 92 |
| 79 | 92 |
| 80 | 92 |
| 81 | 92 |
| 82 | 92 |
| 83 | 92 |
| 11 | 96 |
| 11 | 97 |
| 11 | 98 |
| 11 | 99 |
| 1 | 89 |
| 50 | 117 |
| 49 | 117 |
| 50 | 118 |
| 49 | 119 |
| 50 | 119 |
| 58 | 93 |
| 49 | 118 |
| 1 | 119 |
| 1 | 117 |
| 55 | 120 |
| 56 | 120 |
| 50 | 121 |
| 50 | 120 |
| 49 | 121 |
| 49 | 120 |
| 48 | 118 |
| 53 | 95 |

Example 6

In-Vitro Cell Staining Using a High Affinity c58c61 NY-ESO TCR-IL-2 Fusion Protein T2 lymphoblastoid cells were pulsed with the NY-ESO-derived SLLMWITQC (SEQ ID NO:126), NY-ESO-analogue SLLMWITQV (SEQ ID NO:127) peptide, or an irrelevant peptide at a range of concentrations ($10^{-5}$-$10^{-10}$ M) for 180 minutes at 37° C. The NY-ESO-analogue SLLMWITQV (SEQ ID NO:127) peptide (V-variant peptide) was used as this peptide is known to have a higher affinity for the binding cleft of the HLA-A*0201 complex than the native NY-ESO-derived SLLMWITQC (SEQ ID NO:126) peptide. After pulsing, cells were washed in serum-free RPMI and $5 \times 10^5$ cells were incubated with high affinity c58c61 NY-ESO TCR-IL-2 fusion protein for 10 min at room temperature, followed by secondary anti-IL-2 mAb conjugated with PE (Serotec) for 15 min at room temperature. After washing, bound TCR-IL-2 was quantified by flow cytometry using a FACS Vantage SE (Becton Dickinson). Controls, also using peptide-pulsed T2 cells were included where TCR-IL-2 was omitted.

FIG. 14a details the amino acid sequence of the alpha chain of the c58c61 NY-ESO TCR. (SEQ ID NO: 122).

FIG. 14c (SEQ ID NO: 124) details the amino acid sequence of the beta chain of the c58c61 NY-ESO TCR using the TRBC2 encoded constant region.

FIG. 14d (SEQ ID NO: 125) details the amino acid sequence of the beta chain of the c58c61 NY-ESO TCR using the TRBC2 encoded constant region fused via a peptide linker to wild-type human IL-2.

The alpha and beta chain variable domain mutations contained within the soluble c58c61 1G4 TCR-IL-2 fusion protein correspond to those detailed in SEQ ID NO: 49 and SEQ ID NO: 94 respectively. Note that SEQ ID NOs: 121-125 have been provided in a form which includes the N-terminal methionine (M) and the "K" and "NA" residues omitted in the majority of the other TCR alpha chain and beta chain amino acid sequences.

In similar experiments SK-MEL-37, ScaBER, J82, HcT1 19 and Colo 205 cancer cells transfected with a NY-ESO-derived SLLMWITQC (SEQ ID NO:126) peptide expressing ubiquitin minigene construct were used. The cancer cells were transfected using substantially the methods described in (Rimoldi et al, (2000) J. Immunol. 165 7253-7261). Cells were labelled as described above.

Results

FIG. 15a shows FACs staining of T2 cell pulsed with a range of NY-ESO-analogue SLLMWITQV (SEQ ID NO:127) peptide concentrations using the high affinity c58c61 1G4 TCR-IL-2 fusion proteins. FIG. 15a shows FACs staining of T2 cell pulsed with a range of NY-ESO-analogue SLLMWITQV (SEQ ID NO:127) peptide concentrations using the high affinity c58c61 1G4 TCR-IL-2 fusion proteins.

Figure 15B:
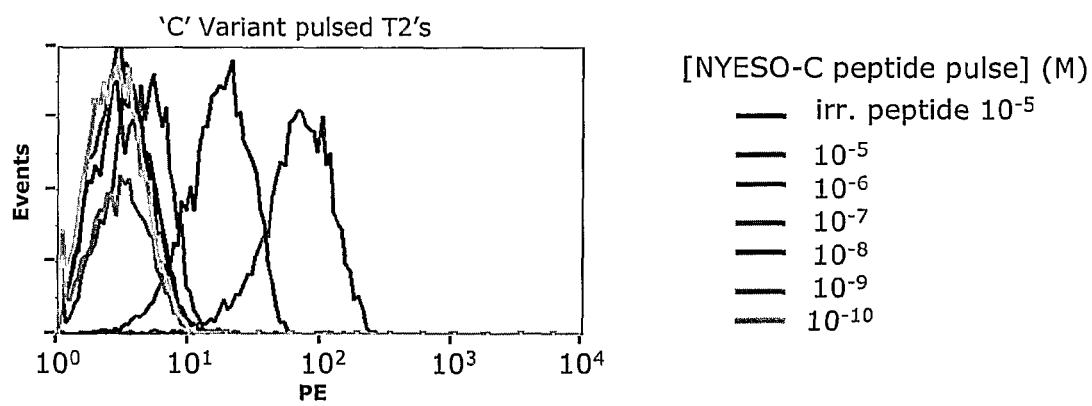

FIG. 15b shows FACs staining of T2 cell pulsed with a range of NY-ESO-derived SLLMWITQC (SEQ ID NO:126) peptide concentrations using the high affinity c58c61 1G4 TCR-IL-2 fusion proteins.

Figure 16:
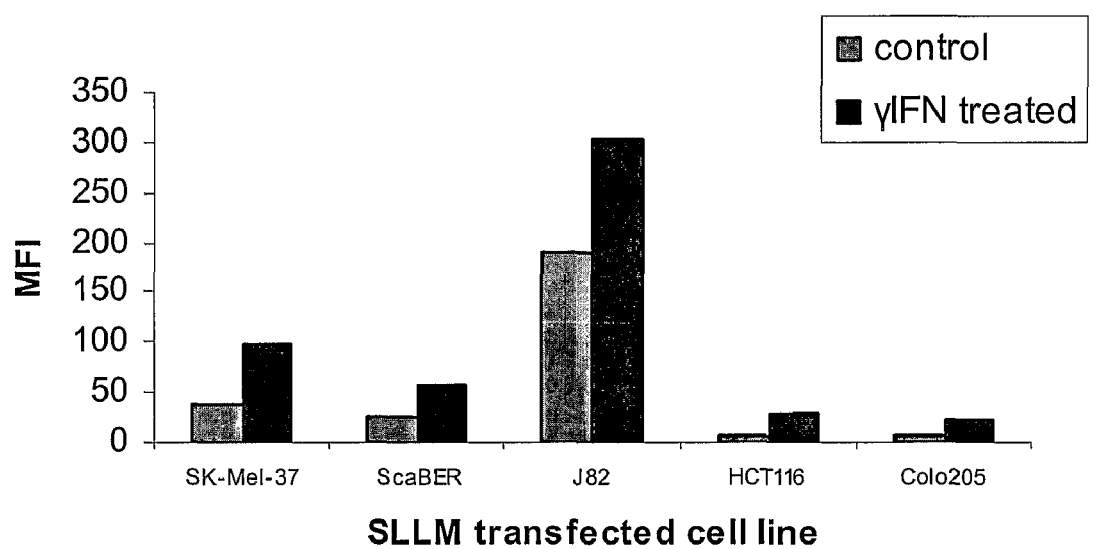
FIG. 16 shows FACs staining of SK-MEL-37, ScaBER, J82, HcT1 19 and Colo 205 cancer cells transfected with an SLLMWITQC (SEQ ID NO:126) peptide producing ubiquitin minigene (±proteosome inhibitors) using the high affinity c58c61 1G4 TCR-IL-2 fusion proteins.

FIG. 16 shows FACs staining of SK-MEL-37, ScaBER, J82, HcT1 19 and Colo 205 cancer cells transfected with an SLLMWITQC (SEQ ID NO:126) peptide producing ubiquitin minigene (±proteosome inhibitors) using the high affinity c58c61 1G4 TCR-IL-2 fusion proteins.

Example 9

CTL Activation ELISPOT Assay

The following assay was carried out to demonstrate that the soluble high affinity c58c61 NY-ESO TCR was capable of inhibiting activation of an SLLMWITQC (SEQ ID NO:126)-HLA-A*0201 specific CTL clone (1G4). IFN-γ production was used as the read-out for CTL activation.

Reagents

R1O Assay media: 10% FCS (heat-inactivated, Gibco, cat# 10108-165), 88% RPMI 1640 (Gibco, cat# 42401-018), 1% glutamine (Gibco, cat# 25030-024) and 1% penicillin/streptomycin (Gibco, cat# 15070-063).

Peptide: (obtained from various sources) initially dissolved in DMSO (Sigma, cat# D2650) at 4 mg/ml and frozen.

Wash buffer: 0.01M PBS/0.05% Tween 20 (1 sachet of Phosphate buffered saline with Tween 20, pH7.4 from Sigma, Cat. # P-3563 dissolved in 1 liter distilled water gives final composition 0.01M PBS, 0.138M NaCl, 0.0027M KCl, 0.05% Tween 20). PBS (Gibco, cat#10010-015).

The EliSpot kit contains all other reagents required i.e. capture and detection antibodies, skimmed milk powder, BSA, streptavidin-alkaline phosphatase, BCIP/NBT solution (Human IFN-g PVDF Eli-spot 20×96 wells with plates (IDS cat# DC-856.051.020, DC-856.000.000). The following method is based on the instructions supplied with each kit but contains some alterations.

MEL-624 and SK-MEL-37 melanoma cell lines were treated with trypsin for 5 minutes at 37° C. The cells are then washed and re-suspended in R10 media.

50000 target cells were then plated out per well in 50 μl of R10 media in a 96 well ELISPOT plate (Diaclone).

The following was then added to the above target cell cultures:

$1 \times 10^{-7}$ M high affinity c58c61 TCR, or an irrelevant TCR, in 50 μl of R10 media.

600 SLLMWITQC (SEQ ID NO:126)-HLA-A*0201 specific T cells (clone 1G4) in 50 μl of R10 media.

These cultures were then incubated for 24 hours at 37° C., 5% $CO_2$. The ELISPOT plates were processed according to the manufacturers instructions.

Results

Figure 17:
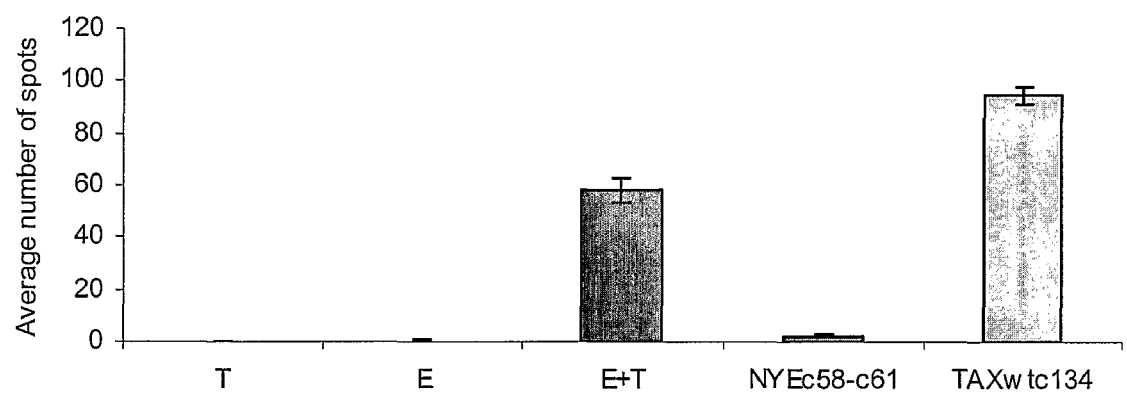
FIG. 17 shows ELISPOT data demonstrating the ability of soluble high affinity c58c61 1G4 TCR to inhibit CTL activation against the MEL-624 cancer cell.
Figure 18:
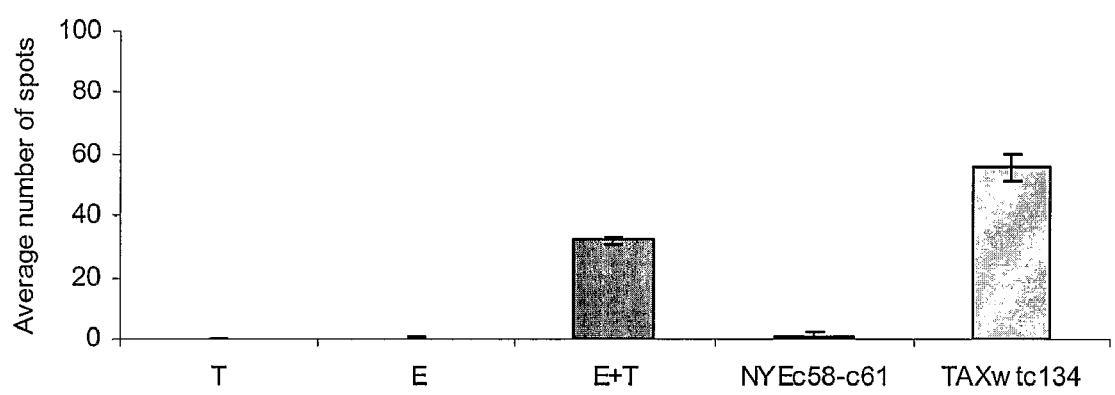
FIG. 18 shows ELISPOT data demonstrating the ability of soluble high affinity c58c61 1G4 TCR to inhibit CTL activation against the SK-MEL-37 cancer cell.

The soluble high affinity c58c61 1G4 TCR strongly inhibited the activation of 1G4 T cell clones against the melanoma cells, as measured by IFN-γ production. Whereas the irrelevant high affinity TCR had no inhibitory effect. (See FIG. 17 for MEL-624 cancer cell line results and FIG. 18 for SK-MEL-37 cancer cell line results).

Example 10

CTL Activation ELISA Assay

The following assay was carried out to demonstrate that the soluble high affinity c58c61 1G4 TCR was capable of inhibiting activation of an SLLMWITQC (SEQ ID NO:126)-HLA-A*0201 specific CTL clone (1G4). EFN-γ production was used as the read-out for CTL activation.

Reagents

R10 Assay media: 10% FCS (heat-inactivated, Gibco, cat# 10108-165), 88% RPMI 1640 (Gibco, cat# 42401-018), 1% glutamine (Gibco, cat# 25030-024) and 1% penicillin/streptomycin (Gibco, cat# 15070-063).

Peptide: (obtained from various sources) initially dissolved in DMSO (Sigma, cat# D2650) at 4 mg/ml and frozen.

Wash buffer: 0.01M PBS/0.05% Tween 20 (1 sachet of Phosphate buffered saline with Tween 20, pH7.4 from Sigma, Cat. # P-3563 dissolved in 1 liter distilled water gives final composition 0.01M PBS, 0.138M NaCl, 0.0027M KCl, 0.05% Tween 20). PBS (Gibco, cat#10010-015).

The ELISA kit contains all other reagents except BSA (Sigma), required i.e. capture and detection antibodies, skimmed milk powder, streptavidin-HRP, TMB solution (Human IFN-g Eli-pair 20×96 wells with plates. The following method is based substantially on the instructions supplied with each kit.

Method

ELISA plates were prepared according to the manufacturers instructions. (Diaclone kit, Immunodiagnostic systems, UK. T2 cell line target cells were washed and re-suspended in R10 media with or without varying concentrations (100 nM-10 pM) of SLLMWITQC (SEQ ID NO:126) peptide, then incubated for 1 hour at 37° C., 5% $CO_2$.

10,000 target cells per well were then plated out into a 96 well ELISA plate.

To these plates the following was added to the relevant well:

$1 \times 10^{-6}$ M to $3 \times 10^{-12}$ M of the high affinity c58c61 1G4 TCR or wild-type 1G4 TCR in 50 μl of R10 media.

5000 1G4 effector cells in 50 μl of R10 media.

The plates were then incubated for 48 hours at 37° C., 5% $CO_2$. The ELISA was then processed according to manufacturer's instructions.

Results

Figure 19:
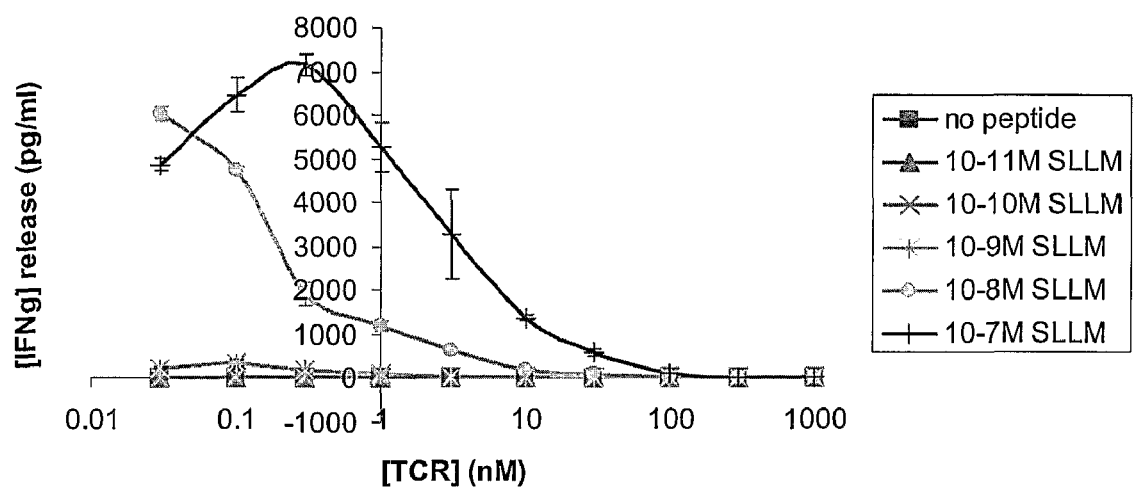
FIG. 19 shows inhibition of T cell activation against peptide pulsed T2 cells by the soluble c58c61 high affinity 1G4 TCR as measured by IFNγ production.
Figure 20:
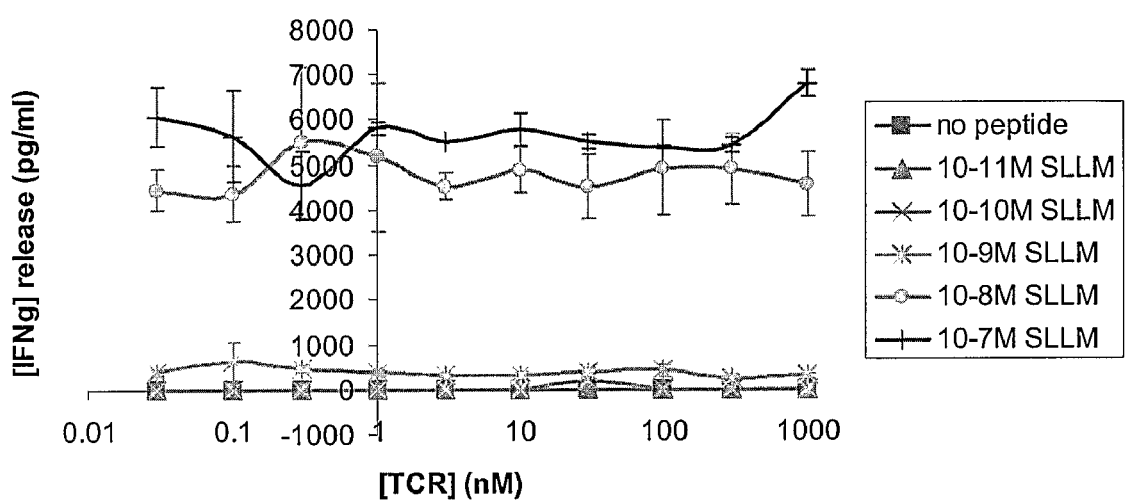
FIG. 20 shows lack of inhibition of T cell activation against peptide pulsed T2 cells by the soluble wild-type 1G4 TCR as measured by IFNγ production.

The soluble high affinity c58c61 1G4 TCR strongly inhibited the activation of 1G4 T cell clones against the peptide-pulsed target cells, as measured by IFN-γ production. Whereas the wild-type 1G4 TCR had no inhibitory effect. (See FIG. 19 for the high affinity c58c61 1G4 TCR and FIG. 20 for the wild-type 1G4 TCR).

Example 11

In-Vivo Tumour Targeting Using a High Affinity c58c61 1G4 TCR-IL-2 Fusion Protein This work was carried out to investigate the ability of a high affinity c58c61 1G4 TCR-IL-2 fusion protein described in Example 6, to inhibit growth of human tumor cells engrafted in nude mice.

Fifty female nude mice (HARLAN, France) were used in this trial.

All animals were injected subcutaneously with the human melanoma tumour-forming cell line (SK-MEL-37) which had been stably transfected with a NY-ESO peptide/ubiquitin minigene construct in ensure enhanced expression of the appropriate class I-peptide target at the cell surface. Tumors were allowed to grow in the animals for 5 days to allow tumour development prior to commencement of treatment.

The rats then received the following i.v. bolus dosage of c58c61 high affinity NY-ESO TCR/IL-2 fusion protein:

Doses ranged between 0.02 and 1.0 mg/kg high affinity 1G4 TCR/IL-2 fusion proteins in PBS, administered at 5, 6, 7, 8, 11, 13, 17, 20, 24, 28, and 30 day post-tumor engraftment. In all experiments, a control treatment group was included where PBS alone was substituted for the TCR/IL-2 immunoconjugate.

Tumor size was then measured using callipers and tumor volume determined according to the following formula ($W^2 \times L$)/2, where W=the smallest diameter of the tumor, and L=is the longest diameter.

Results

Figure 21:
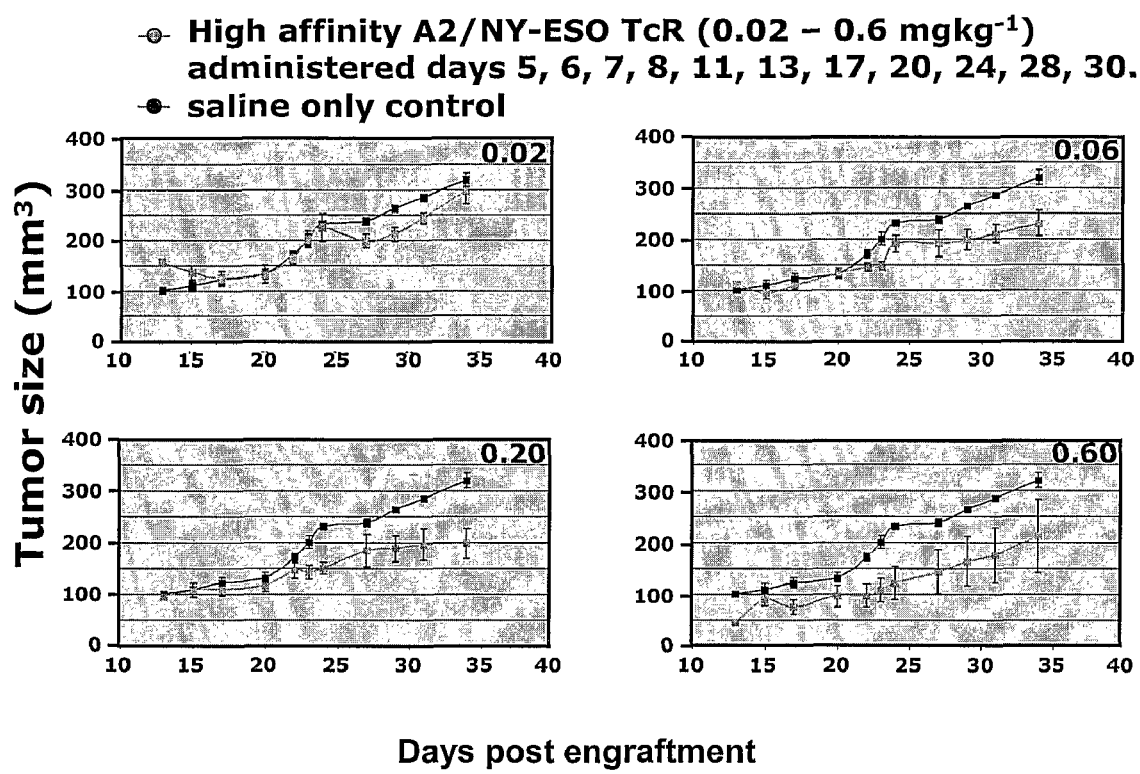
FIG. 21 shows tumor growth inhibition caused by soluble c58c61 high affinity 1G4 TCR-IL-2 immunoconjugates.

The therapeutic effect of the TCR/IL-2 immunoconjugates in terms of tumor growth inhibition is shown in FIG. 21.

Conclusions

The TCR/IL-2 immunoconjugate exhibited a clear dose-dependent anti-tumor effect as shown by the tumour growth curves depicted in FIG. 21.

Example 12

Quantification of Cell Surface TCR Ligands by Fluorescence Microscopy Using High Affinity c58c61 1G4 TCR The number of SLLMWITQC (SEQ ID NO:126)-HLA-A*0201 antigens on cancer cells (Mel 526, Mel 624 and SK-Mel-37 cell lines) was determined (on the assumption that one fluorescence signal relates to a single labelled TCR bound to its cognate pMHC ligand on the surface of the target cell) by single molecule fluorescence microscopy using the high-affinity c58c61 1G4 TCR. This was facilitated by using biotinylated TCR to target the antigen-expressing cancer cells and subsequent labelling of cell-bound TCR by streptavidin-R phycoerythrin (PE) conjugates. Individual PE molecules were then imaged by 3-dimensional fluorescence microscopy.

Staining of adherent cells. The cancer cells were plated into chamber well slides and allowed to adhere overnight in incubator. (37° C., 5% $CO_2$) Media was removed and replaced with fresh R10. Media was removed, and cells washed twice with 500 µl of PBS supplemented with 400 µM $MgCl_2$ (PBS/Mg). Cells were incubated in 200 µl of TCR solution (5 µg $ml^{-1}$ high affinity c58c61 1G4 TCR, or 5 µg $ml^{-1}$ of an "irrelevant" HLA-A2-tax peptide-specific high affinity TCR, in PBS/Mg containing 0.5% BSA albumin) for 30 min at 4° C. TCR solution was removed, and cells were washed three times with 500 µl of PBS/Mg. Cells were incubated in 200 µl of streptavidin-PE solution (5 µg $ml^{-1}$ streptavidin-PE in PBS/Mg containing 0.5% BSA) at room temperature in the dark for 20 min. Streptavidin-PE solution was removed and cells were washed five times with 500 µl of PBS/Mg. Wash media was removed, and cells kept in 400 µl of imaging media before imaging by fluorescence microscopy.

Fluorescence microscopy. Fluorescent microscopy was carried out using an Axiovert 200M (Zeiss) microscope with a 63× Oil objective (Zeiss). A Lambda LS light source containing a 300 W Xenon Arc lamp (Sutter) was used for illumination, and light intensity was reduced to optimal levels by placing a 0.3 and a 0.6 neutral density filter into the light path. Excitation and emission spectra were separated using a TRITC/Dil filter set (Chroma). Cells were imaged in three dimensions by z-stack acquisition (21 planes, 1 µm apart). Image acquisition and analysis was performed using Metamorph software (Universal Imaging) as described (Irvine et al, Nature (419), p 845-9, and Purbhoo et al, Nature Immunology (5), p 524-30).

Results

Figure 22:
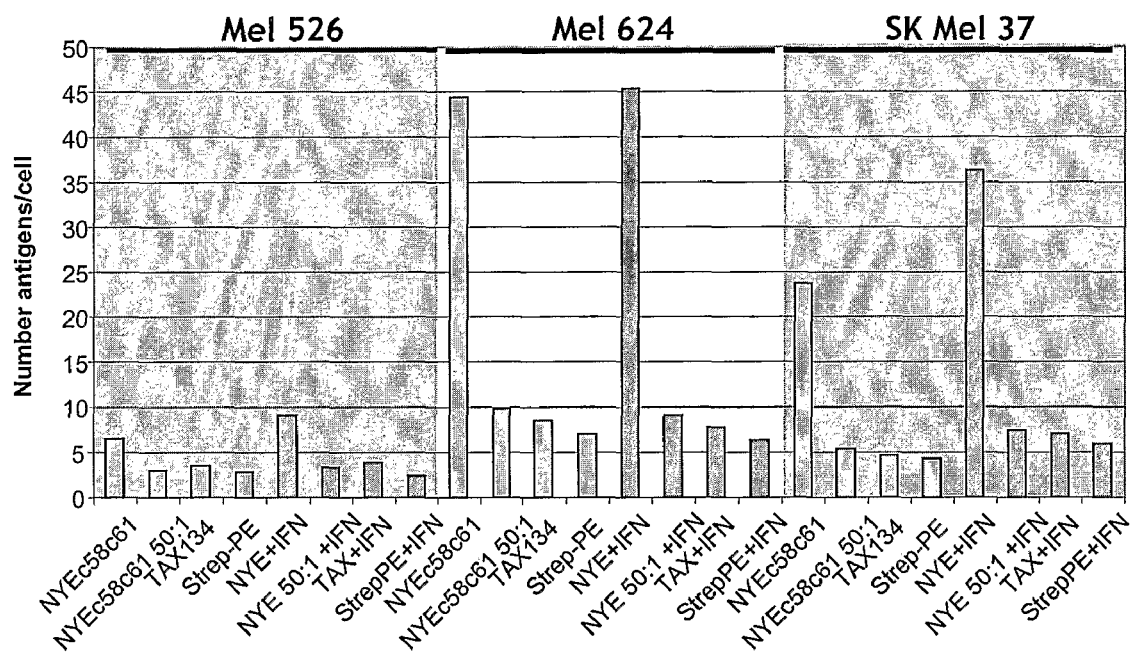
FIG. 22 shows the number of SLLMWITQC (SEQ ID NO:126)-HLA-A*0201 antigens on the surface of Mel 526, Mel 624 and SK-Mel-37 cancer cells as determined by fluorescent microscopy. The visualisation of cell-bound biotinylated soluble c58c61 high affinity 1G4 TCRs was facilitated by conjugation with streptavidin-R phycoerythrin (PE).

As demonstrated by FIG. 22 the above method was used successfully to image high affinity 1G4 TCR bound to SLLMWITQC (SEQ ID NO:126)-HLA-A*0201 antigens on the surface of Mel 526, Mel 624 and SK-Mel-37 cancer cells.

---

The invention claimed is:

1. A recombinant TCR having the α chain extracellular sequence SEQ ID NO:5 and the β chain extracellular sequence SEQ ID NO:6 except that amino acids 95T and 96S of SEQ ID NO:5 are replaced by 95L and 96Y.

2. A recombinant TCR having the α chain extracellular sequence SEQ ID NO:5 and the β chain extracellular sequence SEQ ID NO:6 except that amino acids 95T and 96S of SEQ ID NO:5 are replaced by 95L and 96Y and amino acid T162 of the α chain and amino acid S169 of the β chain are replaced by 162C and 169C and comprising a disulfide bond between α chain 162C and β chain 169C, using the numbering of SEQ ID NOS:5 and 6.

* * * * *

SEQUENCE LISTING

```
<160> NUMBER OF SEQ ID NOS: 127

<210> SEQ ID NO 1
<211> LENGTH: 115
<212> TYPE: PRT
<213> ORGANISM: Homo sapiens

<400> SEQUENCE: 1

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
```

```
              50                   55                     60
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
             100                 105                 110

His Pro Tyr
        115

<210> SEQ ID NO 2
<211> LENGTH: 112
<212> TYPE: PRT
<213> ORGANISM: Homo sapiens

<400> SEQUENCE: 2

Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
                 20                  25                  30

Trp Tyr Arg Gln Asp Pro Gly Met Gly Leu Arg Leu Ile His Tyr Ser
             35                  40                  45

Val Gly Ala Gly Ile Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                 85                  90                  95

Asn Thr Gly Glu Leu Phe Phe Gly Glu Gly Ser Arg Leu Thr Val Leu
             100                 105                 110

<210> SEQ ID NO 3
<211> LENGTH: 627
<212> TYPE: DNA
<213> ORGANISM: Artificial Sequence
<220> FEATURE:
<223> OTHER INFORMATION: synthesized soluble Ig4 TCR alpha chain

<400> SEQUENCE: 3
atgcaggagg tgacacagat tcctgcagct ctgagtgtcc cagaaggaga aaacttggtt      60
ctcaactgca gtttcactga tagcgctatt tacaacctcc agtggtttag gcaggaccct     120
gggaaaggtc tcacatctct gttgcttatt cagtcaagtc agagagagca aacaagtgga     180
agacttaatg cctcgctgga taaatcatca ggacgtagta ctttatacat tgcagcttct     240
cagcctggtg actcagccac ctacctctgt gctgtgaggc ccacatcagg aggaagctac     300
atacctacat tggaagagg aaccagcctt attgttcatc cgtatatcca gaaccctgac     360
cctgccgtgt accagctgag agactctaaa tccagtgaca agtctgtctg cctattcacc     420
gattttgatt tcaaacaaa tgtgtcacaa gtaaggatt ctgatgtgta tatcacagac     480
aaaactgtgc tagacatgag gtctatggac ttcaagagca cagtgctgt ggcctggagc     540 aacaaatctg actttgcatg tgcaaacgcc ttcaacaaca gcattattcc agaagacacc     600
ttcttcccca gcccagaaag ttcctaa                                         627

<210> SEQ ID NO 4
<211> LENGTH: 729
<212> TYPE: DNA
<213> ORGANISM: Artificial Sequence
```

<220> FEATURE:
<223> OTHER INFORMATION: synthesized soluble Ig4 TCR beta chain

<400> SEQUENCE: 4

```
atgggtgtca ctcagacccc aaaattccag gtcctgaaga caggacagag catgacactg    60
cagtgtgccc aggatatgaa ccatgaatac atgtcctggt atcgacaaga cccaggcatg   120
gggctgaggc tgattcatta ctcagttggt gctggtatca ctgaccaagg agaagtcccc   180
aatggctaca atgtctccag atcaaccaca gaggatttcc cgctcaggct gctgtcggct   240
gctccctccc agacatctgt gtacttctgt gccagcagtt acgtcgggaa caccggggag   300
ctgttttttg gagaaggctc taggctgacc gtactggagg acctgaaaaa cgtgttccca   360
cccgaggtcg ctgtgtttga gccatcagaa gcagagatct cccacaccca aaaggccaca   420
ctggtgtgcc tggccacagg cttctacccc gaccacgtgg agctgagctg gtgggtgaat   480
gggaaggagg tgcacagtgg ggtcagcaca gacccgcagc cctcaaggga gcagcccgcc   540
ctcaatgact ccagatacgc tctgagcagc cgcctgaggg tctcggccac cttctgcag   600
gacccccgca accacttccg ctgtcaagtc cagttctacg gctctcgga gaatgacgag   660
tggacccagg atagggccaa acccgtcacc cagatcgtca cgccgaggc ctggggtaga   720
gcagactaa                                                           729
```

<210> SEQ ID NO 5
<211> LENGTH: 208
<212> TYPE: PRT
<213> ORGANISM: Artificial Sequence
<220> FEATURE:
<223> OTHER INFORMATION: synthesized soluble Ig4 TCR alpha chain

<400> SEQUENCE: 5

```
Met Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Gln Ser Ser Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
    130                 135                 140

Gln Thr Asn Val Ser Gln Ser Lys Asp Ser Asp Val Tyr Ile Thr Asp
145                 150                 155                 160

Lys Thr Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205
```

<210> SEQ ID NO 6
<211> LENGTH: 242
<212> TYPE: PRT
<213> ORGANISM: Artificial Sequence
<220> FEATURE:
<223> OTHER INFORMATION: synthesized soluble Ig4 TCR beta chain

<400> SEQUENCE: 6

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Ser Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp
```

<210> SEQ ID NO 7
<211> LENGTH: 627
<212> TYPE: DNA
<213> ORGANISM: Artificial Sequence
<220> FEATURE:
<223> OTHER INFORMATION: synthesized soluble Ig4 TCR alpha chain

<400> SEQUENCE: 7

```
atgcaggagg tgacacagat tcctgcagct ctgagtgtcc cagaaggaga aaacttggtt    60
ctcaactgca gtttcactga tagcgctatt tacaacctcc agtggtttag gcaggaccct   120
gggaaaggtc tcacatctct gttgcttatt cagtcaagtc agagagagca acaagtgga   180 agacttaatg cctcgctgga taatcatca ggacgtagta cttatacat tgcagcttct   240 cagcctggtg actcagccac ctacctctgt gctgtgaggc ccacatcagg aggaagctac   300
atacctacat ttggaagagg aaccagcctt attgttcatc cgtatatcca gaaccctgac   360
cctgccgtgt accagctgag agactctaaa tccagtgaca gtctgtctg cctattcacc   420
```

```
gattttgatt ctcaaacaaa tgtgtcacaa agtaaggatt ctgatgtgta tatcacagac      480
aaatgtgtgc tagacatgag gtctatggac ttcaagagca acagtgctgt ggcctggagc      540
aacaaatctg actttgcatg tgcaaacgcc ttcaacaaca gcattattcc agaagacacc      600
ttcttcccca gcccagaaag ttcctaa                                          627

<210> SEQ ID NO 8
<211> LENGTH: 729
<212> TYPE: DNA
<213> ORGANISM: Artificial Sequence
<220> FEATURE:
<223> OTHER INFORMATION: synthesized soluble Ig4 TCR beta chain

<400> SEQUENCE: 8
atgggtgtca ctcagacccc aaaattccag gtcctgaaga caggacagag catgacactg       60
cagtgtgccc aggatatgaa ccatgaatac atgtcctggt atcgacaaga cccaggcatg      120
gggctgaggc tgattcatta ctcagttggt gctggtatca ctgaccaagg agaagtcccc      180
aatggctaca atgtctccag atcaaccaca gaggatttcc cgctcaggct gctgtcggct      240
gctccctccc agacatctgt gtacttctgt gccagcagtt acgtcgggaa caccggggag      300 ctgtttttg gagaaggctc taggctgacc gtactggagg acctgaaaaa cgtgttccca      360
cccgaggtcg ctgtgtttga gccatcagaa gcagagatct cccacaccca aaaggccaca      420
ctggtgtgcc tggccacagg cttctacccc gaccacgtgg agctgagctg gtgggtgaat      480
gggaaggagg tgcacagtgg ggtctgcaca gacccgcagc ccctcaagga gcagcccgcc      540
ctcaatgact ccagatacgc tctgagcagc cgcctgaggg tctcggccac cttctggcag      600
gacccccgca accacttccg ctgtcaagtc cagttctacg gctctcgga gaatgacgag      660 tggacccagg atagggccaa accgtcacc cagatcgtca gcgccgaggc ctggggtaga      720
gcagactaa                                                              729

<210> SEQ ID NO 9
<211> LENGTH: 208
<212> TYPE: PRT
<213> ORGANISM: Artificial Sequence
<220> FEATURE:
<223> OTHER INFORMATION: synthesized soluble Ig4 TCR alpha chain

<400> SEQUENCE: 9

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr Ile Gln Asn Pro Asp Pro Ala Val Tyr Gln Leu Arg Asp
        115                 120                 125

Ser Lys Ser Ser Asp Lys Ser Val Cys Leu Phe Thr Asp Phe Asp Ser
```

```
                130             135             140
Gln Thr Asn Val Ser Gln Ser Lys Asp Ser Asp Val Tyr Ile Thr Asp
145                 150                 155                 160

Lys Cys Val Leu Asp Met Arg Ser Met Asp Phe Lys Ser Asn Ser Ala
                165                 170                 175

Val Ala Trp Ser Asn Lys Ser Asp Phe Ala Cys Ala Asn Ala Phe Asn
            180                 185                 190

Asn Ser Ile Ile Pro Glu Asp Thr Phe Phe Pro Ser Pro Glu Ser Ser
        195                 200                 205

<210> SEQ ID NO 10
<211> LENGTH: 242
<212> TYPE: PRT
<213> ORGANISM: Artificial Sequence
<220> FEATURE:
<223> OTHER INFORMATION: synthesized soluble Ig4 TCR beta chain

<400> SEQUENCE: 10

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

Glu Asp Leu Lys Asn Val Phe Pro Pro Glu Val Ala Val Phe Glu Pro
        115                 120                 125

Ser Glu Ala Glu Ile Ser His Thr Gln Lys Ala Thr Leu Val Cys Leu
    130                 135                 140

Ala Thr Gly Phe Tyr Pro Asp His Val Glu Leu Ser Trp Trp Val Asn
145                 150                 155                 160

Gly Lys Glu Val His Ser Gly Val Cys Thr Asp Pro Gln Pro Leu Lys
                165                 170                 175

Glu Gln Pro Ala Leu Asn Asp Ser Arg Tyr Ala Leu Ser Ser Arg Leu
            180                 185                 190

Arg Val Ser Ala Thr Phe Trp Gln Asp Pro Arg Asn His Phe Arg Cys
        195                 200                 205

Gln Val Gln Phe Tyr Gly Leu Ser Glu Asn Asp Glu Trp Thr Gln Asp
    210                 215                 220

Arg Ala Lys Pro Val Thr Gln Ile Val Ser Ala Glu Ala Trp Gly Arg
225                 230                 235                 240

Ala Asp

<210> SEQ ID NO 11
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant
```

<400> SEQUENCE: 11

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 12
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 12

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg His Thr Ser
                85                  90                  95

Asn Gly Tyr Phe Pro Pro Thr Phe Gly Arg Gly Thr Ser Leu Ile Val
                100                 105                 110

His Pro Tyr
        115

<210> SEQ ID NO 13
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 13

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Thr
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 14
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 14

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Tyr
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 15
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 15

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ile
                85                  90                  95

-continued

Gly Gly Thr Tyr Ile Pro Thr Phe Gly Arg Gly Thr Ser Leu Ile Val
            100                 105                 110

His Pro Tyr
    115

<210> SEQ ID NO 16
<211> LENGTH: 115
<212> TYPE: PRT
<213> ORGANISM: Artificial Sequence
<220> FEATURE:
<223> OTHER INFORMATION: synthesized high affinity Ig4 TCR variant

<400> SEQUENCE: 16

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Thr
                85                  90                  95

Gly Gly Thr Tyr Ile Pro Thr Phe Gly Arg Gly Thr Ser Leu Ile Val
            100                 105                 110

His Pro Tyr
    115

<210> SEQ ID NO 17
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 17

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Thr
                85                  90                  95

Gly Gly Ser Tyr Ile Pro Thr Phe Gly Arg Gly Thr Ser Leu Ile Val
            100                 105                 110

His Pro Tyr
    115

<210> SEQ ID NO 18
<211> LENGTH: 115
<212> TYPE: PRT
<213> ORGANISM: Artificial Sequence -continued

```
<220> FEATURE:
<223> OTHER INFORMATION: synthesized Ig4 TCR alpha chain variable domain
      variant

<400> SEQUENCE: 18

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Thr
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 19
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 19

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Gln Thr
                85                  90                  95

Val Pro Thr Tyr Ile Pro Thr Phe Gly Arg Gly Thr Ser Leu Ile Val
            100                 105                 110

His Pro Tyr
        115

<210> SEQ ID NO 20
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 20

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
```

```
                    20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ser
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 21
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 21

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Tyr Gln
                85                  90                  95

Ser Gly His Tyr Met Pro Thr Phe Gly Arg Gly Thr Ser Leu Ile Val
            100                 105                 110

His Pro Tyr
        115

<210> SEQ ID NO 22
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 22

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80
```

-continued

Gln Pro Gly Asp Ser Ala Thr Tyr Leu Cys Ala Val Arg Pro Thr Ser
                85                  90                  95

Gly Gly Asp Tyr Thr Pro Thr Phe Gly Arg Gly Thr Ser Leu Ile Val
            100                 105                 110

His Pro Tyr
        115

<210> SEQ ID NO 23
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 23

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Leu
                85                  90                  95

Gly Gly Thr Tyr Ile Pro Thr Phe Gly Arg Gly Thr Ser Leu Ile Val
            100                 105                 110

His Pro Tyr
        115

<210> SEQ ID NO 24
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 24

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Gln
                85                  90                  95

Asp Gly Thr Tyr Ile Pro Thr Phe Gly Arg Gly Thr Ser Leu Ile Val
            100                 105                 110

His Pro Tyr
        115

<210> SEQ ID NO 25
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 25

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Thr
                85                  90                  95

Asp Ser Thr Tyr Ile Pro Thr Phe Gly Arg Gly Thr Ser Leu Ile Val
            100                 105                 110

His Pro Tyr
        115
```

<210> SEQ ID NO 26
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 26

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Val
                85                  90                  95

Asp Pro Thr Tyr Ile Pro Thr Phe Gly Arg Gly Thr Ser Leu Ile Val
            100                 105                 110

His Pro Tyr
        115
```

<210> SEQ ID NO 27
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 27

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Glu Val
                85                  90                  95

Asp Ala Thr Tyr Ile Pro Thr Phe Gly Arg Gly Thr Ser Leu Ile Val
                100                 105                 110

His Pro Tyr
        115

<210> SEQ ID NO 28
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 28

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Glu
                85                  90                  95

Asp Ser Thr Tyr Ile Pro Thr Phe Gly Arg Gly Thr Ser Leu Ile Val
                100                 105                 110

His Pro Tyr
        115

<210> SEQ ID NO 29
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 29

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

```
Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Leu Val
                 85                  90                  95

Gly Gly Val Tyr Ile Pro Thr Phe Gly Arg Gly Thr Ser Leu Ile Val
            100                 105                 110

His Pro Tyr
        115

<210> SEQ ID NO 30
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 30

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Asn Tyr Ile Pro Thr Phe Gly Arg Gly Thr Ser Leu Ile Val
            100                 105                 110

His Pro Tyr
        115

<210> SEQ ID NO 31
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 31

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Thr
                 85                  90                  95

Gly Gly Ser Tyr Ile Pro Thr Phe Gly Arg Gly Thr Ser Leu Ile Val
```

```
                   100                 105                 110

His Pro Tyr
        115

<210> SEQ ID NO 32
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 32

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ile Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 33
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 33

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 34
<211> LENGTH: 115
<212> TYPE: PRT
<213> ORGANISM: Artificial Sequence
```

<220> FEATURE:
<223> OTHER INFORMATION: synthesized Ig4 TCR alpha chain variable domain
     variant

<400> SEQUENCE: 34

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Thr
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 35
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
     variant

<400> SEQUENCE: 35

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Ser Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ile Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 36
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
     variant

<400> SEQUENCE: 36

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn

```
                    20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                    85                  90                  95

Gly Gly Thr Tyr Ile Pro Thr Phe Gly Arg Gly Thr Ser Leu Ile Val
                100                 105                 110

His Pro Tyr
        115

<210> SEQ ID NO 37
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 37

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                    20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ala
                    85                  90                  95

Gly Gly Ser Tyr Ile Pro Ala Phe Gly Arg Gly Thr Ser Leu Ile Val
                100                 105                 110

His Pro Tyr
        115

<210> SEQ ID NO 38
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 38

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                    20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80
```

```
Gln Pro Gly Asp Ser Ala Thr Tyr Leu Cys Ala Val Arg Pro Ala Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 39
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 39

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Thr
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 40
<211> LENGTH: 114
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 40

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Ser Ser Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Gln
                85                  90                  95

Tyr Thr Gln Val Pro Thr Phe Gly Arg Gly Thr Ser Leu Ile Val His
            100                 105                 110

Pro Tyr
```

-continued

```
<210> SEQ ID NO 41
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 41

Met Gln Glu Val Thr Gln Ile Pro Ala Ala Leu Ser Val Pro Glu Gly
1               5                   10                  15

Glu Asn Leu Ala Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Pro Ser Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 42
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 42

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Pro Phe Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 43
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 43
```

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 44
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 44

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Thr Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Thr Ser
                85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 45
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 45

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala

```
                50                  55                  60
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 46
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 46

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Met Gly His Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110

His Pro Tyr
        115

<210> SEQ ID NO 47
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 47

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
             35                  40                  45

Leu Ile Met Gly Thr Gln Arg Glu Gln Thr Ser Gly Arg Leu Asn Ala
         50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Thr Ser
                 85                  90                  95

Gly Gly Ser Tyr Ile Pro Thr Phe Gly Arg Gly Thr Ser Leu Ile Val
                100                 105                 110
```

His Pro Tyr
    115

<210> SEQ ID NO 48
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 48

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Pro Phe Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
    115

<210> SEQ ID NO 49
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 49

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Thr Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
            100                 105                 110

His Pro Tyr
    115

<210> SEQ ID NO 50
<211> LENGTH: 115
<212> TYPE: PRT
<213> ORGANISM: Artificial Sequence
<220> FEATURE:

-continued

<223> OTHER INFORMATION: synthesized Ig4 TCR alpha chain variable domain
      variant

<400> SEQUENCE: 50

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 51
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 51

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Met Gly His Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 52
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 52

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
                35                  40                  45

Leu Ile Met Gly Thr Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 53
<211> LENGTH: 115
<212> TYPE: PRT
<213> ORGANISM: Artificial Sequence
<220> FEATURE:
<223> OTHER INFORMATION: synthesized high affinity variant of Ig4 TCR
      alpha chain variable domain

<400> SEQUENCE: 53

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
                35                  40                  45

Leu Ile Met Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Leu
                85                  90                  95

Asp Gly Thr Tyr Ile Pro Thr Phe Gly Arg Gly Thr Ser Leu Ile Val
                100                 105                 110

His Pro Tyr
        115

<210> SEQ ID NO 54
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 54

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
                35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

```
Gln Pro Gly Asp Ser Ala Thr Tyr Leu Cys Ala Val Arg Pro Leu Arg
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 55
<211> LENGTH: 116
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 55

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Asn Asp
                85                  90                  95

Gly Ser Gly Ser Tyr Ile Pro Thr Phe Gly Arg Gly Thr Ser Leu Ile
            100                 105                 110

Val His Pro Tyr
        115

<210> SEQ ID NO 56
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 56

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Trp
                85                  90                  95

Gly Gly Asn Tyr Ile Pro Thr Phe Gly Arg Gly Thr Ser Leu Ile Val
            100                 105                 110

His Pro Tyr
        115
```

<210> SEQ ID NO 57
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 57

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Glu
                85                  90                  95

Gly Gly Glu Tyr Ile Pro Thr Phe Gly Arg Gly Thr Ser Leu Ile Val
            100                 105                 110

His Pro Tyr
        115
```

<210> SEQ ID NO 58
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 58

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Phe Thr
                85                  90                  95

Gly Gly Gly Tyr Ile Pro Thr Phe Gly Arg Gly Thr Ser Leu Ile Val
            100                 105                 110

His Pro Tyr
        115
```

<210> SEQ ID NO 59
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 59

-continued

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Val Ser
                85                  90                  95

Gly Gly Asp Tyr Ile Pro Thr Phe Gly Arg Gly Thr Ser Leu Ile Val
                100                 105                 110

His Pro Tyr
        115

<210> SEQ ID NO 60
<211> LENGTH: 116
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 60

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Asp
                85                  90                  95

Asp Gly Gly Arg Tyr Ile Pro Thr Phe Gly Arg Gly Thr Ser Leu Ile
                100                 105                 110

Val His Pro Tyr
        115

<210> SEQ ID NO 61
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 61

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala

```
                    50                  55                  60
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Asn Thr
                     85                  90                  95

Gly Gly Gln Tyr Ile Pro Thr Phe Gly Arg Gly Thr Ser Leu Ile Val
                    100                 105                 110

His Pro Tyr
        115

<210> SEQ ID NO 62
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 62

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ile Ala
                     85                  90                  95

Gly Gly Lys Tyr Ile Pro Thr Phe Gly Arg Gly Thr Ser Leu Ile Val
                    100                 105                 110

His Pro Tyr
        115

<210> SEQ ID NO 63
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 63

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Gly Thr
                     85                  90                  95

Gly Gly Asp Tyr Ile Pro Thr Phe Gly Arg Gly Thr Ser Leu Ile Val
                    100                 105                 110
```

His Pro Tyr
        115

<210> SEQ ID NO 64
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 64

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Ala
                85                  90                  95

Gly Gly Ser Asp Ile Pro Thr Phe Gly Arg Gly Thr Ser Leu Ile Val
            100                 105                 110

His Pro Tyr
        115

<210> SEQ ID NO 65
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 65

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Ala
                85                  90                  95

Gly Gly Ala Tyr Ile Pro Thr Phe Gly Arg Gly Thr Ser Leu Ile Val
            100                 105                 110

His Pro Tyr
        115

<210> SEQ ID NO 66
<211> LENGTH: 115
<212> TYPE: PRT
<213> ORGANISM: Artificial Sequence
<220> FEATURE:

```
<223> OTHER INFORMATION: synthesized Ig4 TCR alpha chain variable domain
      variant

<400> SEQUENCE: 66

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Arg
                85                  90                  95

Gly Gly Asp Tyr Ile Pro Thr Phe Gly Arg Gly Thr Ser Leu Ile Val
                100                 105                 110

His Pro Tyr
        115

<210> SEQ ID NO 67
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 67

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Gly
                85                  90                  95

Gly Gly Ile Tyr Ile Pro Thr Phe Gly Arg Gly Thr Ser Leu Ile Val
                100                 105                 110

His Pro Tyr
        115

<210> SEQ ID NO 68
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 68

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30
```

Leu Gln Trp Phe Arg Gln Asp Pro Gly Lys Gly Leu Thr Ser Leu Leu
          35                  40                  45

Leu Ile Ser Pro Trp Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Met Gly
                 85                  90                  95

Gly Gly Arg Tyr Ile Pro Thr Phe Gly Arg Gly Thr Ser Leu Ile Val
             100                 105                 110

His Pro Tyr
        115

<210> SEQ ID NO 69
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 69

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
          35                  40                  45

Leu Ile Gln Gly Trp Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ser Val
                 85                  90                  95

Gly Gly Asn Tyr Ile Pro Thr Phe Gly Arg Gly Thr Ser Leu Ile Val
             100                 105                 110

His Pro Tyr
        115

<210> SEQ ID NO 70
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 70

Met Gln Glu Val Thr Gln Ile Pro Ala Ala Leu Ser Val Pro Glu Gly
1               5                  10                  15

Glu Asn Leu Val Leu Asn Cys Ser Phe Thr Asp Ser Ala Ile Tyr Asn
                 20                  25                  30

Leu Gln Trp Phe Arg Gln Asp Pro Gly Lys Gly Leu Thr Ser Leu Leu
          35                  40                  45

Leu Ile Gln Gly Trp Gln Arg Glu Gln Thr Ser Gly Arg Leu Asn Ala
 50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Thr
                85                  90                  95

Gly Gly Asn Tyr Ile Pro Thr Phe Gly Arg Gly Thr Ser Leu Ile Val
            100                 105                 110

His Pro Tyr
        115

<210> SEQ ID NO 71
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 71

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Thr
                85                  90                  95

Gly Gly Ala Tyr Ile Pro Thr Phe Gly Arg Gly Thr Ser Leu Ile Val
            100                 105                 110

His Pro Tyr
        115

<210> SEQ ID NO 72
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 72

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Ser Pro Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Arg Glu
                85                  90                  95

Ser Gly Asn Tyr Ile Pro Thr Phe Gly Arg Gly Thr Ser Leu Ile Val
            100                 105                 110

His Pro Tyr
        115

<210> SEQ ID NO 73
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 73

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ile Ser
                85                  90                  95

Gly Gly Asp Tyr Ile Pro Thr Phe Gly Arg Gly Thr Ser Leu Ile Val
            100                 105                 110

His Pro Tyr
        115
```

<210> SEQ ID NO 74
<211> LENGTH: 115
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 74

```
Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala His
                85                  90                  95

Asn Gly Asn Tyr Ile Pro Thr Phe Gly Arg Gly Thr Ser Leu Ile Val
            100                 105                 110

His Pro Tyr
        115
```

<210> SEQ ID NO 75
<211> LENGTH: 116
<212> TYPE: PRT
<213> ORGANISM: Artificial Sequence
<220> FEATURE:
<223> OTHER INFORMATION: synthesized Ig4 TCR alpha chain variable domain variant

<400> SEQUENCE: 75

```
Met Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Ser Pro Trp Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Asp Asn
                 85                  90                  95

Thr Trp Gly Thr Tyr Ile Pro Thr Phe Gly Arg Gly Thr Ser Leu Ile
             100                 105                 110

Val His Pro Tyr
        115

<210> SEQ ID NO 76
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 76

Met Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Gln Gly Trp Gln Arg Glu Gln Thr Ser Gly Arg Leu Asn Ala
     50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Val Glu
                 85                  90                  95

Gly Gly Asp Tyr Ile Pro Thr Phe Gly Arg Gly Thr Ser Leu Ile Val
             100                 105                 110

His Pro Tyr
        115

<210> SEQ ID NO 77
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 77

Met Gln Glu Val Thr Gln Ile Pro Ala Ala Leu Ser Val Pro Glu Gly
  1               5                  10                  15

Glu Asn Leu Val Leu Asn Cys Ser Phe Thr Asp Ser Ala Ile Tyr Asn
             20                  25                  30

Leu Gln Trp Phe Arg Gln Asp Pro Gly Lys Gly Leu Thr Ser Leu Leu
         35                  40                  45

Leu Ile Ser Pro Trp Gln Arg Glu Gln Thr Ser Gly Arg Leu Asn Ala
```

```
                50                  55                  60
Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ala Ala
                 85                  90                  95

Ser Gly Asn Tyr Ile Pro Thr Phe Gly Arg Gly Thr Ser Leu Ile Val
                100                 105                 110

His Pro Tyr
        115

<210> SEQ ID NO 78
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 78

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ile Ser
                 85                  90                  95

Gly Gly Glu Tyr Ile Pro Thr Phe Gly Arg Gly Thr Ser Leu Ile Val
                100                 105                 110

His Pro Tyr
        115

<210> SEQ ID NO 79
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 79

Met Gln Glu Val Thr Gln Ile Pro Ala Ala Leu Ser Val Pro Glu Gly
 1               5                  10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Ser Pro Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
 65                  70                  75                  80

Gln Pro Gly Asp Ser Ala Thr Tyr Leu Cys Ala Val Arg Pro Ile Thr
                 85                  90                  95

Gly Gly Gly Tyr Ile Pro Thr Phe Gly Arg Gly Thr Ser Leu Ile Val
                100                 105                 110
```

His Pro Tyr
        115

<210> SEQ ID NO 80
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 80

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Leu Lys
                85                  90                  95

Gly Gly Ala Tyr Ile Pro Thr Phe Gly Arg Gly Thr Ser Leu Ile Val
            100                 105                 110

His Pro Tyr
        115

<210> SEQ ID NO 81
<211> LENGTH: 115
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 81

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
            20                  25                  30

Leu Gln Trp Phe Arg Gln Asp Pro Gly Lys Gly Leu Thr Ser Leu Leu
        35                  40                  45

Leu Ile Gln Gly Trp Gln Arg Glu Gln Thr Ser Gly Arg Leu Asn Ala
    50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ala Glu
                85                  90                  95

Gly Gly Ser Tyr Ile Pro Thr Phe Gly Arg Gly Thr Ser Leu Ile Val
            100                 105                 110

His Pro Tyr
        115

<210> SEQ ID NO 82
<211> LENGTH: 115
<212> TYPE: PRT
<213> ORGANISM: Artificial Sequence
<220> FEATURE:

-continued

<223> OTHER INFORMATION: synthesized Ig4 TCR alpha chain variable domain
      variant

<400> SEQUENCE: 82

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Ser Thr
                85                  90                  95

Gly Gly Asn Tyr Ile Pro Thr Phe Gly Arg Gly Thr Ser Leu Ile Val
                100                 105                 110

His Pro Tyr
        115

<210> SEQ ID NO 83
<211> LENGTH: 116
<212> TYPE: PRT
<213> ORGANISM: Artificial Sequence
<220> FEATURE:
<223> OTHER INFORMATION: synthesized Ig4 TCR alpha chain variable domain
      variant

<400> SEQUENCE: 83

Met Gln Glu Val Thr Gln Ile Pro Ala Ala Leu Ser Val Pro Glu Gly
1               5                   10                  15

Glu Asn Leu Val Leu Asn Cys Ser Phe Thr Asp Ser Ala Ile Tyr Asn
                20                  25                  30

Leu Gln Trp Phe Arg Gln Asp Pro Gly Lys Gly Leu Thr Ser Leu Leu
            35                  40                  45

Leu Ile Gln Gly Trp Gln Arg Glu Gln Thr Ser Gly Arg Leu Asn Ala
        50                  55                  60

Ser Leu Asp Lys Ser Ser Gly Arg Ser Thr Leu Tyr Ile Ala Ala Ser
65                  70                  75                  80

Gln Pro Gly Asp Ser Ala Thr Tyr Leu Cys Ala Val Arg Pro Val Asp
                85                  90                  95

Asp Gly Gly Lys Tyr Ile Pro Thr Phe Gly Arg Gly Thr Ser Leu Ile
                100                 105                 110

Val His Pro Tyr
        115

<210> SEQ ID NO 84
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 84

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
          35                  40                  45

Val Gly Ala Gly Thr Thr Asp Arg Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asn Thr Gly Glu Leu Phe Phe Gly Gly Ser Arg Leu Thr Val Leu
             100                 105                 110

<210> SEQ ID NO 85
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 85

Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
             20                  25                  30

Trp Tyr Arg Gln Asp Pro Gly Met Gly Leu Arg Leu Ile His Tyr Ser
          35                  40                  45

Val Gly Ala Gly Thr Thr Asp Gln Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asn Thr Gly Glu Leu Phe Phe Gly Glu Gly Ser Arg Leu Thr Val Leu
             100                 105                 110

<210> SEQ ID NO 86
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 86

Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
             20                  25                  30

Trp Tyr Arg Gln Asp Pro Gly Met Gly Leu Arg Leu Ile His Tyr Ser
          35                  40                  45

Val Gly Ala Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Asn Val Gly
                 85                  90                  95

Asn Thr Gly Glu Leu Phe Phe Gly Glu Gly Ser Arg Leu Thr Val Leu
             100                 105                 110

<210> SEQ ID NO 87
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 87

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Gly Thr Gly Glu Leu Phe Phe Gly Glu Gly Ser Arg Leu Thr Val Leu
            100                 105                 110

<210> SEQ ID NO 88
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 88

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Ile Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 89
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 89

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asp Thr Gly Glu Leu Phe Phe Gly Glu Gly Ser Arg Leu Thr Val Leu
                100                 105                 110

<210> SEQ ID NO 90
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 90

Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
        35                  40                  45

Val Gly Val Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asp Thr Gly Glu Leu Phe Phe Gly Glu Gly Ser Arg Leu Thr Val Leu
                100                 105                 110

<210> SEQ ID NO 91
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 91

Met Gly Val Thr Gln Thr Pro Lys Phe Gln Val Leu Lys Thr Gly Gln
 1               5                  10                  15

Ser Val Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
        35                  40                  45

Val Gly Val Gly Thr Thr Asp Gln Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asp Thr Gly Glu Leu Phe Phe Gly Glu Gly Ser Arg Leu Thr Val Leu
                100                 105                 110

```
<210> SEQ ID NO 92
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 92

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ser Val Gly Met Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 93
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 93

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Thr Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 94
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 94

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30
```

Trp Tyr Arg Gln Asp Pro Gly Met Gly Leu Arg Leu Ile His Tyr Ser
                35                  40                  45

Val Ala Ile Gln Thr Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asn Thr Gly Glu Leu Phe Phe Gly Gly Gly Ser Arg Leu Thr Val Leu
                100                 105                 110

<210> SEQ ID NO 95
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 95

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
                35                  40                  45

Val Ser Val Gly Met Thr Asp Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asn Thr Gly Glu Leu Phe Phe Gly Glu Gly Ser Arg Leu Thr Val Leu
                100                 105                 110

<210> SEQ ID NO 96
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 96

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
                20                  25                  30

Trp Tyr Arg Gln Asp Pro Gly Met Gly Leu Arg Leu Ile His Tyr Ser
                35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Val Thr Gly Glu Leu Phe Phe Gly Glu Gly Ser Arg Leu Thr Val Leu
                100                 105                 110

<210> SEQ ID NO 97
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 97

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asp Thr Gly Glu Leu Phe Phe Gly Glu Gly Ser Arg Leu Thr Val Leu
            100                 105                 110

<210> SEQ ID NO 98
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 98

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Gly Ala Gly Thr Thr Asp Arg Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Leu Gly
                85                  90                  95

Asp Thr Gly Glu Leu Phe Phe Gly Glu Gly Ser Arg Leu Thr Val Leu
            100                 105                 110

<210> SEQ ID NO 99
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 99

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Gly Ala Gly Thr Thr Asp Arg Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Phe Val Gly
                85                  90                  95

Asp Thr Gly Glu Leu Phe Phe Gly Gly Gly Ser Arg Leu Thr Val Leu
                100                 105                 110

<210> SEQ ID NO 100
<211> LENGTH: 47
<212> TYPE: PRT
<213> ORGANISM: Artificial Sequence
<220> FEATURE:
<223> OTHER INFORMATION: synthesized soluble TRAC

<400> SEQUENCE: 100

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys
            35                  40                  45

<210> SEQ ID NO 101
<211> LENGTH: 56
<212> TYPE: PRT
<213> ORGANISM: Artificial Sequence
<220> FEATURE:
<223> OTHER INFORMATION: synthesized soluble TRBC1

<400> SEQUENCE: 101

Glu Asp Leu Asn Lys Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Phe Pro Asp His Val Glu Leu Ser Trp Trp Val Asn
            35                  40                  45

Gly Lys Glu Val His Ser Gly Val
 50                  55

<210> SEQ ID NO 102
<211> LENGTH: 56
<212> TYPE: PRT
<213> ORGANISM: Artificial Sequence
<220> FEATURE:
<223> OTHER INFORMATION: synthesized soluble TRBC2

<400> SEQUENCE: 102

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val
 50                  55

```
<210> SEQ ID NO 103
<211> LENGTH: 30
<212> TYPE: PRT
<213> ORGANISM: Artificial Sequence
<220> FEATURE:
<223> OTHER INFORMATION: scTCR linker

<400> SEQUENCE: 103

Pro Gly Gly Gly Ser Gly Gly Gly Ser Gly Gly Gly Ser Gly
1               5                   10                  15

Gly Gly Ser Gly Gly Gly Ser Gly Gly Gly Pro
            20                  25                  30

<210> SEQ ID NO 104
<211> LENGTH: 35
<212> TYPE: PRT
<213> ORGANISM: Artificial Sequence
<220> FEATURE:
<223> OTHER INFORMATION: scTCR linker

<400> SEQUENCE: 104

Pro Gly Gly Gly Ser Gly Gly Gly Ser Gly Gly Gly Ser Gly
1               5                   10                  15

Gly Gly Ser Gly Gly Gly Ser Gly Gly Gly Ser Gly Gly
            20                  25                  30

Gly Gly Pro
        35

<210> SEQ ID NO 105
<211> LENGTH: 37
<212> TYPE: DNA
<213> ORGANISM: Artificial Sequence
<220> FEATURE:
<223> OTHER INFORMATION: Primer

<400> SEQUENCE: 105
tctctcatta atgaaacagg aggtgacgca gattcct                              37

<210> SEQ ID NO 106
<211> LENGTH: 20
<212> TYPE: DNA
<213> ORGANISM: Artificial Sequence
<220> FEATURE:
<223> OTHER INFORMATION: Primer

<400> SEQUENCE: 106
cggcagggtc agggttctgg                                                 20

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
ccagaaccct gaccctgccg                                                 20

<210> SEQ ID NO 108
<211> LENGTH: 30
<212> TYPE: DNA
<213> ORGANISM: Artificial Sequence
<220> FEATURE:
<223> OTHER INFORMATION: Primer

<400> SEQUENCE: 108
```

```
aagcttcccg ggggaacttt ctgggctggg                                          30
```

<210> SEQ ID NO 109
<211> LENGTH: 36
<212> TYPE: DNA
<213> ORGANISM: Artificial Sequence
<220> FEATURE:
<223> OTHER INFORMATION: Primer

<400> SEQUENCE: 109

```
tctctcatta atgaatgctg gtgtcactca gacccc                                   36
```

<210> SEQ ID NO 110
<211> LENGTH: 22
<212> TYPE: DNA
<213> ORGANISM: Artificial Sequence
<220> FEATURE:
<223> OTHER INFORMATION: Primer

<400> SEQUENCE: 110

```
cttctgatgg ctcaaacaca gc                                                  22
```

<210> SEQ ID NO 111
<211> LENGTH: 22
<212> TYPE: DNA
<213> ORGANISM: Artificial Sequence
<220> FEATURE:
<223> OTHER INFORMATION: Primer

<400> SEQUENCE: 111

```
gctgtgtttg agccatcaga ag                                                  22
```

<210> SEQ ID NO 112
<211> LENGTH: 30
<212> TYPE: DNA
<213> ORGANISM: Artificial Sequence
<220> FEATURE:
<223> OTHER INFORMATION: Primer

<400> SEQUENCE: 112

```
aagcttcccg gggtctgctc tacccaggc                                           30
```

<210> SEQ ID NO 113
<211> LENGTH: 3342
<212> TYPE: DNA
<213> ORGANISM: Artificial Sequence
<220> FEATURE:
<223> OTHER INFORMATION: pEX954 Vector

<400> SEQUENCE: 113

```
gatctcgatc ccgcgaaatt aatacgactc actatagga gaccacaacg gtttccctct          60
agaaataatt ttgtttaact ttaagaagga gatataatcg atgtctaact cgagtgacaa        120
gtctgtctgc ctattcaccg attttgattc tcaaacaaat gtgtcacaaa gtaaggattc        180
tgatgtgtat atcacagaca aatgtgtgct agacatgagg tctatggact tcaagagcaa        240
cagtgctgtg gcctggagca acaaatctga ctttgcatgt gcaaacgcct tcaacaacag        300
cattattcca gaagacacct tcttccccag cccagaaagt tcctaagctt gaattccgat        360
ccggctgcta acaaagcccg aaaggaagct gagttggctg ctgccaccgc tgagcaataa        420
ctagcataac ccctgggggc tctaaacgg tcttgaggg gttttttgct gaaaggagga        480
actatatccg gataattctt gaagacgaaa gggcctcgtg atacgcctat ttttataggt        540
taatgtcatg ataataatgg tttcttagac gtgaggtggc acttttcggg gaaatgtgcg        600
```

```
cggaacccct atttgtttat ttttctaaat acattcaaat atgtatccgc tcatgagaca    660
ataaccctga taaatgcttc aataatattt tgttaaaatt cgcgttaaat ttttgttaaa    720
tcagctcatt ttttaaccaa taggccgaaa tcggcaaaat cccttataaa tcaaaagaat    780
agaccgagat agggttgagt gttgttccag tttggaacaa gagtccacta ttaaagaacg    840
tggactccaa cgtcaaaggg cgaaaaaccg tctatcaggg cgatggccca ctacgtgaac    900
catcacccta atcaagtttt tggggtcga ggtgccgtaa agcactaaat cggaacccta    960
aagggagccc ccgatttaga gcttgacggg gaaagccggc gaacgtggcg agaaaggaag   1020
ggaagaaagc gaaaggagcg ggcgctaggg cgctggcaag tgtagcggtc acgctgcgcg   1080
taaccaccac acccgccgcg cttaatgcgc cgctacaggg cgcgtcaggt ggcacttttc   1140
ggggaaatgt gcgcggaacc cctatttgtt tatttttcta aatacattca aatatgtatc   1200
cgctcatgag acaataaccc tgataaatgc ttcaataata ttgaaaaagg aagagtatga   1260
gtattcaaca tttccgtgtc gcccttattc ccttttttgc ggcattttgc cttcctgttt   1320
ttgctcaccc agaaacgctg gtgaaagtaa aagatgctga agatcagttg ggtgcacgag   1380
tgggttacat cgaactggat ctcaacagcg gtaagatcct tgagagtttt cgccccgaag   1440
aacgttttcc aatgatgagc acttttaaag ttctgctatg tggcgcggta ttatcccgtg   1500
ttgacgccgg gcaagagcaa ctcggtcgcc gcatacacta ttctcagaat gacttggttg   1560
agtactcacc agtcacagaa aagcatctta cggatggcat gacagtaaga gaattatgca   1620
gtgctgccat aaccatgagt gataacactg cggccaactt acttctgaca acgatcggag   1680
gaccgaagga gctaaccgct tttttgcaca acatggggga tcatgtaact cgccttgatc   1740
gttgggaacc ggagctgaat gaagccatac caaacgacga gcgtgacacc acgatgcctg   1800
cagcaatggc aacaacgttg cgcaaactat taactggcga actacttact ctagcttccc   1860
ggcaacaatt aatagactgg atggaggcgg ataaagttgc aggaccactt ctgcgctcgg   1920
cccttccggc tggctggttt attgctgata atctggagc cggtgagcgt gggtctcgcg   1980
gtatcattgc agcactgggg ccagatggta agccctcccg tatcgtagtt atctacacga   2040
cggggagtca ggcaactatg gatgaacgaa atagacagat cgctgagata ggtgcctcac   2100
tgattaagca ttggtaactg tcagaccaag tttactcata tatactttag attgatttaa   2160
aacttcattt ttaatttaaa aggatctagg tgaagatcct ttttgataat ctcatgacca   2220
aaatccctta acgtgagttt tcgttccact gagcgtcaga ccccgtagaa aagatcaaag   2280
gatcttcttg agatcctttt tttctgcgcg taatctgctg cttgcaaaca aaaaaaccac   2340
cgctaccagc ggtggtttgt ttgccggatc aagagctacc aactcttttt ccgaaggtaa   2400
ctggcttcag cagagcgcag ataccaaata ctgtccttct agtgtagccg tagttaggcc   2460
accacttcaa gaactctgta gcaccgccta catacctcgc tctgctaatc ctgttaccag   2520
tggctgctgc cagtggcgat aagtcgtgtc ttaccgggtt ggactcaaga cgatagttac   2580
cggataaggc gcagcggtcg ggctgaacgg ggggttcgtg cacacagccc agcttggagc   2640
gaacgaccta caccgaactg agatacctac agcgtgagct atgagaaagc gccacgcttc   2700
ccgaagggag aaaggcggac aggtatccgg taagcggcag ggtcggaaca ggagagcgca   2760
cgagggagct tccaggggga aacgcctggt atctttatag tcctgtcggg tttcgccacc   2820
tctgacttga gcgtcgattt tgtgatgct cgtcaggggg cggagccta tggaaaaacg   2880 ccagcaacgc ggccttttta cggttcctgg ccttttgctg ccttttgct cacatgttct   2940 ttcctgcgtt atcccctgat tctgtggata accgtattac cgcctttgag tgagctgata   3000
```

-continued

| | |
|---|---|
| ccgctcgccg cagccgaacg accgagcgca gcgagtcagt gagcgaggaa gcggaagagc | 3060 |
| gcctgatgcg gtatttctc cttacgcatc tgtgcggtat ttcacccgc aatggtgcac | 3120 |
| tctcagtaca atctgctctg atgccgcata gttaagccag tatacactcc gctatcgcta | 3180 |
| cgtgactggg tcatggctgc gccccgacac ccgccaacac ccgctgacgc gccctgacgg | 3240 |
| gcttgtctgc tcccggcatc cgcttacaga caagctgtga ccgtctccgg gagctgcatg | 3300 |
| tgtcagaggt tttcaccgtc atcaccgaaa cgcgcgaggc ag | 3342 |

<210> SEQ ID NO 114
<211> LENGTH: 3836
<212> TYPE: DNA
<213> ORGANISM: Artificial Sequence
<220> FEATURE:
<223> OTHER INFORMATION: pEX821 Vector

<400> SEQUENCE: 114

| | |
|---|---|
| gatctcgatc ccgcgaaatt aatacgactc actatagggc gaccacaacg gtttccctct | 60 |
| agaaataatt ttgtttaact ttaagaagga gatatacata tgaacgctgg tgtcactcag | 120 |
| accccaaaat tccaggtcct gaagacagga cagagcatga cactgcagtg tgcccaggat | 180 |
| atgaaccatg aatacatgtc ctggtatcga caagacccag gcatggggct gaggctgatt | 240 |
| cattactcag ttggtgctgg tatcactgac caaggagaag tccccaatgg ctacaatgtc | 300 |
| tccagatcaa ccacagagga tttcccgctc aggctgctgt cggctgctcc ctcccagaca | 360 |
| tctgtgtact ctgtgccag caggcccgga ctagcgggag gcgaccaga gcagtacttc | 420 |
| gggccgggca ccaggctcac ggtcacagag gacctgaaaa acgtgttccc acccgaggtc | 480 |
| gctgtgtttg agccatcaga agcagagatc tcccacaccc aaaaggccac actggtgtgc | 540 |
| ctggccaccg gtttctaccc cgaccacgtg agctgagctg gtgggtgaa tgggaaggag | 600 |
| gtgcacagtg gggtctgcac agacccgcag cccctcaagg agcagcccgc ctcaatgac | 660 |
| tccagatacg ctctgagcag ccgcctgagg gtctcggcca ccttctggca ggaccccgc | 720 |
| aaccacttcc gctgtcaagt ccagttctac gggctctcgg agaatgacga gtggaccag | 780 |
| gatagggcca aacccgtcac ccagatcgtc agcgccgagg cctggggtag agcagactaa | 840 |
| gcttgaattc cgatccggct gctaacaaag cccgaaagga agctgagttg gctgctgcca | 900 |
| ccgctgagca ataactagca taaccccttg ggcctctaa acgggtcttg agggttttt | 960 |
| tgctgaaagg aggaactata tccggataat tcttgaagac gaaagggcct cgtgatacgc | 1020 |
| ctatttttat aggttaatgt catgataata atggtttctt agacgtcagg tggcactttt | 1080 |
| cggggaaatg tgcgcggaac ccctatttgt ttattttct aaatacattc aaatatgtat | 1140 |
| ccgctcatga caataaacc ctgataaatg cttcaataat attttgttaa aattcgcgtt | 1200 |
| aaatttttgt taaatcagct catttttaa ccataggcc gaaatcggca aaatccctta | 1260 |
| taaatcaaaa gaatagaccg agatagggtt gagtgttgtt ccagtttgga caagagtcc | 1320 |
| actattaaag aacgtggact ccaacgtcaa agggcgaaaa accgtctatc agggcgatgg | 1380 |
| cccactacgt gaaccatcac cctaatcaag ttttttgggg tcgaggtgcc gtaaagcact | 1440 |
| aaatcggaac cctaaaggga gcccccgatt tagagcttga cggggaaagc cggcgaacgt | 1500 |
| ggcgagaaag gaagggaaga aagcgaaagg agcgggcgct agggcgctgg caagtgtagc | 1560 |
| ggtcacgctg cgcgtaacca ccacacccgc cgcgcttaat gcgccgctac agggcgcgtc | 1620 |
| aggtggcact tttcggggaa atgtgcgcgg aacccctatt tgtttattt tctaaataca | 1680 |
| ttcaaatatg tatccgctca tgagacaata accctgataa atgcttcaat aatattgaaa | 1740 |

```
aaggaagagt atgagtattc aacatttccg tgtcgccctt attccctttt ttgcggcatt    1800
ttgccttcct gtttttgctc acccagaaac gctggtgaaa gtaaaagatg ctgaagatca    1860
gttgggtgca cgagtgggtt acatcgaact ggatctcaac agcggtaaga tccttgagag    1920
ttttcgcccc gaagaacgtt ttccaatgat gagcactttt aaagttctgc tatgtggcgc    1980
ggtattatcc cgtgttgacg ccgggcaaga gcaactcggt cgccgcatac actattctca    2040
gaatgacttg gttgagtact caccagtcac agaaaagcat cttacggatg gcatgacagt    2100
aagagaatta tgcagtgctg ccataaccat gagtgataac actgcggcca acttacttct    2160
gacaacgatc ggaggaccga aggagctaac cgcttttttg cacaacatgg ggatcatgt     2220 aactcgcctt gatcgttggg aaccggagct gaatgaagcc ataccaaacg acgagcgtga    2280
caccacgatg cctgcagcaa tggcaacaac gttgcgcaaa ctattaactg gcgaactact    2340
tactctagct tcccggcaac aattaataga ctggatggag gcggataaag ttgcaggacc    2400
acttctgcgc tcggcccttc cggctggctg gtttattgct gataaatctg gagccggtga    2460
gcgtgggtct cgcggtatca ttgcagcact ggggccagat ggtaagccct cccgtatcgt    2520
agttatctac acgacgggga gtcaggcaac tatggatgaa cgaaatagac agatcgctga    2580
gataggtgcc tcactgatta agcattggta actgtcagac caagtttact catatatact    2640
ttagattgat ttaaaacttc attttttaatt taaaaggatc taggtgaaga tcctttttga    2700
taatctcatg accaaaatcc cttaacgtga gttttcgttc cactgagcgt cagaccccgt    2760
agaaaagatc aaaggatctt cttgagatcc ttttttttctg cgcgtaatct gctgcttgca    2820
aacaaaaaaa ccaccgctac cagcggtggt ttgtttgccg gatcaagagc taccaactct    2880 tttttccgaag gtaactggct tcagcagagc gcagatacca aatactgtcc ttctagtgta    2940
gccgtagtta ggccaccact tcaagaactc tgtagcaccg cctacatacc tcgctctgct    3000
aatcctgtta ccagtggctg ctgccagtgg cgataagtcg tgtcttaccg ggttggactc    3060
aagacgatag ttaccggata aggcgcagcg gtcgggctga acggggggtt cgtgcacaca    3120
gcccagcttg gagcgaacga cctacaccga actgagatac ctacagcgtg agctatgaga    3180
aagcgccacg cttcccgaag ggagaaaggc ggacaggtat ccggtaagcg gcagggtcgg    3240
aacaggagag cgcacgaggg agcttccagg gggaaacgcc tggtatcttt atagtcctgt    3300
cgggtttcgc cacctctgac ttgagcgtcg attttttgtga tgctcgtcag ggggcggag    3360 cctatggaaa aacgccagca acgcggcctt tttacggttc ctggccttttt gctggccttt    3420 tgctcacatg ttctttcctg cgttatcccc tgattctgtg gataaccgta ttaccgcctt    3480
tgagtgagct gataccgctc gccgcagccg aacgaccgag cgcagcgagt cagtgagcga    3540
ggaagcggaa gagcgcctga tgcggtattt tctccttacg catctgtgcg gtatttcaca    3600
ccgcaatggt gcactctcag tacaatctgc tctgatgccg catagttaag ccagtataca    3660
ctccgctatc gctacgtgac tgggtcatgg ctgcgccccg acacccgcca cacccgctg     3720 acgcgccctg acgggcttgt ctgctcccgg catccgctta cagacaagct gtgaccgtct    3780
ccgggagctg catgtgtcag aggttttcac cgtcatcacc gaaacgcgcg aggcag        3836
```

<210> SEQ ID NO 115
<211> LENGTH: 3857
<212> TYPE: DNA
<213> ORGANISM: Artificial Sequence
<220> FEATURE:
<223> OTHER INFORMATION: pEX202 Vector

<400> SEQUENCE: 115

```
gatctcgatc ccgcgaaatt aatacgactc actataggga gaccacaacg gtttccctct    60
agaaataatt ttgtttaact ttaagaagga gatatacata tgcagaagga agtggagcag   120
aactctggac ccctcagtgt tccagaggga gccattgcct ctctcaactg cacttacagt   180
gaccgaggtt cccagtcctt cttctggtac agacaatatt ctgggaaaag ccctgagttg   240
ataatgtcca tatactccaa tggtgacaaa gaagatggaa ggtttacagc acagctcaat   300
aaagccagcc agtatgtttc tctgctcatc agagactccc agcccagtga ttcagccacc   360
tacctctgtg ccgttacaac tgacagctgg gggaaattgc agtttggagc agggacccag   420
gttgtggtca ccccagatat ccagaaccct gaccctgccg tgtaccagct gagagactct   480
aaatccagtg acaagtctgt ctgcctattc accgattttg attctcaaac aaatgtgtca   540
caaagtaagg attctgatgt gtatatcaca gacaaaactg tgctagacat gaggtctatg   600
gacttcaaga gcaacagtgc tgtggcctgg agcaacaaat ctgactttgc atgtgcaaac   660
gccttcaaca acagcattat tccagaagac accttcttcc ccagcccaga aagttccccc   720
gggggtagaa tcgcccggct ggaggaaaaa gtgaaaacct tgaaagctca gaactcggag   780
ctggcgtcca cggccaacat gctcaggaa caggtggcac agcttaaaca gaaagtcatg   840
aactactagg atccatggta agcttgaatt ccgatccggc tgctaacaaa gcccgaaagg   900
aagctgagtt ggctgctgcc accgctgagc aataactagc ataaccccctt ggggcctcta   960
aacgggtctt gaggggtttt ttgctgaaag gaggaactat atccggataa ttcttgaaga  1020
cgaaagggcc tcgtgatacg cctattttta taggttaatg tcatgataat aatggtttct  1080
tagacgtcag gtggcacttt tcggggaaat gtgcgcggaa cccctatttg tttatttttc  1140
taaatacatt caaatatgta tccgctcatg agacaataac cctgataaat gcttcaataa  1200
tattttgtta aaattcgcgt taaattttttg ttaaatcagc tcattttttta accaataggc  1260
cgaaatcggc aaaatccctt ataaatcaaa agaatagacc gagataggt tgagtgttgt  1320
tccagtttgg aacaagagtc cactattaaa gaacgtggac tccaacgtca aagggcgaaa  1380
aaccgtctat cagggcgatg gcccactacg tgaaccatca ccctaatcaa gttttttggg  1440
gtcgaggtgc cgtaaagcac taaatcgaa ccctaaaggg agcccccgat ttagagcttg  1500
acggggaaag ccggcgaacg tggcgagaaa ggaagggaag aaagcgaaag gagcgggcgc  1560
tagggcgctg gcaagtgtag cggtcacgct gcgcgtaacc accacacccg ccgcgcttaa  1620
tgcgccgcta cagggcgcgt caggtggcac ttttcgggga aatgtgcgcg gaaccccctat  1680
ttgtttattt ttctaaatac attcaaatat gtatccgctc atgagacaat aaccctgata  1740
aatgcttcaa taatattgaa aaggaagag tatgagtatt caacatttcc gtgtcgccct  1800
tattcccttt tttgcggcat tttgccttcc tgttttttgct cacccagaaa cgctggtgaa  1860
agtaaaagat gctgaagatc agttgggtgc acgagtgggt tacatcgaac tggatctcaa  1920
cagcggtaag atccttgaga gttttcgccc cgaagaacgt tttccaatga tgagcacttt  1980
taaagttctg ctatgtggcg cggtattatc ccgtgttgac gccgggcaag agcaactcgg  2040
tcgccgcata cactattctc agaatgactt ggttgagtac tcaccagtca cagaaaagca  2100
tcttacggat ggcatgacag taagagaatt atgcagtgct gccataacca tgagtgataa  2160
cactgcggcc aacttacttc tgacaacgat cggaggaccg aaggagctaa ccgcttttt  2220
gcacaacatg ggggatcatg taactcgcct tgatcgttgg gaaccggagc tgaatgaagc  2280
cataccaaac gacgagcgtg acaccacgat gcctgcagca atggcaacaa cgttgcgcaa  2340
actattaact ggcgaactac ttactctagc ttcccggcaa caattaatag actggatgga  2400
```

```
ggcggataaa gttgcaggac cacttctgcg ctcggccctt ccggctggct ggtttattgc    2460
tgataaatct ggagccggtg agcgtgggtc tcgcggtatc attgcagcac tggggccaga    2520
tggtaagccc tcccgtatcg tagttatcta cacgacgggg agtcaggcaa ctatggatga    2580
acgaaataga cagatcgctg ataggtgcc tcactgatt aagcattggt aactgtcaga    2640
ccaagtttac tcatatatac tttagattga tttaaaactt cattttaat ttaaaaggat    2700 ctaggtgaag atccttttg ataatctcat gaccaaaatc ccttaacgtg agttttcgtt    2760
ccactgagcg tcagaccccg tagaaaagat caaaggatct tcttgagatc ctttttttct    2820
gcgcgtaatc tgctgcttgc aaacaaaaaa accaccgcta ccagcggtgg tttgtttgcc    2880
ggatcaagag ctaccaactc tttttccgaa ggtaactggc ttcagcagag cgcagatacc    2940
aaatactgtc cttctagtgt agccgtagtt aggccaccac ttcaagaact ctgtagcacc    3000
gcctacatac ctcgctctgc taatcctgtt accagtggct gctgccagtg gcgataagtc    3060
gtgtcttacc gggttggact caagacgata gttaccggat aaggcgcagc ggtcgggctg    3120
aacggggggt tcgtgcacac agcccagctt ggagcgaacg acctacaccg aactgagata    3180
cctacagcgt gagctatgag aaagcgccac gcttcccgaa gggagaaagg cggacaggta    3240
tccggtaagc ggcagggtcg aacaggaga gcgcacgagg gagcttccag ggggaaacgc    3300
ctggtatctt tatagtcctg tcgggtttcg ccacctctga cttgagcgtc gatttttgtg    3360
atgctcgtca gggggcgga gcctatggaa aaacgccagc aacgcggcct ttttacggtt    3420
cctggccttt tgctggcctt tgctcacat gttctttcct gcgttatccc ctgattctgt    3480
ggataaccgt attaccgcct tgagtgagc tgataccgct cgccgcagcc gaacgaccga    3540
gcgcagcgag tcagtgagcg aggaagcgga agagcgcctg atgcggtatt ttctccttac    3600
gcatctgtgc ggtatttcac accgcaatgg tgcactctca gtacaatctg ctctgatgcc    3660
gcatagttaa gccagtatac actccgctat cgctacgtga ctgggtcatg gctgcgcccc    3720
gacacccgcc aacacccgct gacgcgccct gacgggcttg tctgctcccg gcatccgctt    3780
acagacaagc tgtgaccgtc tccgggagct gcatgtgtca gaggttttca ccgtcatcac    3840
cgaaacgcgc gaggcag                                                  3857
```

<210> SEQ ID NO 116
<211> LENGTH: 4019
<212> TYPE: DNA
<213> ORGANISM: Artificial Sequence
<220> FEATURE:
<223> OTHER INFORMATION: pEX205

<400> SEQUENCE: 116

```
gatctcgatc ccgcgaaatt aatacgactc actataggga gaccacaacg gtttccctct      60
agaaataatt ttgtttaact ttaagaagga gatatacata tgaacgctgg tgtcactcag     120
accccaaaat tccaggtcct gaagacagga cagagcatga cactgcagtg tgcccaggat     180
atgaaccatg aatacatgtc ctggtatcga caagacccag gcatggggct gaggctgatt     240
cattactcag ttggtgctgg tatcactgac caaggagaag tccccaatgg ctacaatgtc     300
tccagatcaa ccacagagga tttcccgctc aggctgctgt cggctgctcc ctcccagaca     360
tctgtgtact ctgtgccag caggccggga ctagcgggag ggcgaccaga gcagtacttc     420
gggccgggca ccaggctcac ggtcacagag gacctgaaaa acgtgttccc acccgaggtc     480
gctgtgtttg agccatcaga agcagagatc tcccacaccc aaaaggccac actggtgtgc     540
ctggccacag gcttctaccc cgaccacgtg agctgagct ggtgggtgaa tgggaaggag     600
```

```
gtgcacagtg gggtcagcac agacccgcag cccctcaagg agcagcccgc cctcaatgac    660
tccagatacg ctctgagcag ccgcctgagg gtctcggcca ccttctggca ggaccccgc    720 aaccacttcc gctgtcaagt ccagttctac gggctctcgg agaatgacga gtggacccag    780
gatagggcca aacccgtcac ccagatcgtc agcgccgagg cctggggtag agcagacccc    840
gggggtctga ctgatacact ccaagcggag acagatcaac ttgaagacaa gaagtctgcg    900
ttgcagaccg agattgccaa tctactgaaa gagaaggaaa aactagagtt catcctggca    960
gcttacggat ccggtggtgg tctgaacgat attttttgaag ctcagaaaat cgaatggcat   1020
taagcttgaa ttccgatccg gctgctaaca aagcccgaaa ggaagctgag ttggctgctg   1080
ccaccgctga gcaataacta gcataacccc ttggggcctc taaacgggtc ttgaggggtt   1140
ttttgctgaa aggaggaact atatccggat aattcttgaa gacgaaaggg cctcgtgata   1200
cgcctatttt tataggttaa tgtcatgata ataatggttt cttagacgtc aggtggcact   1260
tttcggggaa atgtgcgcgg aacccctatt tgtttatttt tctaaataca ttcaaatatg   1320
tatccgctca tgagacaata accctgataa atgcttcaat aatattttgt taaaattcgc   1380
gttaaatttt tgttaaatca gctcattttt taaccaatag gccgaaatcg gcaaaatccc   1440
ttataaatca aaagaataga ccgagatagg gttgagtgtt gttccagttt ggaacaagag   1500
tccactatta agaacgtgg actccaacgt caaagggcga aaaaccgtct atcagggcga   1560
tggcccacta cgtgaaccat caccctaatc aagttttttg gggtcgaggt gccgtaaagc   1620
actaaatcgg aaccctaaag ggagcccccg atttagagct tgacggggaa agccggcgaa   1680
cgtggcgaga aggaaggga agaaagcgaa aggagcgggc gctagggcgc tggcaagtgt   1740
agcggtcacg ctgcgcgtaa ccaccacacc cgccgcgctt aatgcgccgc tacagggcgc   1800
gtcaggtggc acttttcggg gaaatgtgcg cggaaccccct atttgtttat ttttctaaat   1860
acattcaaat atgtatccgc tcatgagaca ataaccctga taaatgcttc aataatattg   1920
aaaaaggaag agtatgagta ttcaacattt ccgtgtcgcc cttattccct ttttttgcggc   1980 attttgcctt cctgttttttg ctcacccaga aacgctggtg aaagtaaaag atgctgaaga   2040
tcagttgggt gcacgagtgg gttacatcga actggatctc aacagcggta agatccttga   2100
gagttttcgc cccgaagaac gttttccaat gatgagcact tttaaagttc tgctatgtgg   2160
cgcggtatta tcccgtgttg acgccgggca agagcaactc ggtcgccgca tacactattc   2220
tcagaatgac ttggttgagt actcaccagt cacagaaaag catcttacgg atggcatgac   2280
agtaagagaa ttatgcagtg ctgccataac catgagtgat aacactgcgg ccaacttact   2340
tctgacaacg atcggaggac cgaaggagct aaccgctttt ttgcacaaca tgggggatca   2400
tgtaactcgc cttgatcgtt gggaaccgga gctgaatgaa gccataccaa acgacgagcg   2460
tgacaccacg atgcctgcag caatggcaac aacgttgcgc aaactattaa ctggcgaact   2520
acttactcta gcttcccggc aacaattaat agactggatg gaggcggata agttgcagg    2580 accacttctg cgctcggccc ttccggctgg ctggtttatt gctgataaat ctggagccgg   2640
tgagcgtggg tctcgcggta tcattgcagc actggggcca gatggtaagc cctcccgtat   2700
cgtagttatc tacacgacgg ggagtcaggc aactatggat gaacgaaata gacagatcgc   2760
tgagataggt gcctcactga ttaagcattg gtaactgtca gaccaagttt actcatatat   2820
actttagatt gatttaaaac ttcatttttta atttaaaagg atctaggtga agatccttttt   2880 tgataatctc atgaccaaaa tcccttaacg tgagttttcg ttccactgag cgtcagaccc   2940
cgtagaaaag atcaaaggat cttcttgaga tccttttttt ctgcgcgtaa tctgctgctt   3000
```

-continued

```
gcaaacaaaa aaaccaccgc taccagcggt ggtttgtttg ccggatcaag agctaccaac    3060 tcttttccg  aaggtaactg gcttcagcag agcgcagata ccaaatactg tccttctagt    3120
gtagccgtag ttaggccacc acttcaagaa ctctgtagca ccgcctacat acctcgctct    3180
gctaatcctg ttaccagtgg ctgctgccag tggcgataag tcgtgtctta ccgggttgga    3240
ctcaagacga tagttaccgg ataaggcgca gcggtcgggc tgaacggggg gttcgtgcac    3300
acagcccagc ttggagcgaa cgacctacac cgaactgaga tacctacagc gtgagctatg    3360
agaaagcgcc acgcttcccg aagggagaaa ggcggacagg tatccggtaa gcggcagggt    3420
cggaacagga gagcgcacga gggagcttcc aggggggaaac gcctggtatc tttatagtcc    3480
tgtcgggttt cgccacctct gacttgagcg tcgattttg tgatgctcgt caggggggcg    3540
gagcctatgg aaaaacgcca gcaacgcggc cttttttacgg ttcctggcct tttgctggcc    3600
ttttgctcac atgttctttc ctgcgttatc ccctgattct gtggataacc gtattaccgc    3660
ctttgagtga gctgataccg ctcgccgcag ccgaacgacc gagcgcagcg agtcagtgag    3720
cgaggaagcg gaagagcgcc tgatgcggta ttttctcctt acgcatctgt gcggtatttc    3780
acaccgcaat ggtgcactct cagtacaatc tgctctgatg ccgcatagtt aagccagtat    3840
acactccgct atcgctacgt gactgggtca tggctgcgcc ccgacacccg ccaacacccg    3900
ctgacgcgcc ctgacgggct tgtctgctcc cggcatccgc ttacagacaa gctgtgaccg    3960
tctccgggag ctgcatgtgt cagaggtttt caccgtcatc accgaaacgc gcgaggcag     4019
```

<210> SEQ ID NO 117
<211> LENGTH: 112
<212> TYPE: PRT
<213> ORGANISM: Artificial Sequence
<220> FEATURE:
<223> OTHER INFORMATION: synthesized Ig4 TCR beta chain variable domain variant

<400> SEQUENCE: 117

```
Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Gln Gly Glu Val Pro Asn Gly Tyr Asn
    50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asp Thr Gly Glu Leu Phe Phe Gly Glu Gly Ser Arg Leu Thr Val Leu
            100                 105                 110
```

<210> SEQ ID NO 118
<211> LENGTH: 112
<212> TYPE: PRT
<213> ORGANISM: Artificial Sequence
<220> FEATURE:
<223> OTHER INFORMATION: synthesized Ig4 TCR beta chain variable domain variant

<400> SEQUENCE: 118

```
Met Gly Val Thr Gln Thr Pro Lys Phe Gln Val Leu Lys Thr Gly Gln
1               5                   10                  15
```

```
Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Ala Ile Gln Thr Thr Asp Arg Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Leu Gly
                 85                  90                  95

Asn Thr Gly Glu Leu Phe Phe Gly Glu Gly Ser Arg Leu Thr Val Leu
            100                 105                 110
```

<210> SEQ ID NO 119
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 119

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Ala Ile Gln Thr Thr Asp Gln Gly Glu Val Pro Asn Gly Tyr Asn
 50                  55                  60

Val Ser Arg Ser Thr Ile Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                 85                  90                  95

Asn Thr Gly Glu Leu Phe Phe Gly Glu Gly Ser Arg Leu Thr Val Leu
            100                 105                 110
```

<210> SEQ ID NO 120
<211> LENGTH: 112
<212> TYPE: PRT
<213> ORGANISM: Artificial Sequence
<220> FEATURE:
<223> OTHER INFORMATION: synthesized Ig4 TCR beta chain variable domain
      variant

<400> SEQUENCE: 120

```
Met Gly Val Thr Gln Thr Pro Lys Phe Gln Val Leu Lys Thr Gly Gln
 1               5                  10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
            35                  40                  45

Val Ser Val Gly Met Thr Asp Arg Gly Glu Val Pro Asn Gly Tyr Asn
 50                  55                  60

Val Ser Arg Ser Thr Thr Glu Asp Phe Pro Leu Arg Leu Leu Ser Ala
 65                  70                  75                  80

Ala Pro Ser Gln Thr Ser Val Tyr Phe Cys Ala Ser Ser Tyr Val Gly
                 85                  90                  95

Asp Thr Gly Glu Leu Phe Phe Gly Glu Gly Ser Arg Leu Thr Val Leu
```

<210> SEQ ID NO 121
<211> LENGTH: 112
<212> TYPE: PRT
<213> ORGANISM: Artificial Sequence
<220> FEATURE:
<223> OTHER INFORMATION: synthesized Ig4 TCR beta chain variable domain variant

<400> SEQUENCE: 121

Met Gly Val Thr Gln Thr Pro Lys Phe Gln Val Leu Lys Thr Gly Gln
1               5                   10                  15

Ser Met Thr Leu Gln Cys Ala Gln Asp Met Asn His Glu Tyr Met Ser
            20                  25                  30

Trp Tyr Arg Gln Asp Pro Gly Met Gly Leu Arg Leu Ile His Tyr Ser
        35                  40                  45

Val Ala Ile Gln Thr Thr Asp Arg Gly Glu Val Pro Asn Gly Tyr Asn
50                  55                  60

Val Ser Arg Ser Thr Ile Glu Asp Phe Pro Leu Arg Leu Leu Ser Ala
65                  70                  75                  80

Ala Pro Ser Gln Thr Ser Val Tyr Phe Cys Ala Ser Ser Tyr Val Gly
                85                  90                  95

Asn Thr Gly Glu Leu Phe Phe Gly Glu Gly Ser Arg Leu Thr Val Leu
            100                 105                 110

<210> SEQ ID NO 122
<211> LENGTH: 162
<212> TYPE: PRT
<213> ORGANISM: Artificial Sequence
<220> FEATURE:
<223> OTHER INFORMATION: C58c61 alpha with truncated TRAC

<400> SEQUENCE: 122

Met Lys Gln Glu Val Thr Gln Ile Pro Ala Ala Leu Ser Val Pro Glu
1               5                   10                  15

Gly Glu Asn Leu Val Leu Asn Cys Ser Phe Thr Asp Ser Ala Ile Tyr
            20                  25                  30

Asn Leu Gln Trp Phe Arg Gln Asp Pro Gly Lys Gly Leu Thr Ser Leu
        35                  40                  45

Leu Leu Ile Thr Pro Trp Gln Arg Glu Gln Thr Ser Gly Arg Leu Asn
50                  55                  60

Ala Ser Leu Asp Lys Ser Ser Gly Arg Ser Thr Leu Tyr Ile Ala Ala
65                  70                  75                  80

Ser Gln Pro Gly Asp Ser Ala Thr Tyr Leu Cys Ala Val Arg Pro Leu
                85                  90                  95

Leu Asp Gly Thr Tyr Ile Pro Thr Phe Gly Arg Gly Thr Ser Leu Ile
            100                 105                 110

Val His Pro Tyr Ile Gln Asn Pro Asp Pro Ala Val Tyr Gln Leu Arg
        115                 120                 125

Asp Ser Lys Ser Ser Asp Lys Ser Val Cys Leu Phe Thr Asp Phe Asp
130                 135                 140

Ser Gln Thr Asn Val Ser Gln Ser Lys Asp Ser Asp Val Tyr Ile Thr
145                 150                 155                 160

Asp Lys

<210> SEQ ID NO 123
<211> LENGTH: 170
<212> TYPE: PRT

<213> ORGANISM: Artificial Sequence
<220> FEATURE:
<223> OTHER INFORMATION: C58c61 beta with truncated TRBC1

<400> SEQUENCE: 123

```
Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Ala Ile Gln Thr Thr Asp Gln Gly Glu Val Pro Asn Gly
    50                  55                  60

Tyr Asn Val Ser Arg Ser Thr Ile Glu Asp Phe Pro Leu Arg Leu Leu
65                  70                  75                  80

Ser Ala Ala Pro Ser Gln Thr Ser Val Tyr Phe Cys Ala Ser Ser Tyr
                85                  90                  95

Leu Gly Asn Thr Gly Glu Leu Phe Phe Gly Glu Gly Ser Arg Leu Thr
            100                 105                 110

Val Leu Glu Asp Leu Asn Lys Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Phe Pro Asp His Val Glu Leu Ser Trp Trp
145                 150                 155                 160

Val Asn Gly Lys Glu Val His Ser Gly Val
                165                 170
```

<210> SEQ ID NO 124
<211> LENGTH: 170
<212> TYPE: PRT
<213> ORGANISM: Artificial Sequence
<220> FEATURE:
<223> OTHER INFORMATION: C58c61 beta with truncated TRBC2

<400> SEQUENCE: 124

```
Met Asn Ala Gly Val Thr Gln Thr Pro Lys Phe Gln Val Leu Lys Thr
1               5                   10                  15

Gly Gln Ser Met Thr Leu Gln Cys Ala Gln Asp Met Asn His Glu Tyr
            20                  25                  30

Met Ser Trp Tyr Arg Gln Asp Pro Gly Met Gly Leu Arg Leu Ile His
        35                  40                  45

Tyr Ser Val Ala Ile Gln Thr Thr Asp Gln Gly Glu Val Pro Asn Gly
    50                  55                  60

Tyr Asn Val Ser Arg Ser Thr Ile Glu Asp Phe Pro Leu Arg Leu Leu
65                  70                  75                  80

Ser Ala Ala Pro Ser Gln Thr Ser Val Tyr Phe Cys Ala Ser Ser Tyr
                85                  90                  95

Leu Gly Asn Thr Gly Glu Leu Phe Phe Gly Glu Gly Ser Arg Leu Thr
            100                 105                 110

Val Leu Glu Asp Leu Lys Asn Val Phe Pro Pro Glu Val Ala Val Phe
        115                 120                 125

Glu Pro Ser Glu Ala Glu Ile Ser His Thr Gln Lys Ala Thr Leu Val
    130                 135                 140

Cys Leu Ala Thr Gly Phe Tyr Pro Asp His Val Glu Leu Ser Trp Trp
145                 150                 155                 160

Val Asn Gly Lys Glu Val His Ser Gly Val
```

<210> SEQ ID NO 125
<211> LENGTH: 305
<212> TYPE: PRT
<213> ORGANISM: Artificial Sequence
<220> FEATURE:
<223> OTHER INFORMATION: C58c61 beta with truncated TRBC2 fused to wt human IL-2

<400> SEQUENCE: 125

```
Met Asn Ala Gly Val Thr Gln Thr Pro Lys Phe Gln Val Leu Lys Thr
1               5                   10                  15
Gly Gln Ser Met Thr Leu Gln Cys Ala Gln Asp Met Asn His Glu Tyr
            20                  25                  30
Met Ser Trp Tyr Arg Gln Asp Pro Gly Met Gly Leu Arg Leu Ile His
        35                  40                  45
Tyr Ser Val Ala Ile Gln Thr Thr Asp Gln Gly Glu Val Pro Asn Gly
    50                  55                  60
Tyr Asn Val Ser Arg Ser Thr Ile Glu Asp Phe Pro Leu Arg Leu Leu
65                  70                  75                  80
Ser Ala Ala Pro Ser Gln Thr Ser Val Tyr Phe Cys Ala Ser Ser Tyr
                85                  90                  95
Leu Gly Asn Thr Gly Glu Leu Phe Phe Gly Glu Gly Ser Arg Leu Thr
            100                 105                 110
Val Leu Glu Asp Leu Lys Asn Val Phe Pro Pro Glu Val Ala Val Phe
        115                 120                 125
Glu Pro Ser Glu Ala Glu Ile Ser His Thr Gln Lys Ala Thr Leu Val
    130                 135                 140
Cys Leu Ala Thr Gly Phe Tyr Pro Asp His Val Glu Leu Ser Trp Trp
145                 150                 155                 160
Val Asn Gly Lys Glu Val His Ser Gly Val Pro Gly Ala Pro Thr Ser
                165                 170                 175
Ser Ser Thr Lys Lys Thr Gln Leu Gln Leu Glu His Leu Leu Leu Asp
            180                 185                 190
Leu Gln Met Ile Leu Asn Gly Ile Asn Asn Tyr Lys Asn Pro Lys Leu
        195                 200                 205
Thr Arg Met Leu Thr Phe Lys Phe Tyr Met Pro Lys Lys Ala Thr Glu
    210                 215                 220
Leu Lys His Leu Gln Cys Leu Glu Glu Glu Leu Lys Pro Leu Glu Glu
225                 230                 235                 240
Val Leu Asn Leu Ala Gln Ser Lys Asn Phe His Leu Arg Pro Arg Asp
                245                 250                 255
Leu Ile Ser Asn Ile Asn Val Ile Val Leu Glu Leu Lys Gly Ser Glu
            260                 265                 270
Thr Thr Phe Met Cys Glu Tyr Ala Asp Glu Thr Ala Thr Ile Val Glu
        275                 280                 285
Phe Leu Asn Arg Trp Ile Thr Phe Cys Gln Ser Ile Ile Ser Thr Leu
    290                 295                 300
Thr
305
```

<210> SEQ ID NO 126
<211> LENGTH: 9
<212> TYPE: PRT
<213> ORGANISM: Artificial Sequence
<220> FEATURE:
<223> OTHER INFORMATION: NY-ESO peptide

```
<400> SEQUENCE: 126

Ser Leu Leu Met Trp Ile Thr Gln Cys
1               5

<210> SEQ ID NO 127
<211> LENGTH: 9
<212> TYPE: PRT
<213> ORGANISM: Artificial Sequence
<220> FEATURE:
<223> OTHER INFORMATION: NY-ESO analogue

<400> SEQUENCE: 127

Ser Leu Leu Met Trp Ile Thr Gln Val
1               5
```